United States Patent
Masuyama et al.

(10) Patent No.: US 9,562,032 B2
(45) Date of Patent: Feb. 7, 2017

(54) SALT AND PHOTORESIST COMPOSITION COMPRISING THE SAME

(71) Applicant: SUMITOMO CHEMICAL COMPANY, LIMITED, Tokyo (JP)

(72) Inventors: Tatsuro Masuyama, Osaka (JP); Koji Ichikawa, Osaka (JP); Masafumi Yoshida, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 53 days.

(21) Appl. No.: 14/601,825

(22) Filed: Jan. 21, 2015

(65) Prior Publication Data

US 2015/0212407 A1    Jul. 30, 2015

(30) Foreign Application Priority Data

Jan. 24, 2014    (JP) .................. 2014-011112

(51) Int. Cl.
| | | |
|---|---|---|
| *C07D 317/72* | (2006.01) | |
| *C07D 319/08* | (2006.01) | |
| *C07D 327/04* | (2006.01) | |
| *C07D 327/06* | (2006.01) | |
| *G03F 7/039* | (2006.01) | |
| *G03F 7/20* | (2006.01) | |
| *C07C 381/12* | (2006.01) | |
| *G03F 7/004* | (2006.01) | |

(52) U.S. Cl.
CPC ........... *C07D 317/72* (2013.01); *C07C 381/12* (2013.01); *C07D 319/08* (2013.01); *C07D 327/06* (2013.01); *G03F 7/0045* (2013.01); *G03F 7/0046* (2013.01); *G03F 7/0397* (2013.01)

(58) Field of Classification Search
CPC ... C07D 319/04; C07D 319/06; C07D 319/08; C07D 327/02; C07D 327/04; C07D 327/06; C07D 327/08; C07D 339/02; C07D 317/72; G03F 7/0045; G03F 7/0392; G03F 7/20; C07C 381/12

See application file for complete search history.

(56) References Cited

U.S. PATENT DOCUMENTS

| | | | |
|---|---|---|---|
| 2011/0014568 A1 | 1/2011 | Ichikawa et al. | |
| 2013/0178521 A1* | 7/2013 | Ohkawa et al. | .............. 514/467 |

FOREIGN PATENT DOCUMENTS

| | | | |
|---|---|---|---|
| JP | 2010-132479 | * | 6/2010 |
| JP | 2010-195687 | * | 9/2010 |
| WO | WO 2012/039477 | * | 3/2012 |

OTHER PUBLICATIONS

Machine translation of JP 2010-195687, published on Sep. 9, 2010.*
Machine translation of JP 2010-134279, published on Jun. 17, 2010.*

* cited by examiner

*Primary Examiner* — Anca Eoff
(74) *Attorney, Agent, or Firm* — Birch, Stewart, Kolasch & Birch, LLP

(57) ABSTRACT

A salt which has a group represented by formula (a):

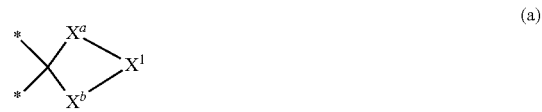

wherein $X^a$ and $X^b$ each independently represent an oxygen atom or a sulfur group;
$X^1$ represents a C1-C12 divalent saturated hydrocarbon group which has a hydroxy group; and
\* represents a binding site.

13 Claims, No Drawings

SALT AND PHOTORESIST COMPOSITION COMPRISING THE SAME

This nonprovisional application claims priority under 35 U.S.C. §119(a) on Patent Application No. 2014-011112 filed in JAPAN on Jan. 24, 2014, the entire contents of which are hereby incorporated by reference.

FIELD OF THE INVENTION

The present invention relates to a salt and a photoresist composition comprising the same.

BACKGROUND OF THE INVENTION

A photoresist composition is used for semiconductor microfabrication employing a lithography process.

JP2011-37837A1 discloses a photoresist composition comprising a salt represented by the following formula:

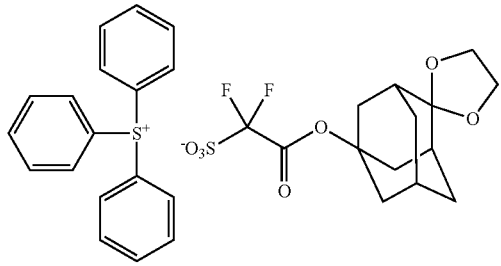

as an acid generator.

SUMMARY OF THE INVENTION

The present invention relates to the followings:

[1] A salt which has a group represented by formula (a):

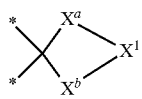

(a)

wherein $X^a$ and $X^b$ each independently represent an oxygen atom or a sulfur group;
$X^1$ represents a C1-C12 divalent saturated hydrocarbon group which has a hydroxy group; and
* represents a binding site.

[2] The salt according to [1]
comprising a cation and an anion which has the group represented by formula (a).

[3] The salt according to [2]
wherein the cation is an arylsulfonium cation.

[4] The salt according to any one of [1] to [3]
the group represented by formula (a) forms a moiety represented by formula (a1):

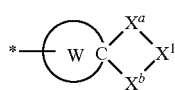

(a1)

wherein $X^a$, $X^b$, $X^1$ and * are as defined in [1]; and
the ring W represents a C3-C36 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them.

[5] The salt according to [4]
wherein the ring W is a C6-C10 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them.

[6] The salt according to [2]
wherein the anion is represented by formula (a2):

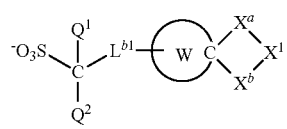

(a2)

in which $X^a$, $X^b$ and $X^1$ are as defined in [1];
the ring W represents a C3-C36 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them, $L^{b1}$ represents a C1-C24 divalent saturated hydrocarbon group where a methylene group can be replaced by an oxygen atom or a carbonyl group and where a hydrogen atom can be replaced by a fluorine atom or a hydroxy group; and
$Q^1$ and $Q^2$ each independently represent a fluorine atom or a C1-C6 perfluoroalkyl group.

[7] The salt according to [6]
wherein the ring W is a C6-C10 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them.

[8] The salt according to [6] or [7]
wherein $L^{b1}$ is *—CO—O—(CH$_2$)$_t$— where t is an integer of 0 to 6 and * represents a binding site to C($Q^1$)($Q^2$), or *—CH$_2$—O—CO— where * represents a binding site to C($Q^1$)($Q^2$).

[9] The salt according to any one of [1] to [8]
wherein $X^1$ is a C1-C6 alkanediyl group which has a methoxy group.

[10] The salt according to any one of [1] to [9] wherein $X^1$ is a divalent group represented by formula (X1-1), formula ($X^1$-2), formula ($X^1$-3) or formula ($X^1$-4):

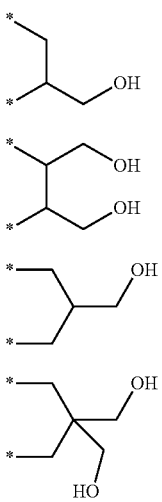

where * represents a binding site to $X^a$ or $X^b$.

[11] An acid generator which comprises the salt according to any one of [1] to [10].

[12] A photoresist composition comprising
the acid generator according to [11] and
a resin which has an acid-labile group.

[13] The photoresist composition according to [12], further comprising a salt which has an acidity weaker than an acid generated from the acid generator.

[14] A process for producing a photoresist pattern comprising the following steps (1) to (5):
(1) a step of applying the photoresist composition according [12] or [13] on a substrate,
(2) a step of forming a composition film by conducting drying,
(3) a step of exposing the composition film to radiation,
(4) a step of baking the exposed composition film, and
(5) a step of developing the baked composition film.

Hereinafter, the salt which has a group represented by formula (a) is sometimes referred to as "Salt (a)".

DESCRIPTION OF PREFERRED EMBODIMENTS

<Salt (a)>
Salt (a) has a group represented by formula (I).

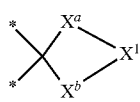

In formula (a), $X^a$ and $X^b$ each independently represent an oxygen atom or a sulfur group;
$X^1$ represents a C1-C12 divalent saturated hydrocarbon group which has a hydroxy group; and
* represents a binding site.

$X^a$ and $X^b$ are preferably the same atom each other, more preferably an oxygen atom.

For $X^1$, the divalent saturated hydrocarbon group includes alkanediyl groups, divalent alicyclic hydrocarbon groups, and combination of them.

Specific examples of the alkanediyl groups include
linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, and an octane-1,8-diyl group;
branched alkanediyl groups such as an ethane-1,1-diyl group, a propane-1,1-diyl group, a propane-1,2-diyl group, a propane-2,2-diyl group, a pentane-2,4-diyl group, a 2-methyl propane-1,3-diyl group, a 2-methyl propane-1,2-diyl group, a pentane-1,4-diyl group, and a 2-methyl butane-1,4-diyl group;
divalent monocyclic alicyclic saturated hydrocarbon group including cycloalkanediyl groups such as a cyclobutane-1,3-diyl group, a cyclopentane-1,3-diyl group, a cyclohexane-1,4-diyl group, and a cyclooctane-1,5-diyl group; and
divalent polycyclic saturated hydrocarbon groups such as a norbornane-1,4-diyl group, a norbornane-2,5-diyl group, an adamantane-1,5-diyl group, and an adamantane-2,6-diyl group.

The divalent saturated hydrocarbon group for $X^1$ is preferably a C1-C12 alkanediyl group, more preferably a C1-C6 alkanediyl group. $X^1$ has a hydroxy group, preferably one or two hydroxy groups.

$X^1$ is preferably a C1-C6 alkanediyl group which has a hydroxymethyl group, more preferably a divalent group represented by formula ($X^1$-1), formula ($X^1$-2), formula ($X^1$-3) or formula ($X^1$-4):

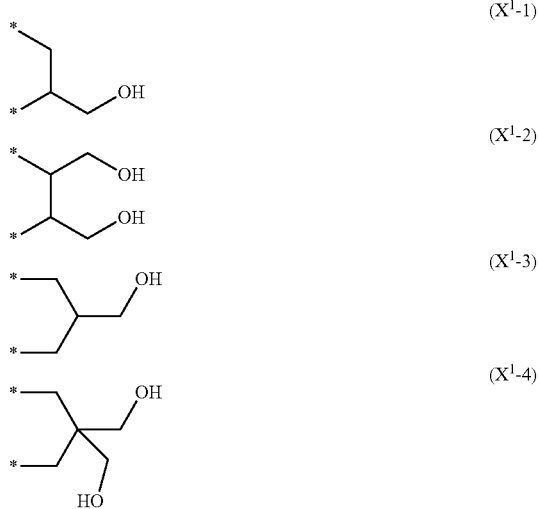

where * represents a binding site to $X^a$ or $X^b$.

Salt (a) has preferably a moiety represented by formula (a1). The moiety is formed from the group represented by formula (a), and composed of a ring W and the group:

In formula (a1), $X^a$, $X^b$, $X^1$ and * are as defined above, and the ring W represents a C3-C36 alicyclic hydrocarbon group in which a methylene group can be replaced by an oxygen atom, a sulfur atom, a carbonyl group or a sulfonyl group, and in which a hydrogen atom can be replaced by a hydroxy group, a eC1-C12 alkyl group, a C1-C12 alkoxy group, a C3-C12 alicyclic hydrocarbon group, a C6-C10 aromatic hydrocarbon group or a combination of any two or more of them.

Examples of the ring W include the rings represented by any one of formulae (a1-1) to (a1-11), those in which a methylene group has been replaced by an oxygen atom, a sulfur atom, a carbonyl group, a sulfonyl group, or those in which a hydrogen atom can be replaced by a hydroxy group, a c1-C12 alkyl group, a C1-C12 alkoxy group, a C3-C12 alicyclic hydrocarbon group, a C6-C10 aromatic hydrocarbon group or a combination of any two or more of them.

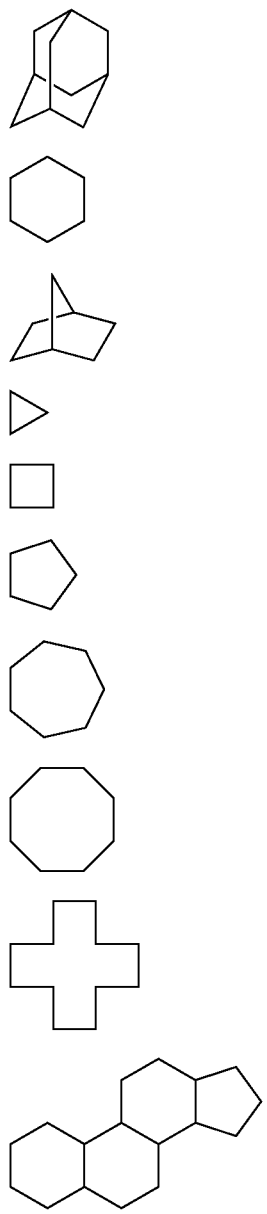

The alkyl group may be a linear or branched one, examples of which include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group, a nonyl group, an undecyl group and a decyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

The alicyclic hydrocarbon group may be a monocyclic or polycyclic one, examples of which include the following ones.

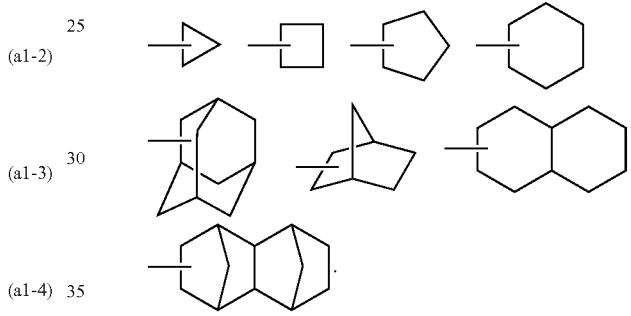

Examples of the aromatic hydrocarbon group include a phenyl group and a naphthyl group.

The ring W is preferably a C6-C10 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them, and more preferably one represented by formula (a1-1), (a1-2) or (a1-3) and the one represented by formula (a1-1), (a1-2) or (a1-3) in which a methylene group has been replaced by an oxygen atom, a sulfur atom, a carbonyl group or a sulfonyl group, and in which a hydrogen atom has been replaced by a hydroxy group, a c1-C12 alkyl group, a C1-C12 alkoxy group, or a C3-C12 alicyclic hydrocarbon group.

Salt (a) may have the group represented by formula (a) in its anion or its cation, preferably in its anion.

The cation of Salt (a) is preferably an organic cation.

Salt (a) is preferably one which comprises a cation and an anion having the group represented by formula (a), more preferably one which comprises an organic cation and an anion having the group represented by formula (a).

The anion having the group represented by formula (a) has preferably the moiety of formula (a1), which is preferably one represented by formula (a2):

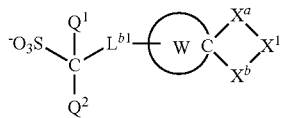

(a2)

in which $X^a$, $X^b$, $X^1$ and the ring W are as defined above;
$L^{b1}$ represents a C1-C24 divalent saturated hydrocarbon group where a methylene group can be replaced by an oxygen atom or a carbonyl group and where a hydrogen atom can be replaced by a fluorine atom or a hydroxy group; and
$Q^1$ and $Q^2$ each independently represent a fluorine atom or a C1-C6 perfluoroalkyl group.

In formula (a2), $Q^1$ and $Q^2$ independently each represent a fluorine atom or a C1-C6 perfluoroalkyl group.

Examples of the C1-C6 perfluoroalkyl group represented by $Q^1$ and $Q^2$ include a trifluoromethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group.

$Q^1$ and $Q^2$ independently each represent preferably a fluorine atom or a trifluoromethyl group, more preferably a fluorine atom.

$L^{b1}$ represents a C1-C24 divalent saturated hydrocarbon group where a methylene group can be replaced by an oxygen atom or a carbonyl group and where a hydrogen atom can be replaced by a fluorine atom or a hydroxy group.

Examples of the divalent saturated hydrocarbon group include a linear alkanediyl groups, branched alkanediyl groups, monocyclic or polycyclic alicyclic saturated hydrocarbon groups, and a group formed by combining two or more of them.

Specific examples of the divalent saturated hydrocarbon group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl groups; branched alkanediyl groups such as an ethane-1,1-diyl group, a propane-1,1-diyl group, a propane-1,2-diyl group, a propane-2,2-diyl group, a pentane-2,4-diyl group, a 2-methyl propane-1,3-diyl group, a 2-methyl propane-1,2-diyl group, a pentane-1,4-diyl group, and a 2-methyl butane-1,4-diyl group; divalent monocyclic alicyclic saturated hydrocarbon group including cycloalkanediyl groups such as a cyclobutane-1,3-diyl group, a cyclopentane-1,3-diyl group, a cyclohexane-1,4-diyl group, and a cyclooctane-1,5-diyl group; and
divalent polycyclic saturated hydrocarbon groups such as a norbornane-1,4-diyl group, a norbornane-2,5-diyl group, an adamantane-1,5-diyl group, an adamantane-2,6-diyl group.

Specific examples of the divalent saturated hydrocarbon group where a methylene group has been replaced by an oxygen atom or a carbonyl group include those represented by formulae (b1-1), (b1-2) and (b1-3).

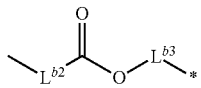

(b1-1)

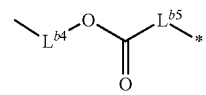

(b1-2)

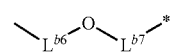

(b1-3)

In these formulae, * represents a binding site to the ring W of formula (a2).

In formula (b1-1), $L^{b2}$ represents a single bond or a C1-C22 divalent saturated hydrocarbon group where a hydrogen atom can be replaced by a fluorine atom;
$L^{b3}$ represents a single bond or a C1-C22 divalent saturated hydrocarbon group where a hydrogen atom may be replaced by a fluorine atom or a hydroxy group, and where a methylene group can be replaced by —O— or —CO—; provided that total carbon atoms in $L^{b2}$ and $L^{b3}$ are 22 or less.

In formula (b1-2), $L^{b4}$ represents a single bond or a C1-C22 divalent saturated hydrocarbon group where a hydrogen atom can be replaced by a fluorine atom;
$L^{b5}$ represents a single bond or a C1-C22 divalent saturated hydrocarbon group where a hydrogen atom may be replaced by a fluorine atom or a hydroxy group, and where a methylene group can be replaced by —O— or —CO—; provided that total carbon atoms in $L^{b4}$ and $L^{b5}$ are 22 or less.

In formula (b1-3), $L^{b6}$ represents a single bond or a C1-C23 divalent saturated hydrocarbon group where a hydrogen atom can be replaced by a fluorine atom or a hydroxy group;
$L^{b7}$ represents a single bond or a C1-C23 divalent saturated hydrocarbon group where a hydrogen atom may be replaced by a fluorine atom or a hydroxy group, and where a methylene group can be replaced by —O— or —CO—; provided that total carbon atoms in $L^{b6}$ and $L^{b7}$ are 23 or less and —CO— is not bonded to the oxygen atom between $L^{b6}$ and $L^{b7}$.

In formulae (b1-1) to (b1-3), the number of the carbon atoms in the divalent saturated hydrocarbon groups include that of the carbon atoms in the methylene groups which have been replaced by an oxygen atom or a carbonyl group.

Specific examples of the divalent saturated hydrocarbon groups for $L^{b2}$, $L^{b3}$, $L^{b4}$, $L^{b5}$, $L^{b6}$ and $L^{b7}$ include the same as referred to for $L^{b1}$.

$L^{b2}$ is preferably a single bond.
$L^{b3}$ is preferably a C1-C4 alkanediyl group.
$L^{b4}$ is preferably a C1-C8 divalent saturated hydrocarbon group where a hydrogen atom may be replaced by a fluorine atom.
$L^{b5}$ is preferably a single bond or a C1-C8 divalent saturated hydrocarbon group.
$L^{b6}$ is preferably a single bond or a C1-C4 divalent saturated hydrocarbon group where a hydrogen atom can be replaced by a fluorine atom.
$L^{b7}$ is preferably a single bond or a C1-C18 divalent saturated hydrocarbon group where a hydrogen atom can be replaced by a fluorine atom or a hydroxy group, and where a methylene group can be replaced by —O— or —CO—.

As $L^{b1}$, the divalent saturated hydrocarbon group where a methylene group has been replaced by —O— or —CO— is preferably one represented by formula (b1-1) or (b1-2).

Examples of one represented by formula (b1-1) include those represented by formulae (b1-4) to (b1-8).

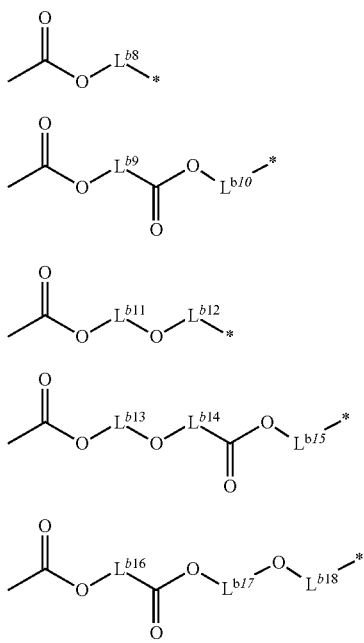

(b1-4)

(b1-5)

(b1-6)

(b1-7)

(b1-8)

In these formulae, * represents a binding site to the ring W of formula (a2).

In formula (b1-4), $L^{b8}$ represents a single bond or a C1-C22 divalent saturated hydrocarbon group where a hydrogen atom can be replaced by a fluorine atom or a hydroxy group.

In formula (b1-5), $L^{b9}$ represents a C1-C20 divalent saturated hydrocarbon group and $L^{b10}$ represents a single bond or a C1-C19 divalent saturated hydrocarbon group where a hydrogen atom can be replaced by a fluorine atom or a hydroxy group, provided that total carbon atoms in $L^{b9}$ and $L^{b10}$ are 20 or less.

In formula (b1-6), $L^{b11}$ represents a C1-C21 divalent saturated hydrocarbon group and $L^{b12}$ represents a single bond or a C1-C20 divalent saturated hydrocarbon group where a hydrogen atom can be replaced by a fluorine atom or a hydroxy group, provided that total carbon atoms in $L^{b11}$ and $L^{b12}$ are 21 or less.

In formula (b1-7), $L^{b13}$ represents a C1-C19 divalent saturated hydrocarbon group, $L^{b14}$ represents a single bond or a C1-C18 divalent saturated hydrocarbon group and $L^{b15}$ represents a single bond or a C1-C18 divalent saturated hydrocarbon group where a hydrogen atom can be replaced by a fluorine atom or a hydroxy group, provided that total carbon atoms in $L^{b13}$, $L^{b14}$ and $L^{b15}$ are 19 or less.

In formula (b1-8), $L^{b16}$ represents a C1-C18 divalent saturated hydrocarbon group, $L^{b17}$ represents a C1-C18 divalent saturated hydrocarbon group and $L^{b18}$ represents a single bond or a C1-C17 divalent saturated hydrocarbon group where a hydrogen atom can be replaced by a fluorine atom or a hydroxy group, provided that total carbon atoms in $L^{b16}$, $L^{b17}$ and $L^{b18}$ are 19 or less.

$L^{b8}$ is preferably a C1-C4 alkanediyl group.

$L^{b9}$ is preferably a C1-C8 divalent saturated hydrocarbon group.

$L^{b10}$ is preferably a single bond or a C1-C19 divalent saturated hydrocarbon group, more preferably a single bond or a C1-C8 divalent saturated hydrocarbon group.

$L^{b11}$ is preferably a C1-C8 divalent saturated hydrocarbon group $L^{b12}$ is preferably a single bond or a C1-C8 divalent saturated hydrocarbon group.

$L^{b13}$ is preferably a C1-C12 divalent saturated hydrocarbon group.

$L^{b14}$ is preferably a single bond or a C1-C6 divalent saturated hydrocarbon group.

$L^{b15}$ is preferably a single bond or a C1-C18 divalent saturated hydrocarbon group, more preferably a single bond or a C1-C8 divalent saturated hydrocarbon group.

$L^{b16}$ is preferably a C1-C12 divalent saturated hydrocarbon group.

$L^{b17}$ is preferably a C1-C6 divalent saturated hydrocarbon group.

$L^{b18}$ is preferably a single bond or a C1-C17 divalent saturated hydrocarbon group, more preferably a single bond or a C1-C4 divalent saturated hydrocarbon group, Examples of the group represented by formula (b1-4) include the following ones.

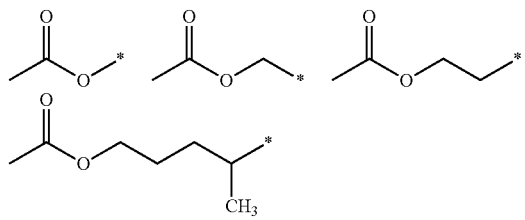

In each formula, * represents a binding site to the ring W of formula (a2)

Examples of the group represented by formula (b1-5) include the following ones.

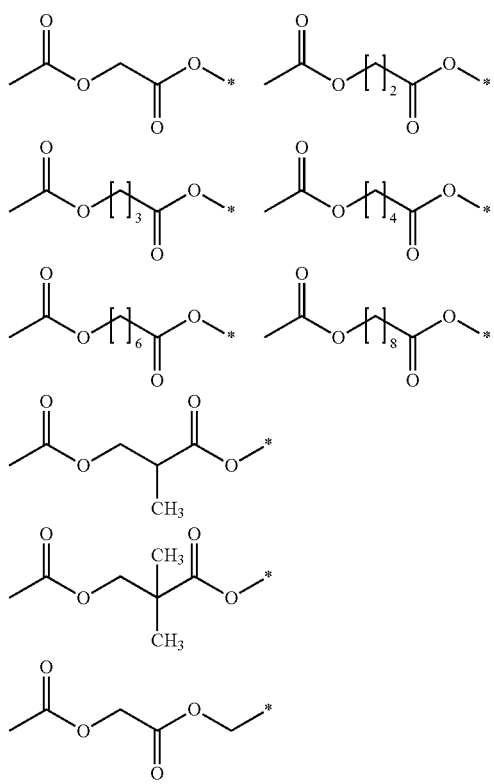

-continued
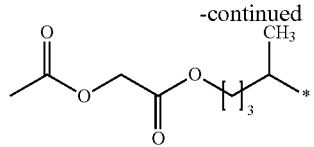
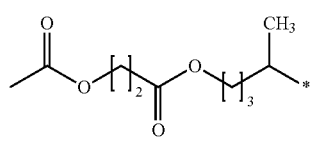
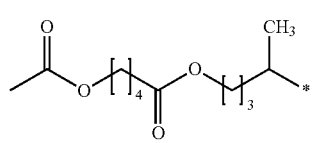
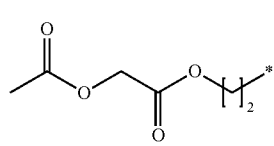
In each formula, * represents a binding site to the ring W of formula (a2).
Examples of the group represented by formula (b1-6) include the following ones.
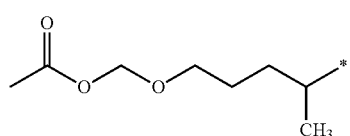
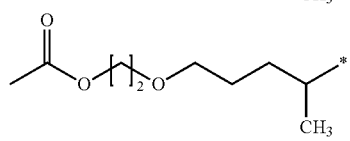
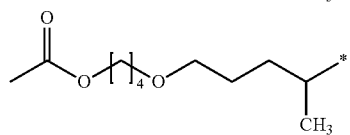
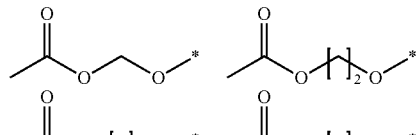
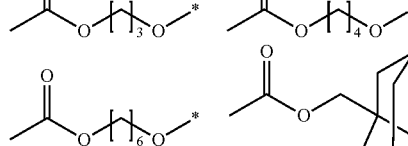
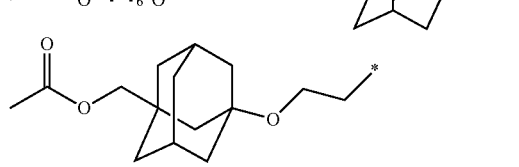
In each formula, * represents a binding site to the ring W of formula (a2)
Examples of the group represented by formula (b1-7) include the following ones.
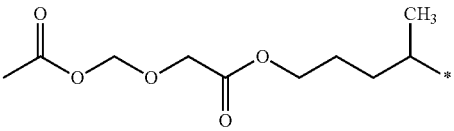
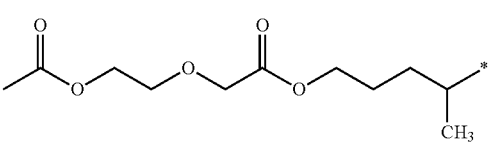
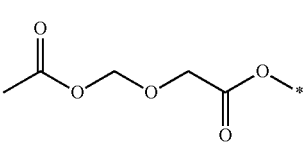
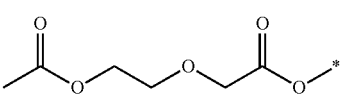
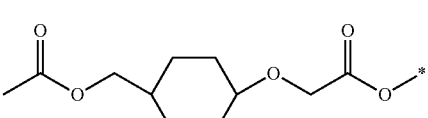
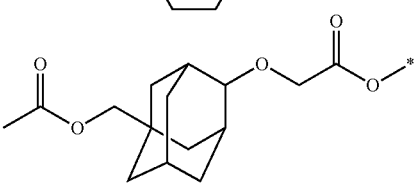
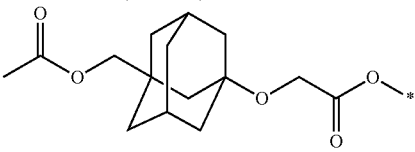
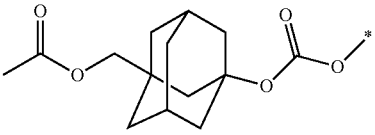
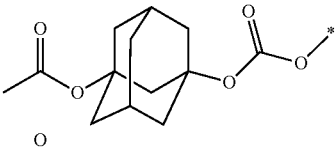
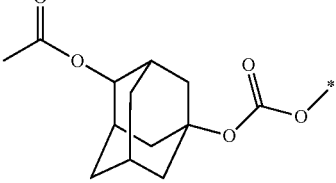

In each formula, * represents a binding site to the ring W of formula (a2).

Examples of the group represented by formula (b1-8) include the following ones.

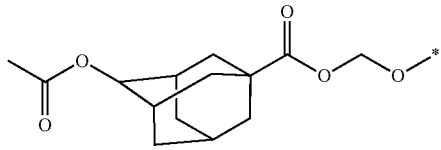

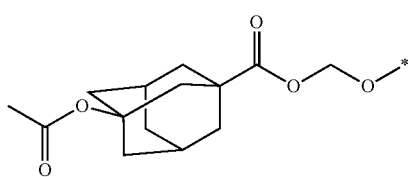

In each formula, * represents a binding site to the ring W of formula (a2).

Examples of the group represented by formula (b1-2) include the following ones.

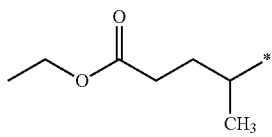

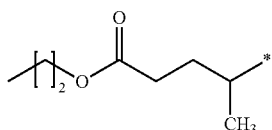

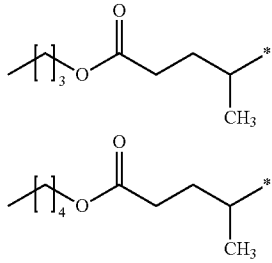

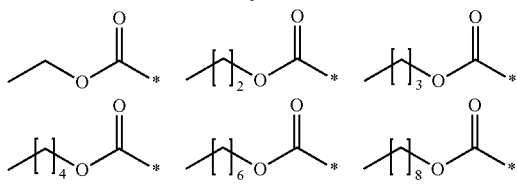

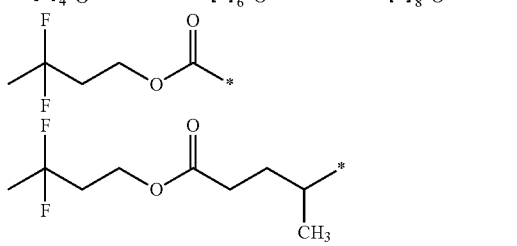

In each formula, * represents a binding site to the ring W of formula (a2).

Examples of one represented by formula (b1-3) include those represented by formulae (b1-9) to (b1-11).

(b1-9)

(b1-10)

(b1-11)

In these formulae, * represents a binding site to the ring W of formula (a2).

In formula (b1-9), $L^{b19}$ represents a single bond or a C1-C23 divalent saturated hydrocarbon group where a hydrogen atom can be replaced by a fluorine atom and $L^{b20}$ represents a single bond or a C1-C23 divalent saturated hydrocarbon group where a hydrogen atom can be replaced by a fluorine atom, a hydroxy group or an acyloxy group in which a methylene group can be replaced by an oxygen atom or a carbonyl group and in which a hydrogen atom can be replaced by a hydroxy group, provided that total carbon atoms in $L^{b19}$ and $L^{b20}$ are 23 or less.

In formula (b1-10), $L^{b21}$ represents a single bond or a C1-C21 divalent saturated hydrocarbon group where a hydrogen atom can be replaced by a fluorine atom, $L^{b22}$ represents a single bond or a C1-C21 divalent saturated hydrocarbon group and $L^{b23}$ represents a single bond or a C1-C21 divalent saturated hydrocarbon group where a hydrogen atom can be replaced by a fluorine atom, a hydroxy group or an acyloxy group in which a methylene group can be replaced by an oxygen atom or a carbonyl group and in which a hydrogen atom can be replaced by a hydroxy group, provided that total carbon atoms in $L^{b21}$, $L^{b22}$ and $L^{b23}$ are 21 or less.

In formula (b1-11), $L^{b24}$ represents a single bond or a C1-C20 divalent saturated hydrocarbon group where a hydrogen atom can be replaced by a fluorine atom, $L^{b25}$ represents a C1-C21 divalent saturated hydrocarbon group and $L^{b26}$ represents a single bond or a C1-C20 divalent saturated hydrocarbon group where a hydrogen atom can be replaced by a fluorine atom, a hydroxy group or an acyloxy group in which a methylene group can be replaced by an oxygen atom or a carbonyl group and in which a hydrogen atom can be replaced by a hydroxy group, provided that total carbon atoms in $L^{b24}$, $L^{b25}$ and $L^{b25}$ are 21 or less.

In formulae (b1-9) to (b1-11), the number of the carbon atoms for the divalent saturated hydrocarbon groups include that of the carbon atoms in an acyloxy group, if a hydrogen atom therein has been replaced by the group.

Examples of acyloxy group include an acetyloxy group, a propionyloxy group, a butyryloxy group, a cyclohexylcarbonyloxy group, and an adamantylcarbonyloxy group.

Examples of acyloxy group which has a substituent include an oxoadamantylcarbonyloxy group, a hydroxyadamantylcarbonyloxy group, an oxocyclohexylcarbonyloxy group, and a hydroxycyclohexylcarbonyloxy group.

Examples of the group represented by formula (b1-9) include the following ones.

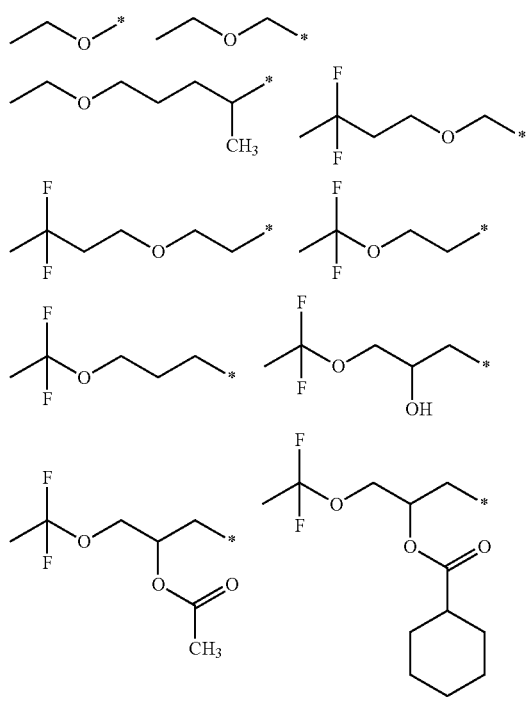
In each formula, * represents a binding site to the ring W of formula (a2).
Examples of the group represented by formula (b1-10) include the following ones.
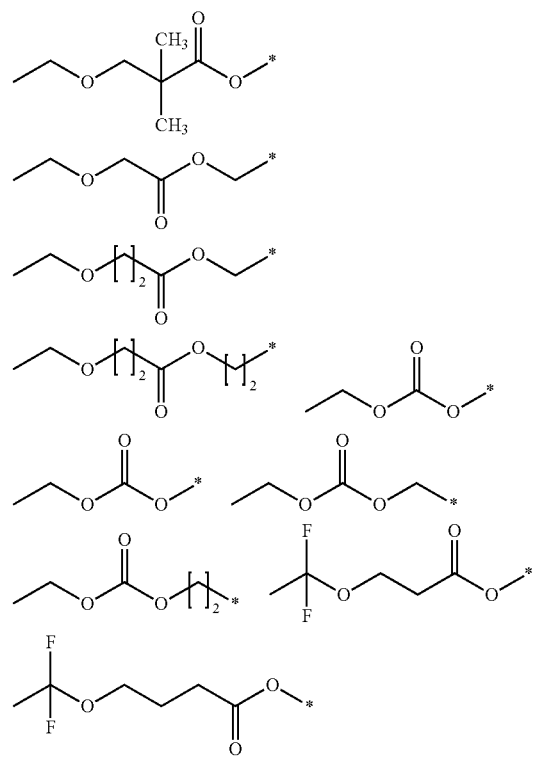
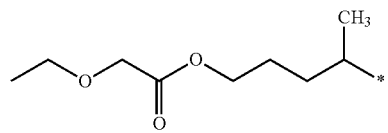
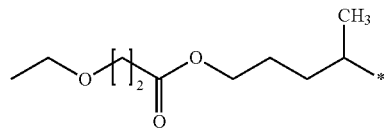
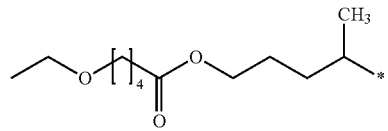
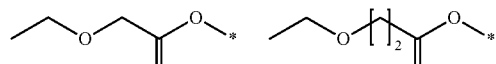
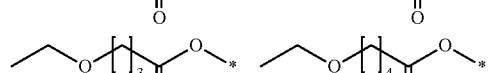
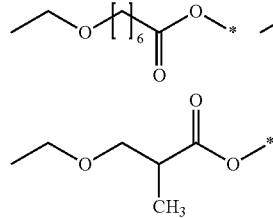
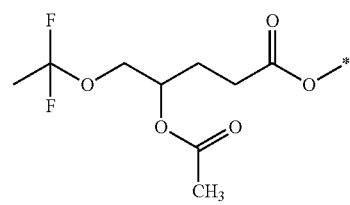
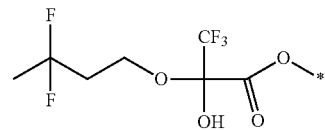
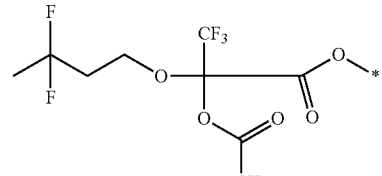
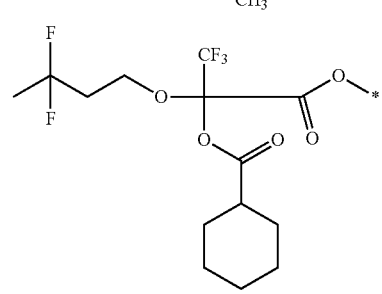

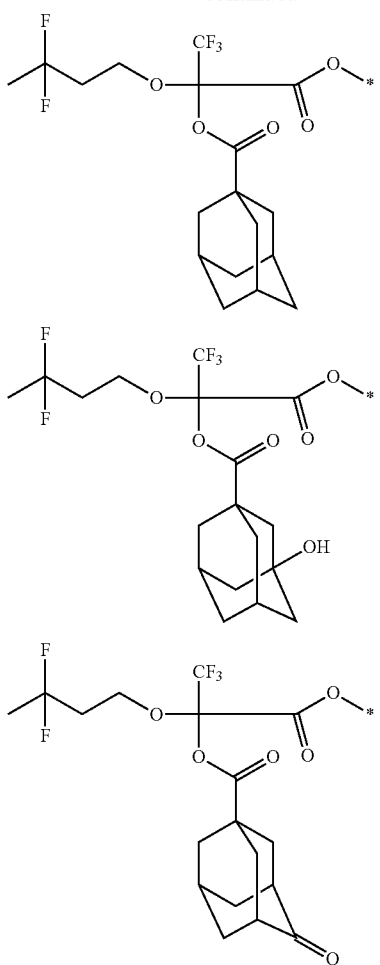
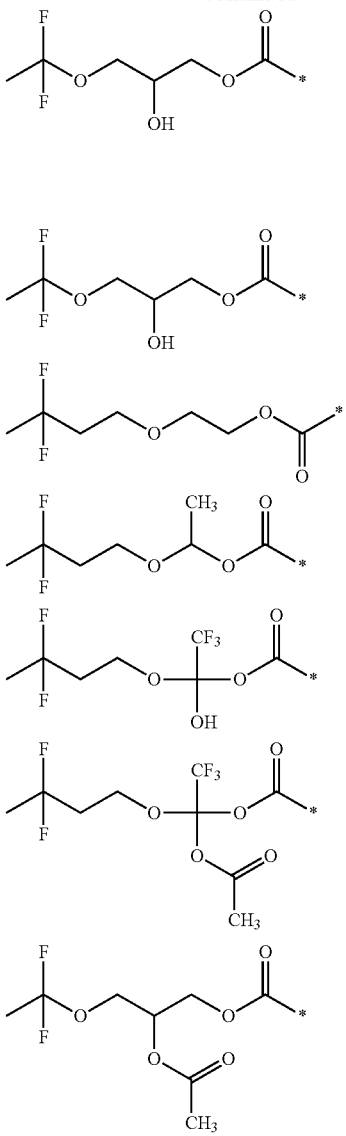
In each formula, * represents a binding site to the ring W of formula (a2).
Examples of the group represented by formula (b1-11) include the following ones.
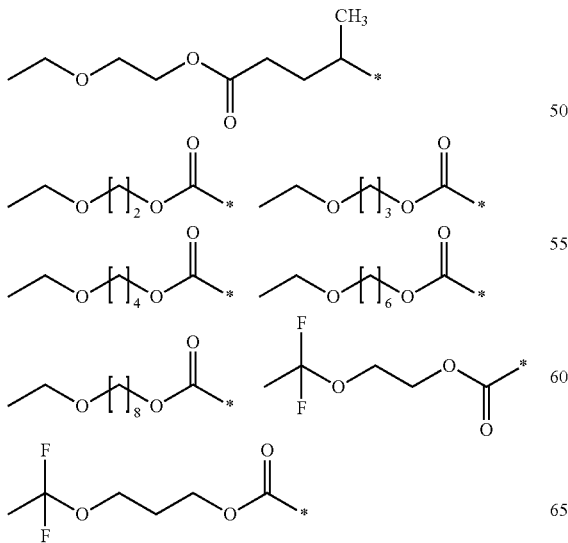
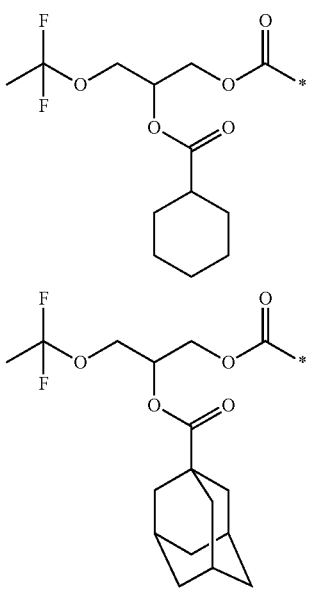

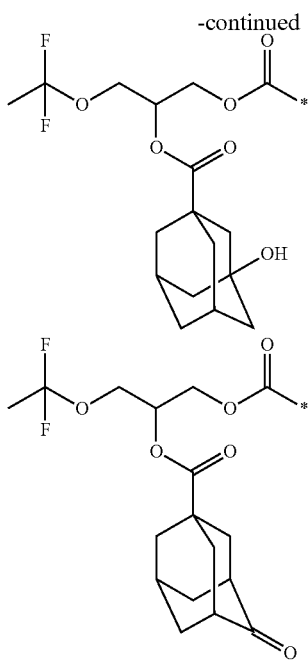

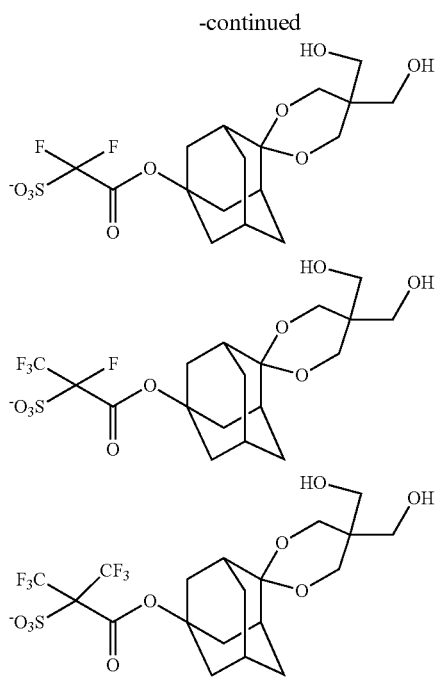

In each formula, * represents a binding site to the ring W of formula (a2).

$L^{b1}$ preferably represents a divalent saturated hydrocarbon group where a methylene group has been replaced by —O— or —CO—, more preferably a group represented by formula (b1-4) and a group represented by formula (b1-2) where $L^{b4}$ is a C1-C10 alkanediyl group and $L^{b5}$ is a single bond, still more preferably *—CO—O—$(CH_2)_t$— where t is an integer of 0 to 6 and * represents a binding site to $C(Q^1)(Q^2)$ or *—$CH_2$—O—CO— where * represents a binding site to $C(Q^1)(Q^2)$, and further more preferably *—CO—$(CH_2)_t$— where t is as defined above. Examples of the anion represented by formula (a2) include the following ones:

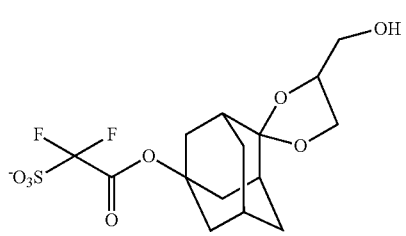

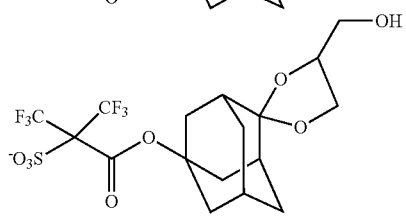

-continued
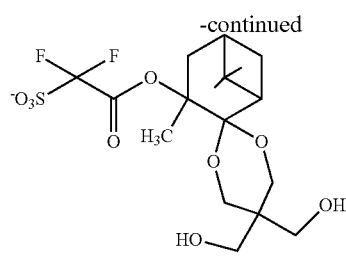
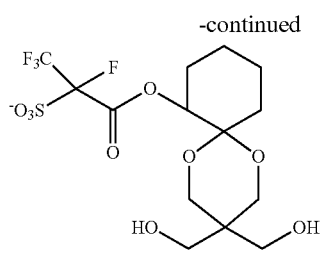
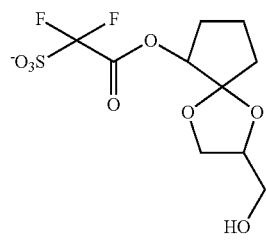
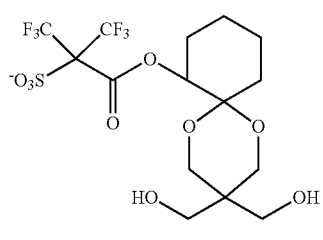
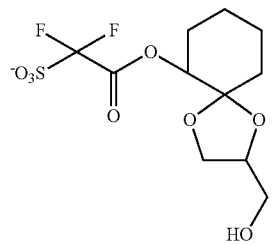
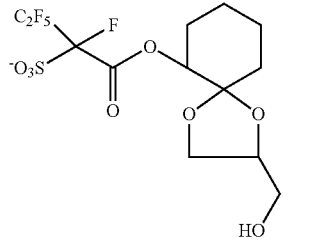
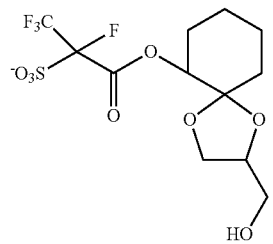
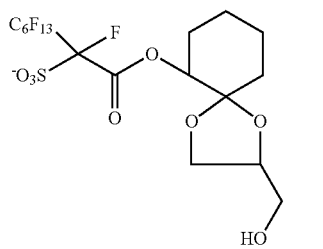
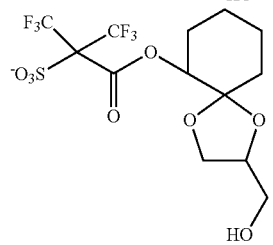
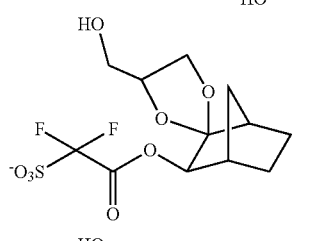
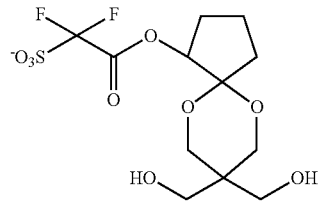
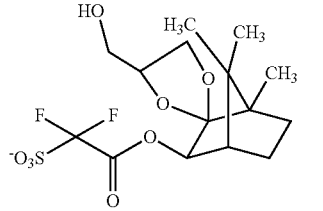
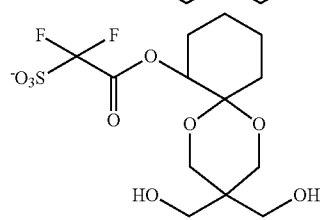
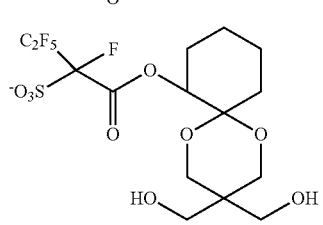

-continued
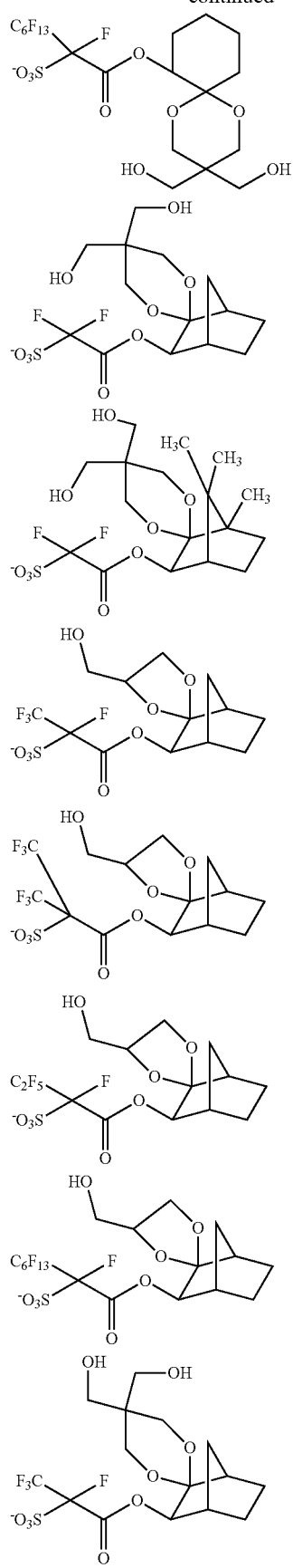
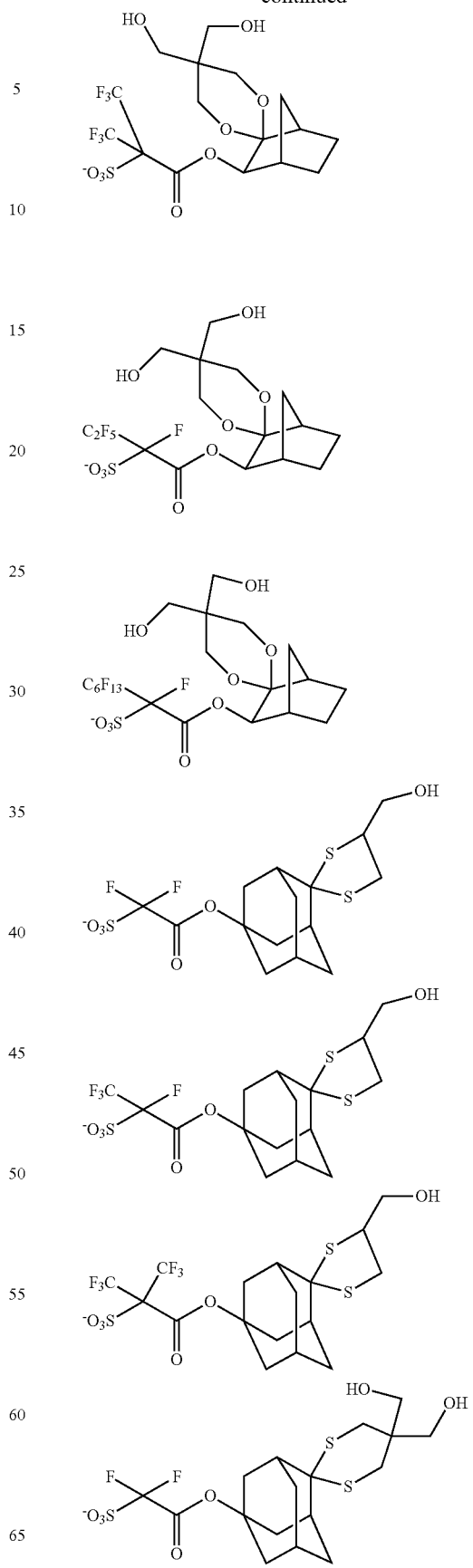

-continued
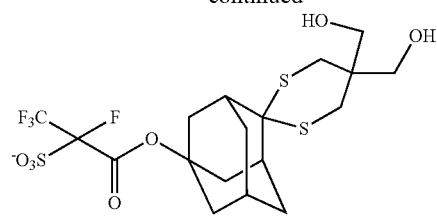
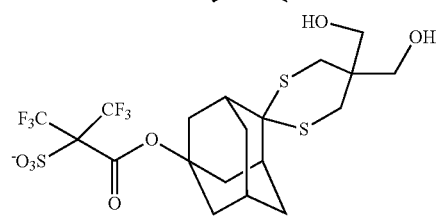
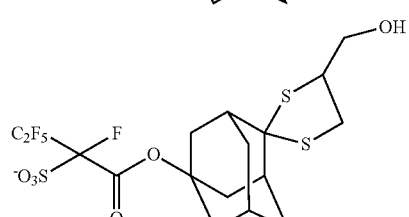
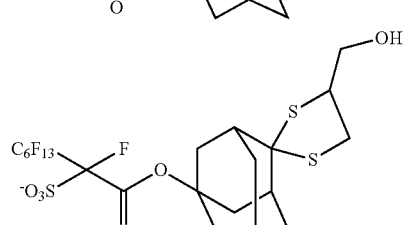
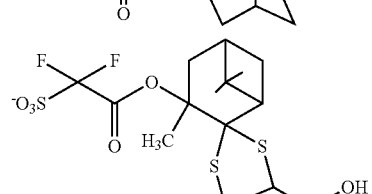
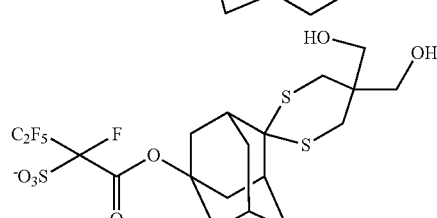
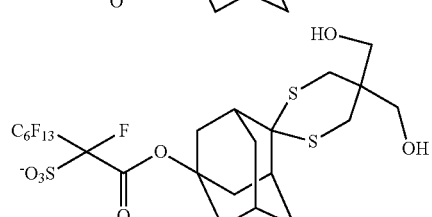
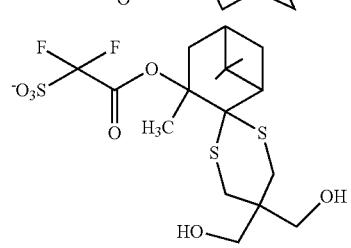
-continued
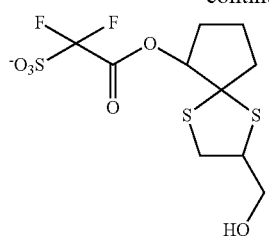
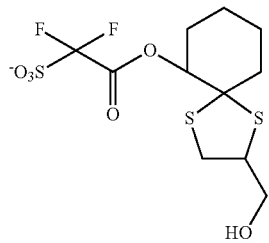
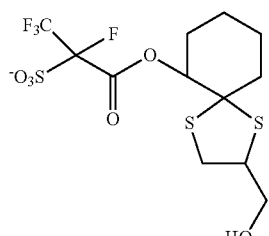
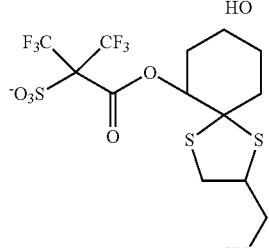
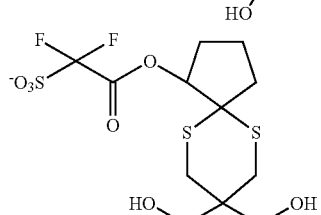
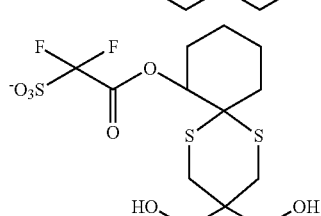
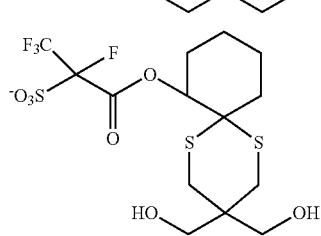

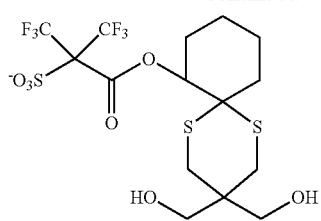
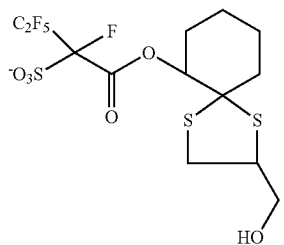
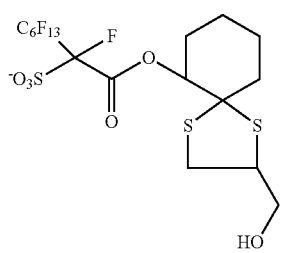
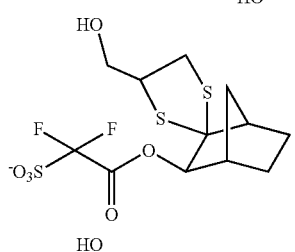
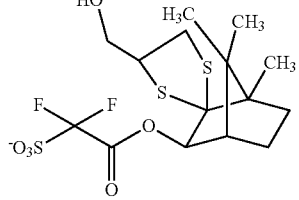
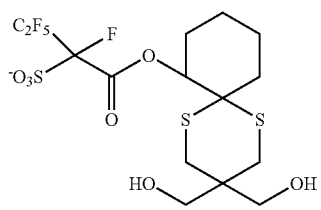
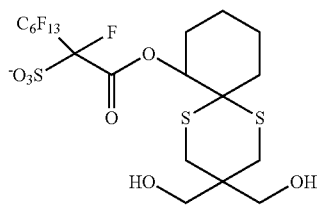
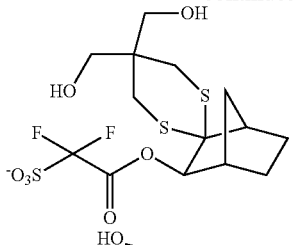
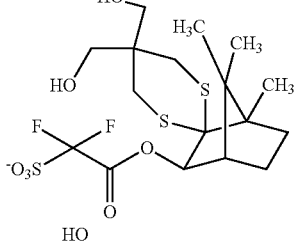
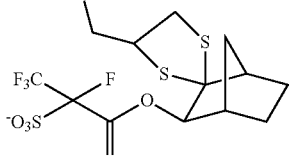
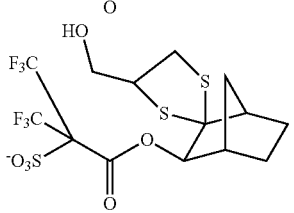
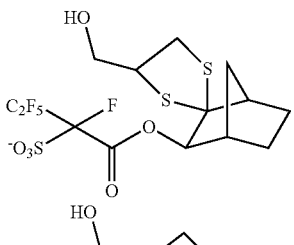
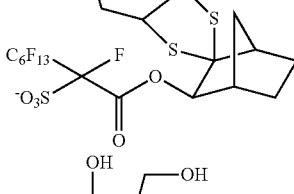
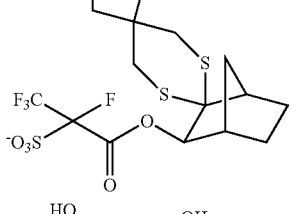
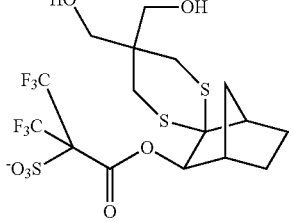

29
-continued
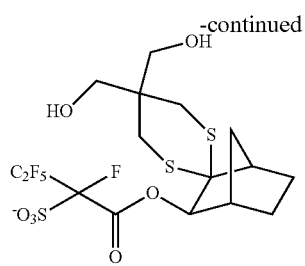
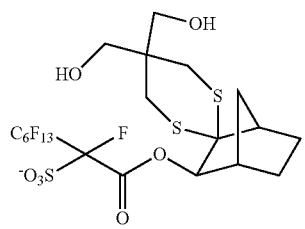
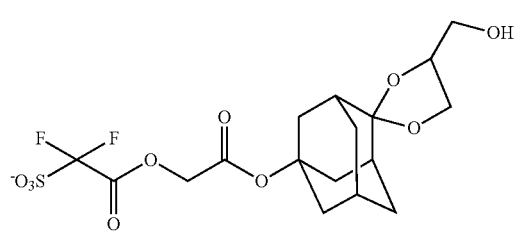
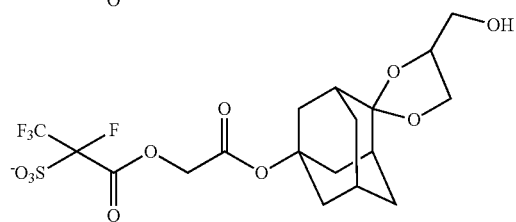
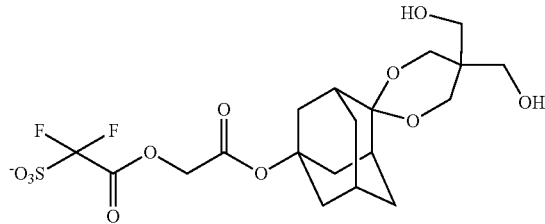
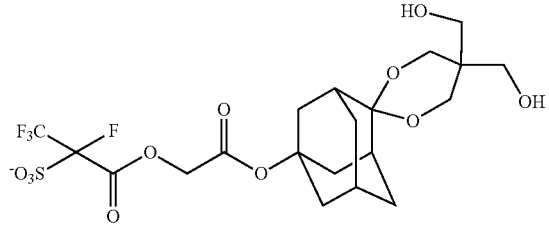
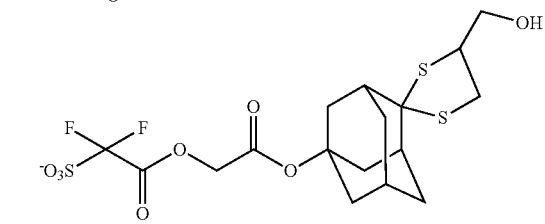
30
-continued
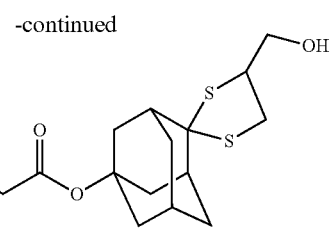
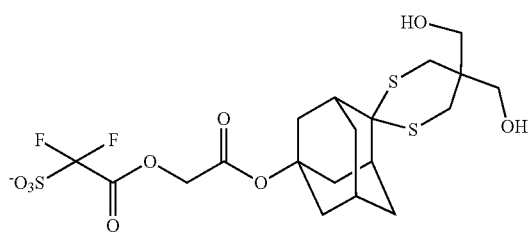
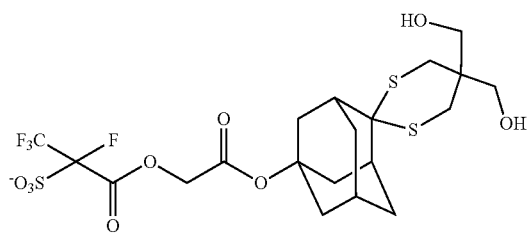
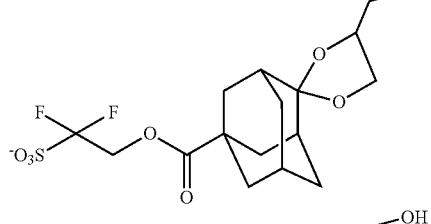
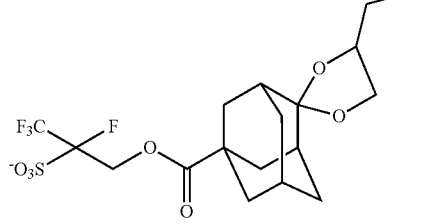
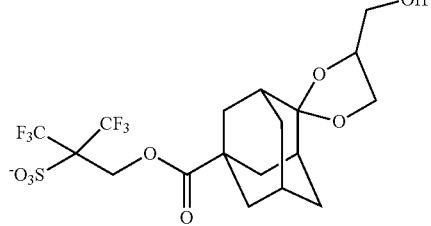
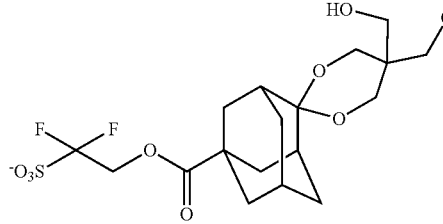

-continued

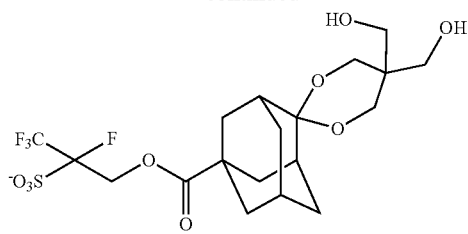

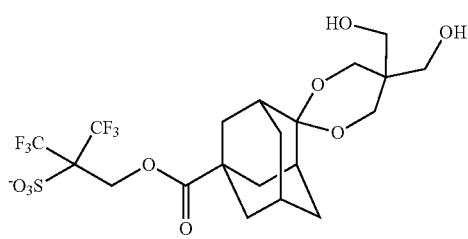

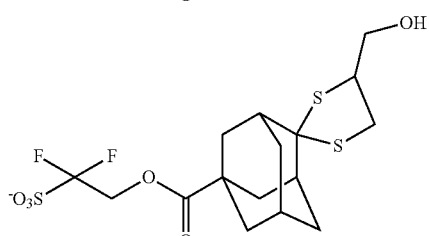

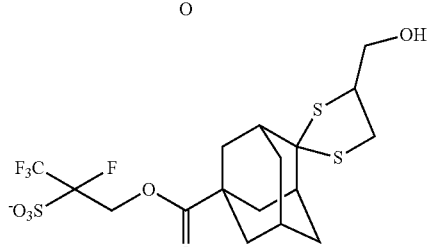

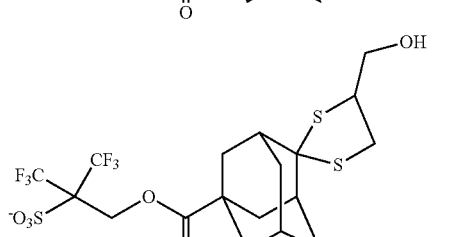

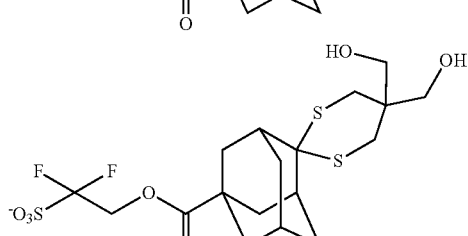

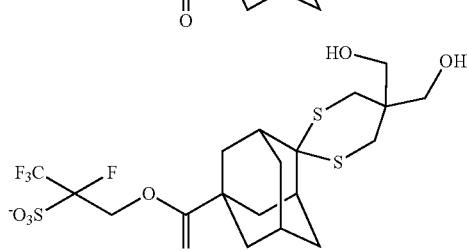

-continued

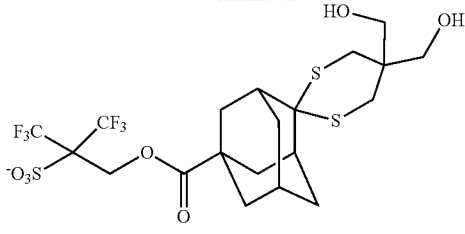

The cation for Salt (a) is preferably an organic cation.

Examples of the organic cation include an organic onium cation such as an organic sulfonium cation, an organic iodonium cation, an organic ammonium cation, an organic benzothiazolium cation and an organic phosphonium cation, and an organic sulfonium cation and an organic iodonium cation are preferred, and an organic sulfonium cation is more preferred.

Preferred examples of the organic cation include the organic cations represented by the formulae (b2-1), (b2-2), (b2-3) and (b2-4):

(b2-1)

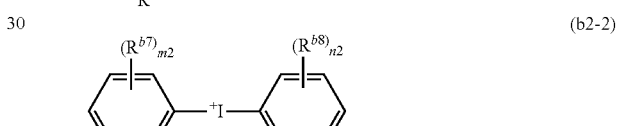
(b2-2)

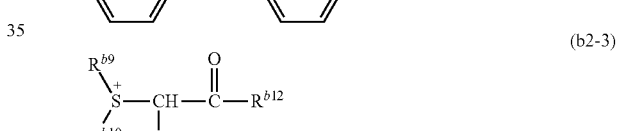
(b2-3)

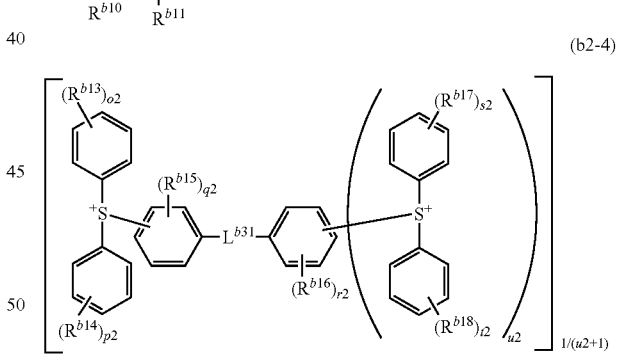
(b2-4)

In the formulae (b2-1) to (b2-4), $R^{b4}$, $R^{b5}$ and $R^{b6}$ independently represent a C1-C30 aliphatic hydrocarbon group, a C3-C36 alicyclic hydrocarbon group and a C6-C36 aromatic hydrocarbon group. The aliphatic hydrocarbon group can have a substituent selected from the group consisting of a hydroxy group, a C1-C12 alkoxy group, a C3-C12 alicyclic hydrocarbon group and a C6-C18 aromatic hydrocarbon group. The alicyclic hydrocarbon group can have a substituent selected from the group consisting of a halogen atom, a C1-C18 aliphatic hydrocarbon group, a C2-C4 acyl group and a glycidyloxy group. The aromatic hydrocarbon group can have a substituent selected from the group consisting of a halogen atom, a hydroxy group, a C1-C18 aliphatic hydrocarbon group and a C1-C12 alkoxy group.

$R^{b4}$ and $R^{b5}$ can be bonded to form a ring together with the adjacent $S^+$, and a methylene group in the ring may be replaced by —CO—, —O— or —SO—.

$R^{b7}$ and $R^{b8}$ are independently in each occurrence a hydroxy group, a C1-C12 alkyl group or a C1-C12 alkoxy group, m2 and n2 independently represents an integer of 0 to 5.

$R^{b9}$ and $R^{b10}$ independently represent a C1-C36 aliphatic hydrocarbon group or a C3-C36 alicyclic hydrocarbon group.

$R^{b9}$ and $R^{b10}$ can be bonded to form a ring together with the adjacent $S^+$, and a methylene group in the divalent acyclic hydrocarbon group may be replaced by —CO—, —O— or —SO—.

$R^{b11}$ represents a hydrogen atom, a C1-C36 aliphatic hydrocarbon group, a C3-C36 alicyclic hydrocarbon group or a C6-C18 aromatic hydrocarbon group.

$R^{b12}$ represents a C1-C12 aliphatic hydrocarbon group in which a hydrogen atom can be replaced by a C6-C18 aromatic hydrocarbon group, a C3-C18 saturated cyclic hydrocarbon group and a C6-C18 aromatic hydrocarbon group in which a hydrogen atom can be replaced by a C1-C12 alkoxy group or a (C1-C12 alkyl)carbonyloxy group.

$R^{b11}$ and $R^{b12}$ can be bonded each other to form a C1-C10 divalent acyclic hydrocarbon group which forms a 2-oxocycloalkyl group together with the adjacent —CHCO—, and a methylene group in the divalent acyclic hydrocarbon group may be replaced by —CO—, —O— or —SO—.

$R^{b13}$, $R^{b14}$, $R^{b15}$, $R^{b16}$, $R^{b17}$ and $R^{b18}$ independently represent a hydroxy group, a C1-C12 aliphatic hydrocarbon group or a C1-C12 alkoxy group.

$L^{b31}$ represents —S— or —O— and o2, p2, s2 and t2 each independently represents an integer of 0 to 5, q2 and r2 each independently represents an integer of 0 to 4, and u2 represents 0 or 1.

Preferred examples of the aliphatic hydrocarbon group represented by $R^{b4}$ to $R^{b12}$ include an alkyl group such as a methyl group, an ethyl group, a propyl group, an isopropyl group, 2,2-dimethylethyl group, 1-methylpropyl group, a 2-methylpropyl group, a 1,2-dimethylpropyl group, a 2,2-dimethylpropyl group, a 1-ethylpropyl group, a butyl group, a sec-butyl group, a tert-butyl group, a pentyl group, a 1-methylbutyl group, a 2-methylbutyl group, a 3-methylbutyl group, a hexyl group, a 1-propylbutyl group, a 1-methylpentyl group, a 2-ethylhexyl group, a 1,4-dimethylhexyl group, a 1-methylheptyl group, an octyl group, a decyl group, a dodecyl group, a hexadecyl group, a pentadecyl group, a heptadecyl group and an octadecyl group, and more preferred examples thereof include a methyl group, an ethyl group, a propyl group, an isopropyl group, a butyl group, a sec-butyl group, a tert-butyl group, a pentyl group, a hexyl group, an octyl group and a 2-ethylhexyl group. The aliphatic hydrocarbon group represented by $R^{b9}$, $R^{b10}$, $R^{b11}$ and $R^{b12}$ has preferably 1 to 12 carbon atoms, more preferably 4 to 12 carbon atoms.

The alicyclic hydrocarbon group may be monocyclic or polycyclic. Preferred examples thereof include a cycloalkyl group such as a cyclopentyl group, a cyclohexyl group, a methylcyclohexyl group, a dimethylcyclohexyl group, a cycloheptyl group and a cyclooctyl group, a group obtained by hydrogenating a condensed aromatic hydrocarbon group such as a hydronaphthyl group, a bridged cyclic hydrocarbon group such as an adamantyl group, a norbornyl group and a decahydronaphthyl group, and the following groups.

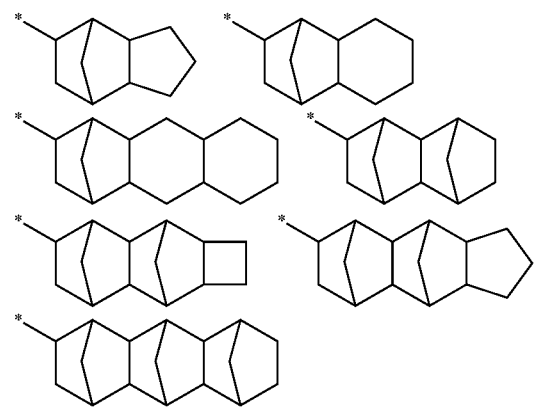

The alicyclic hydrocarbon group represented by $R^{b9}$, $R^{b10}$, $R^{b11}$ and $R^{b12}$ has preferably 3 to 18 carbon atoms, more preferably 4 to 12 carbon atoms.

Examples of the alicyclic hydrocarbon group in which a hydrogen atom has been replaced by an aliphatic hydrocarbon group include a methylcyclohexyl group, a dimethylcyclohexyl group, a methylnorbornyl group, and an isonorbornyl group.

The alicyclic hydrocarbon group in which a hydrogen atom has been replaced by an aliphatic hydrocarbon group has preferably 20 or less carbon atoms in total.

Examples of the aromatic hydrocarbon group include an aryl group such as a phenyl group, tolyl group, xylyl group, cumenyl group, mesityl group, p-ethylphenyl group, p-tert-butylphenyl group, p-adamantylphenyl group, a biphenylyl group, a naphthyl group, a phenanthryl group, a 2,6-diethylphenyl group, a 2-methyl-6-ethylphenyl group.

When the aromatic hydrocarbon group has an alicyclic hydrocarbon group or an aliphatic hydrocarbon group, it is preferred that the alicyclic hydrocarbon group and the aliphatic hydrocarbon group have respectively 1 to 18 carbon atoms and 3 to 18 carbon atoms.

Examples of the aromatic hydrocarbon group in which a hydrogen atom has been replaced by an alkoxy group include p-methoxyphenyl group.

Examples of the aliphatic hydrocarbon group in which a hydrogen atom has been replaced by an aromatic hydrocarbon group include a benzyl group, a phenethyl group, a phenylpropyl group, trityl group, naphthylmethyl group, and a naphthylethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the acyl group include an acetyl group, a propyonyl group and a butyryl group.

Examples of the halogen atom include a fluorine atom, a chlorine atom, a bromine atom and an iodine atom.

Examples of alkylcarbonyloxy group include a methyl carbonyloxy group, an ethylcarbonyloxy group, a n-propylcarbonyloxy group, an isopropylcarbonyloxy group, a n-butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethyl hexylcarbonyloxy group.

The ring group formed by bonding $R^{b4}$ and $R^{b5}$ together with the adjacent $S^+$ may be monocyclic or polycyclic, saturated or unsaturated, aromatic or nonaromatic group.

The ring is generally 3 to 12-membered one, preferably 3 to 7-membered one. Examples of the ring include the following ones.

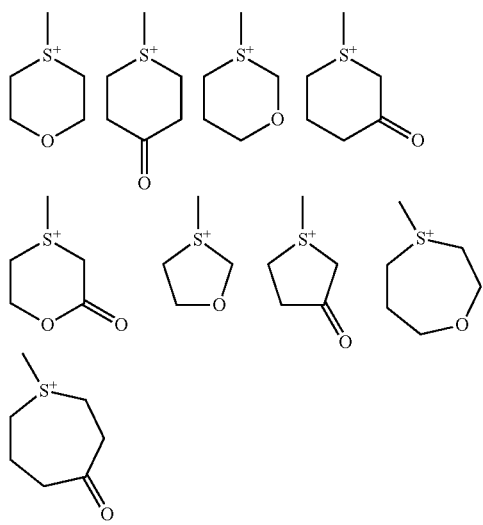

The ring group formed by bonding $R^{b9}$ and $R^{b10}$ together with the adjacent $S^+$ may be monocyclic or polycyclic, saturated or unsaturated, aromatic or nonaromatic group. The ring has generally C3-C12, preferably C3-C7 carbon atoms. Examples of the ring include a thiolan-1-ium ring (tetrahydrothiophenium ring), a thian-1-ium ring and a 1,4-oxathian-4-ium ring.

The ring group formed by bonding $R^{b11}$ and $R^{b12}$ together with —CH—CO— may be monocyclic or polycyclic, saturated or unsaturated, aromatic or nonaromatic group. The ring has generally C3-C12, preferably C3-C7 carbon atoms. Examples of the ring include an oxocycloheptane ring, an oxocyclohexane ring, an oxonorbornane ring, and an oxoadamantane ring.

Preferred examples of the cation for Salt (a) include an arylsulfonium cation, specifically cation of formula (b2-1), and more specifically a phenylsulfonium cation.

Examples of the cation represented by the formula (b2-1) include the following.

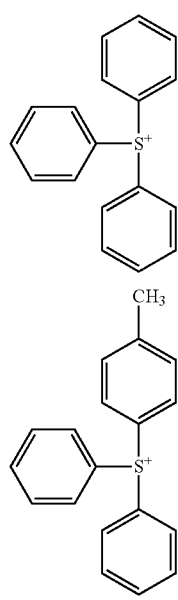

(b2-c-1)

(b2-c-2)

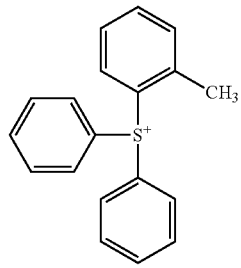

(b2-c-3)

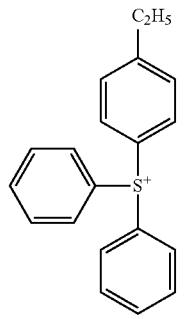

(b2-c-4)

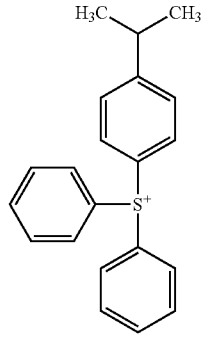

(b2-c-5)

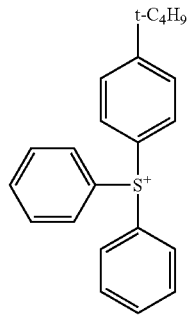

(b2-c-6)

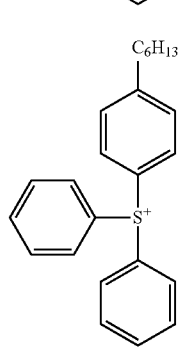

(b2-c-7)

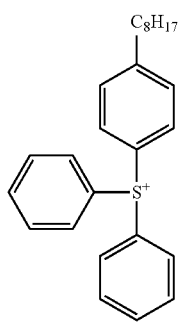 (b2-c-8)
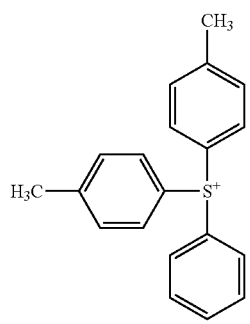 (b2-c-9)
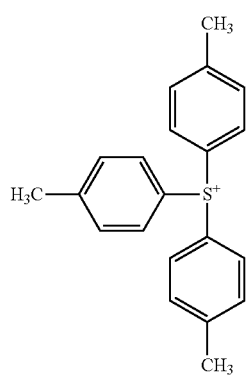 (b2-c-10)
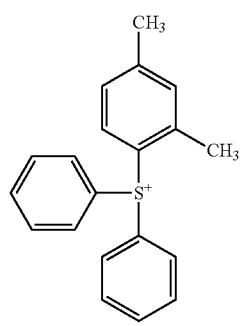 (b2-c-11)
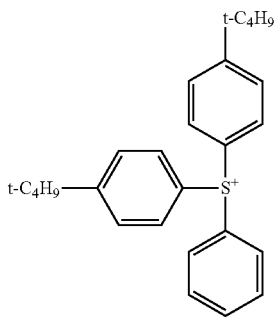 (b2-c-12)
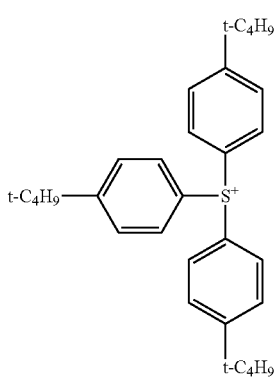 (b2-c-13)
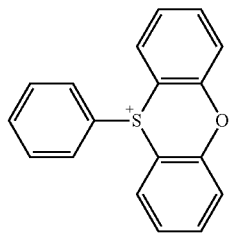 (b2-c-14)
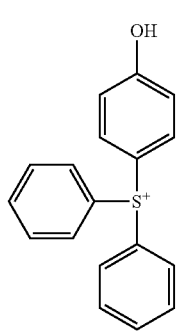 (b2-c-15)
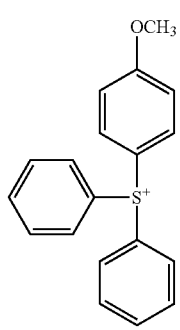 (b2-c-16)

(b2-c-17)
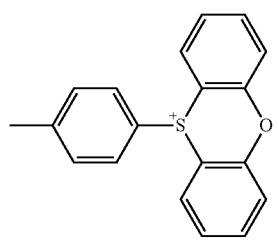
(b2-c-18)
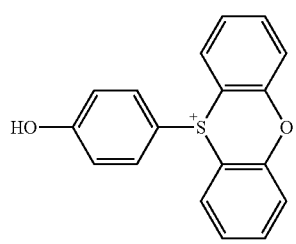
(b2-c-19)
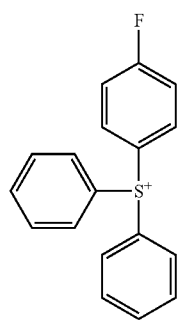
(b2-c-20)
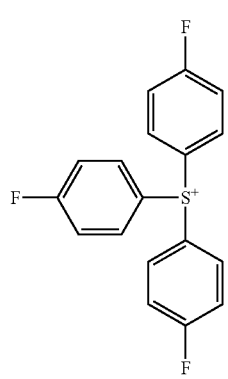
(b2-c-21)
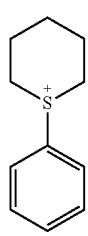
(b2-c-22)
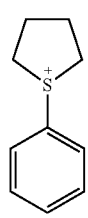
(b2-c-23)
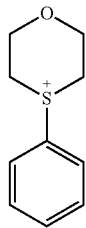
(b2-c-24)
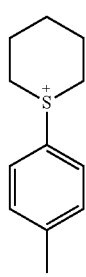
(b2-c-25)
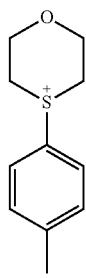
(b2-c-26)
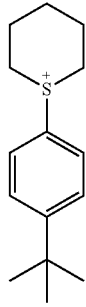
(b2-c-27)
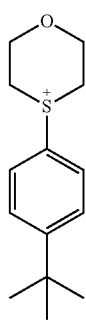

Examples of the cation represented by the formula (b2-2) include the followings.

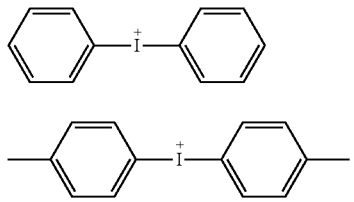
(b2-c-28)
(b2-c-29)
(b2-c-30)

Examples of the cation represented by the formula (b2-3) include the followings.

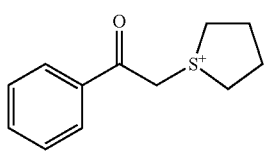
(b2-c-31)

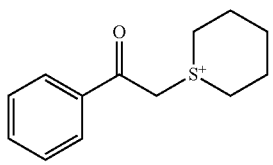
(b2-c-32)

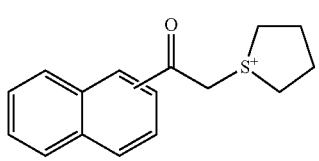
(b2-c-33)

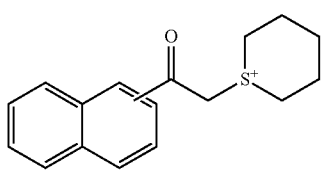
(b2-c-34)

Examples of the cation represented by the formula (b2-4) include the followings.

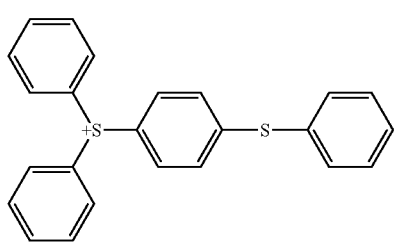
(b2-c-35)

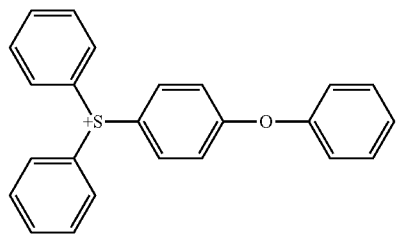
(b2-c-36)

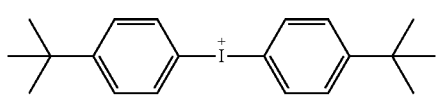
(b2-c-37)

(b2-c-38)

Salt (a) consists of any one of the above-mentioned cations and any one of the above-mentioned anions.

Specific examples of Salt (a) include the following ones.

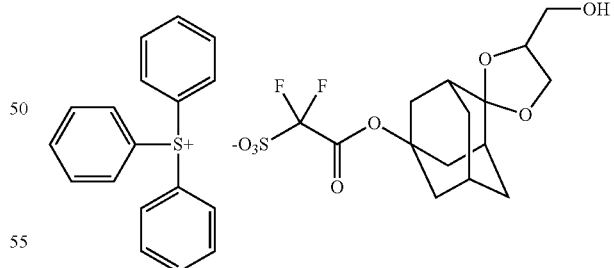
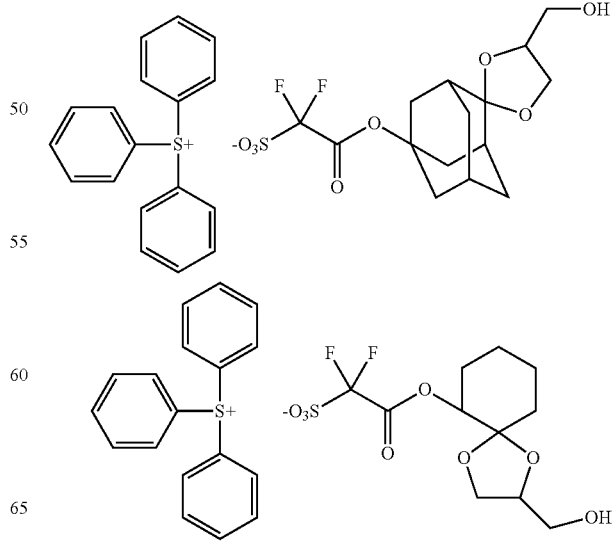

-continued
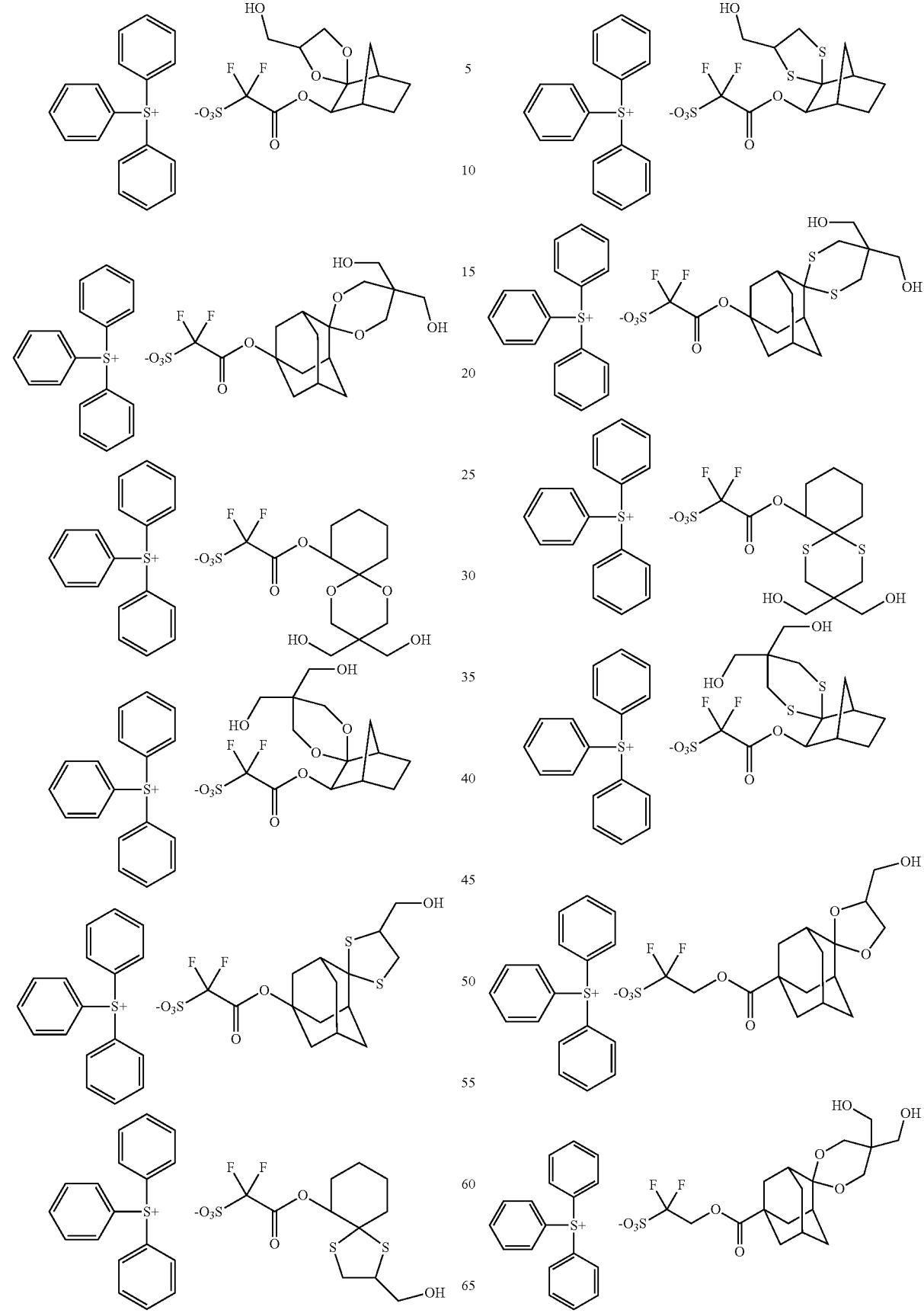

45
-continued
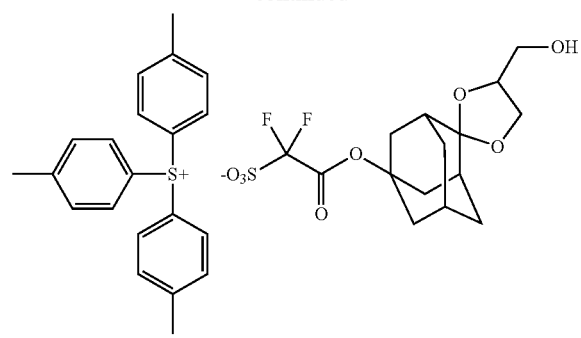
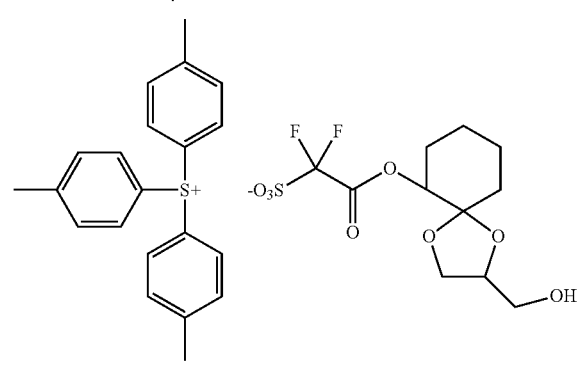
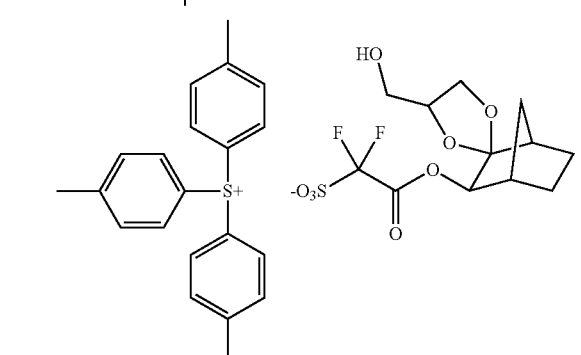
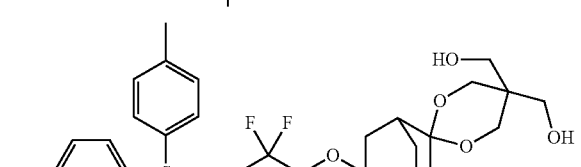
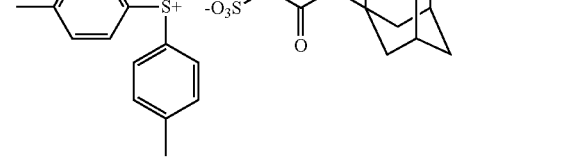
46
-continued
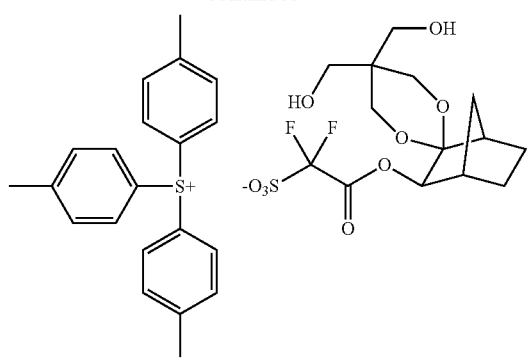
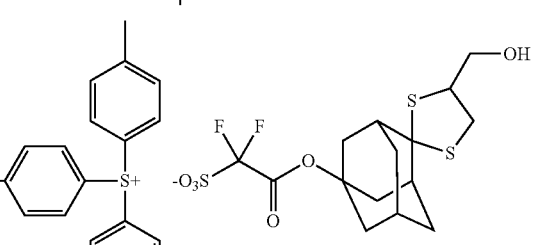
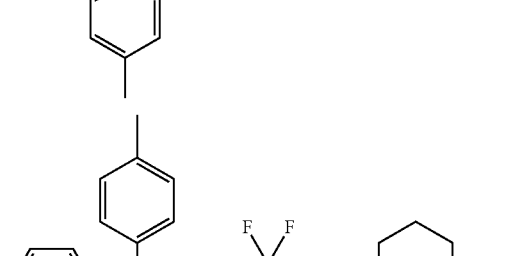
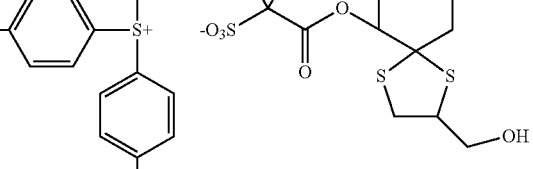
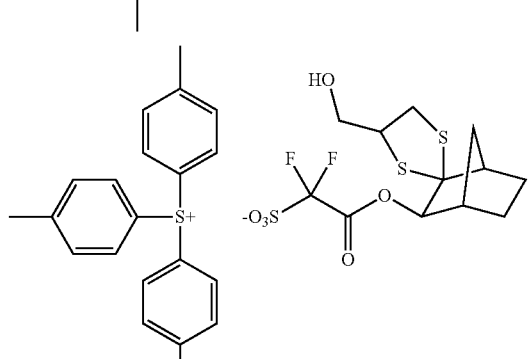
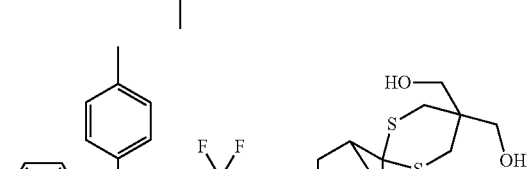
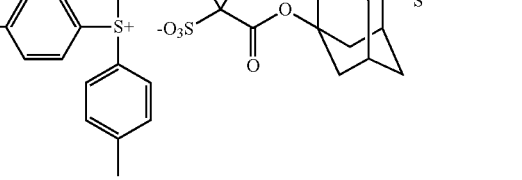

47
-continued
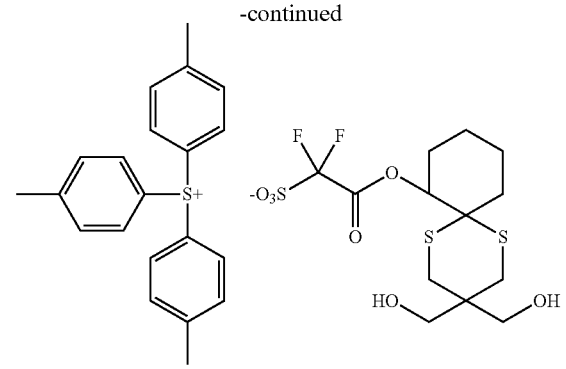
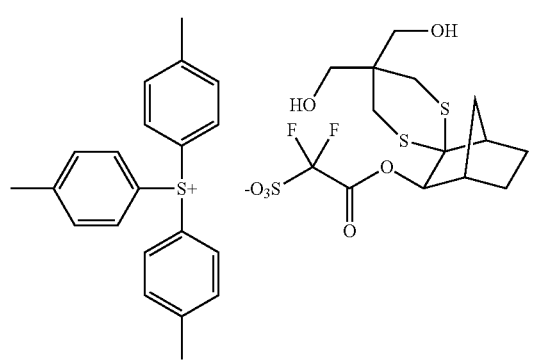
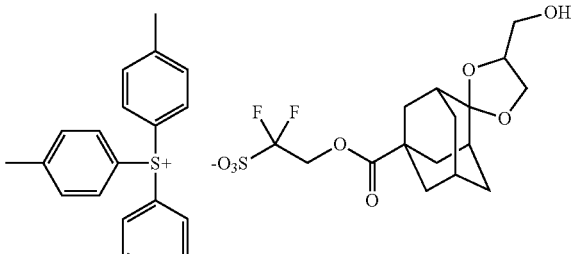
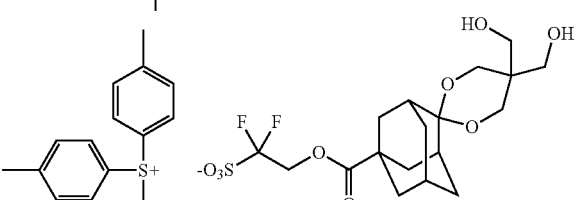
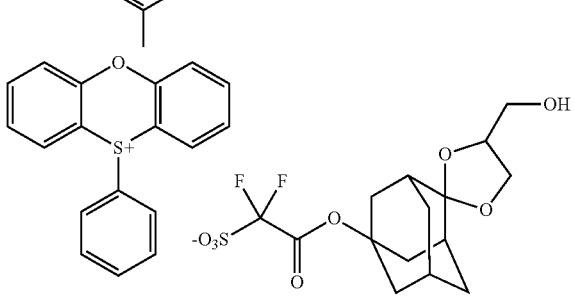
48
-continued
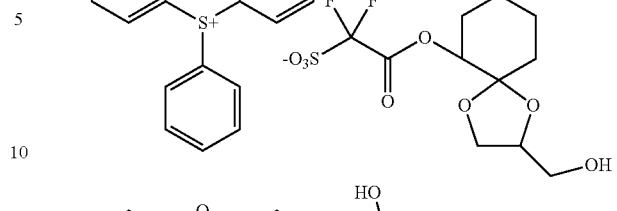
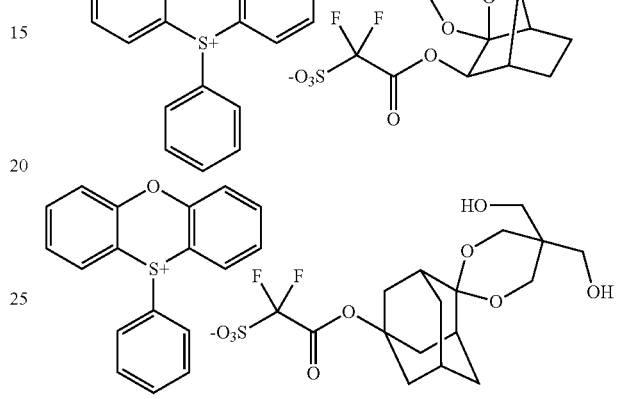
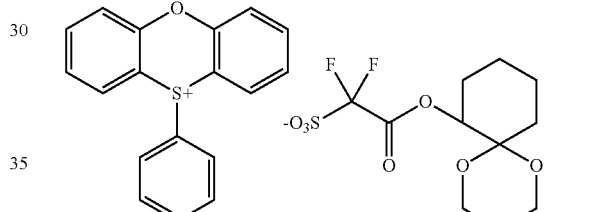
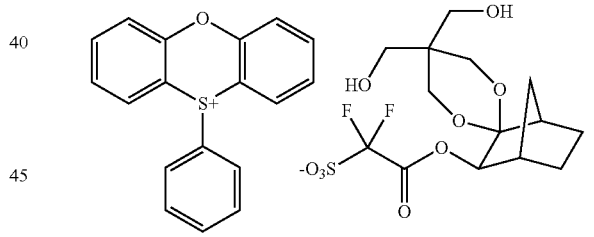
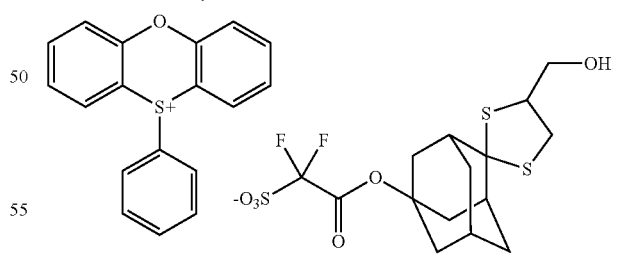
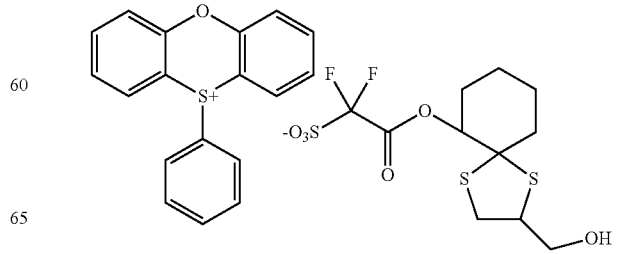

-continued
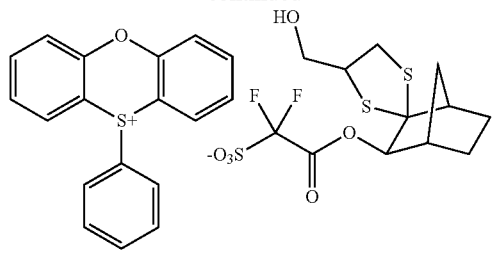
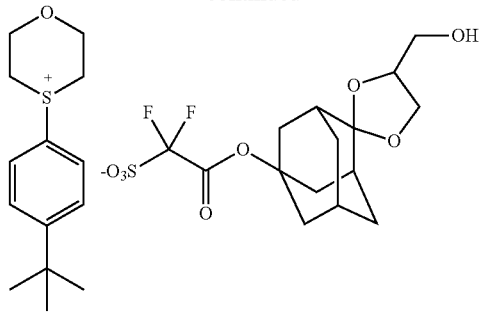
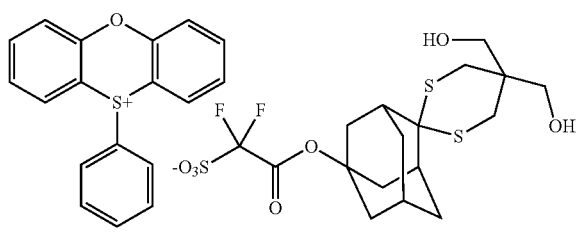
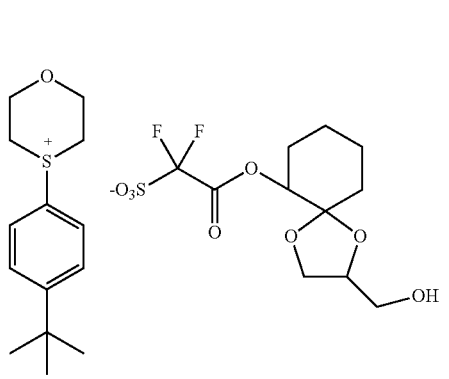
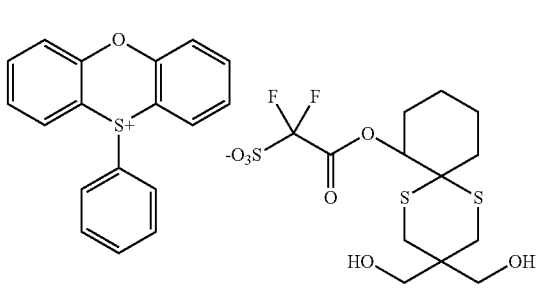
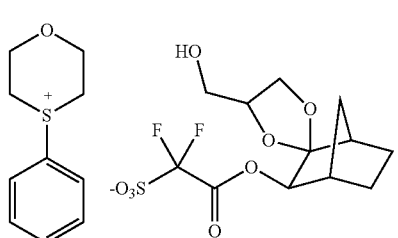
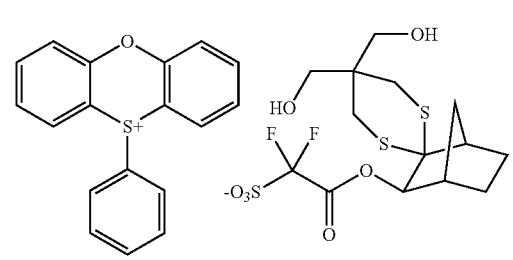
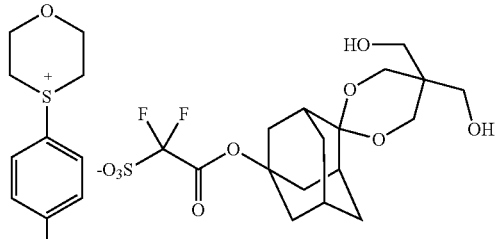
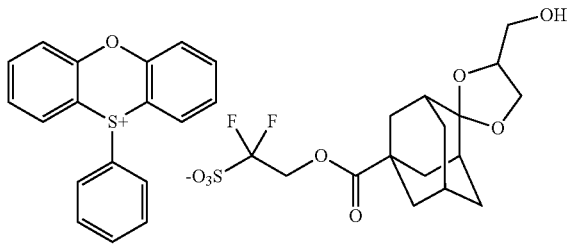
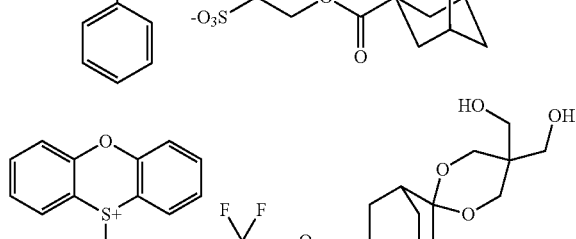
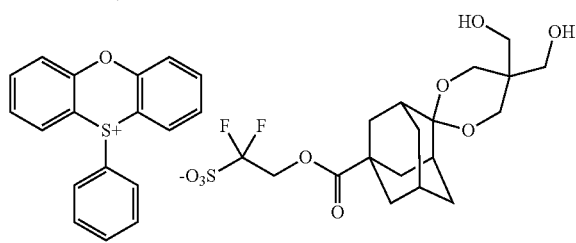
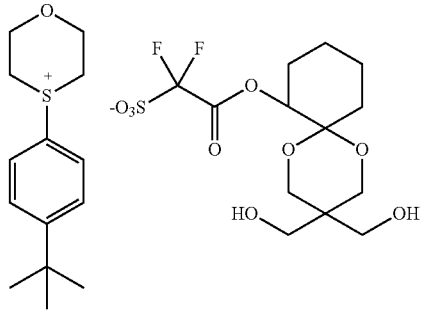

51
-continued
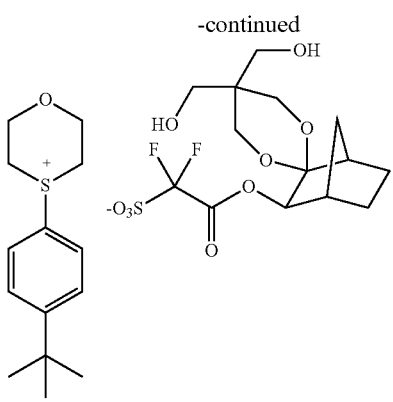
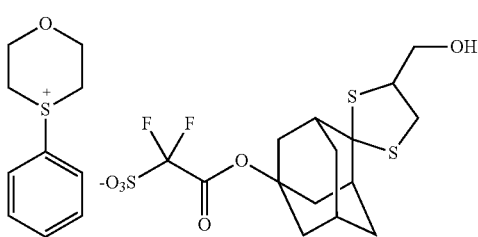
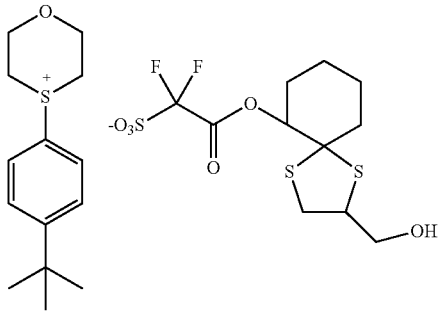
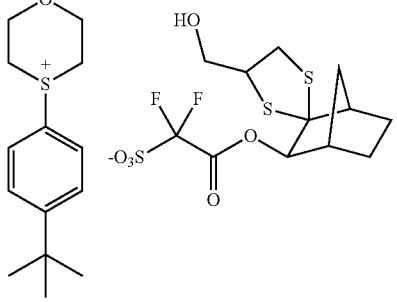
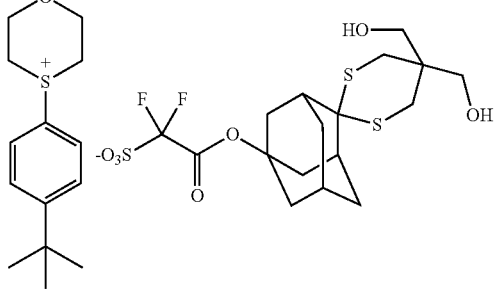
52
-continued
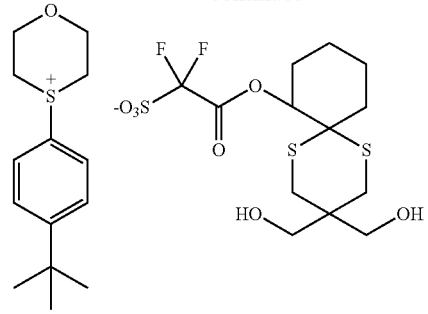
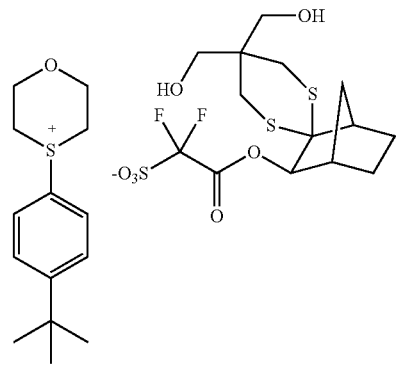
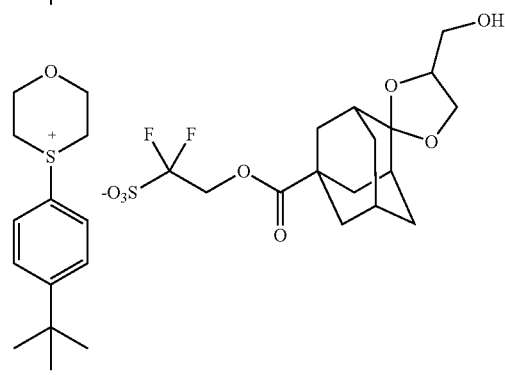
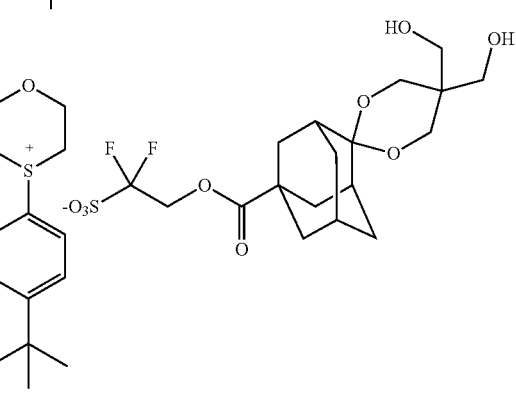
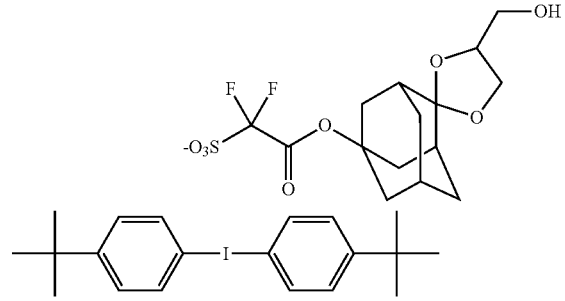

-continued
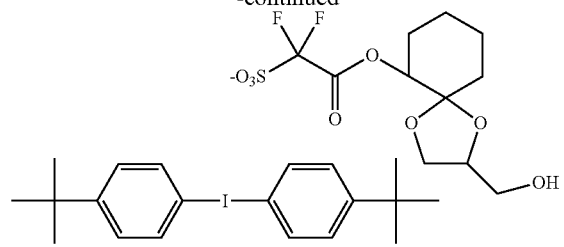
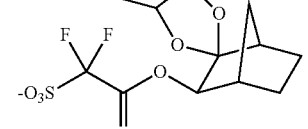
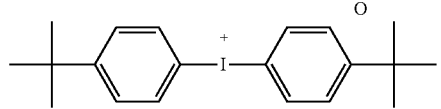
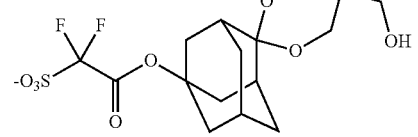
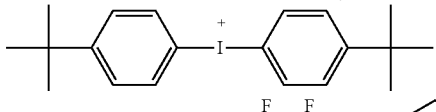
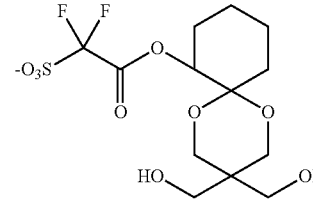
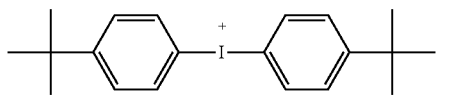
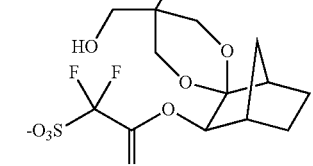
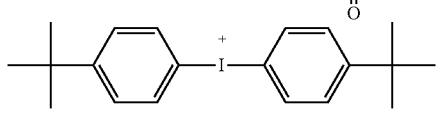
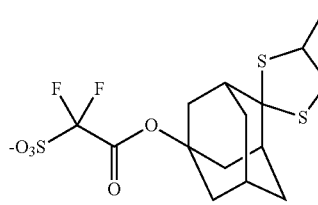
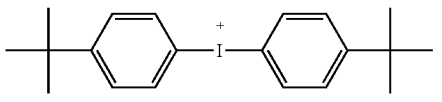
-continued
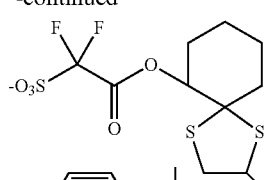
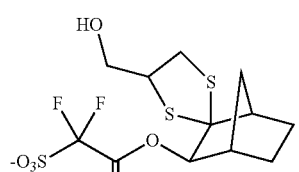
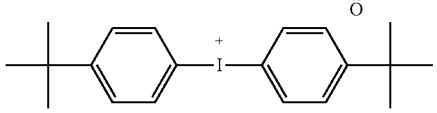
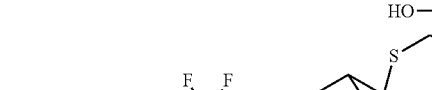
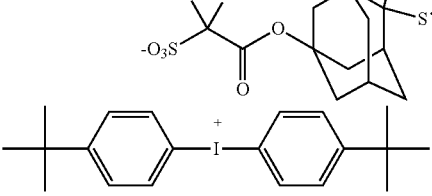
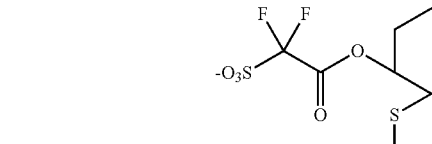
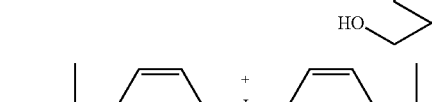
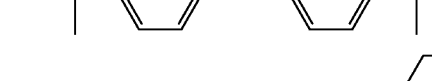
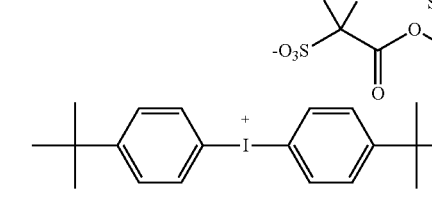
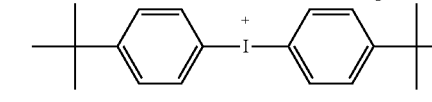

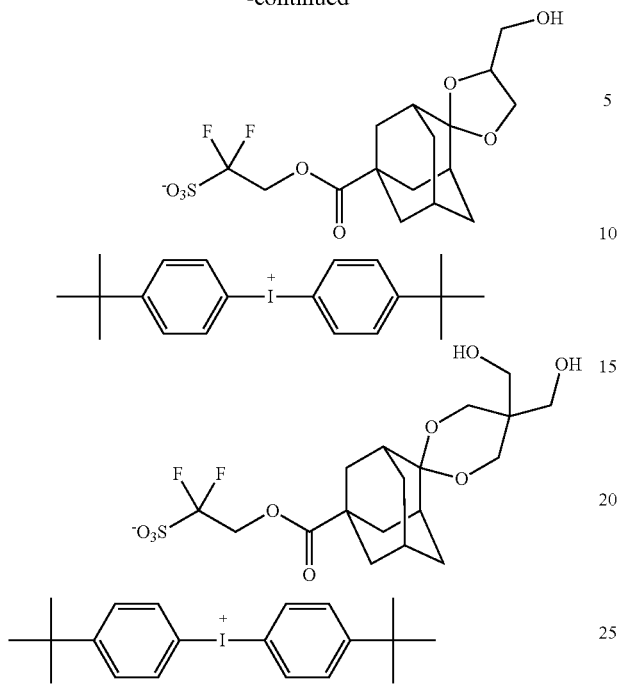

When Salt (a) consists of an organic cation and an anion represented by formula (a2), it can be produced by reacting a salt represented by formula (I-a) with a compound represented by formula (I-b), in the presence of an acid catalyst such as p-toluenesulfonic acid, in a solvent such as chloroform, acetonitrile or dimethylformamide:

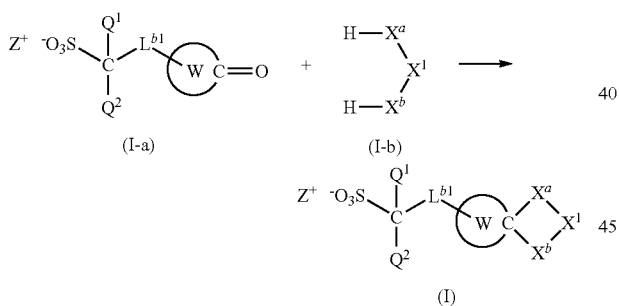

where $Q^1$, $Q^2$, $L^{b1}$, the ring W, $X^a$, $X^b$ and $X^1$ are the same as defined above, and $Z^+$ represents an organic cation.

The salt represented by formula (I-a) can be produced according to a method recited in JP2007-224008A1 or JP2012-224611A1. Examples of the salt represented by formula (I-a) include the following ones.

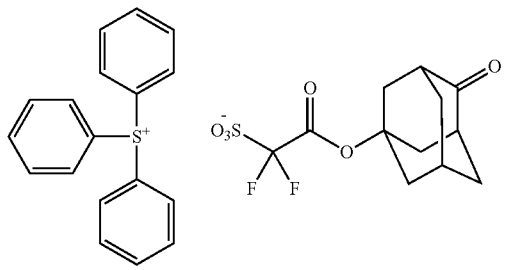

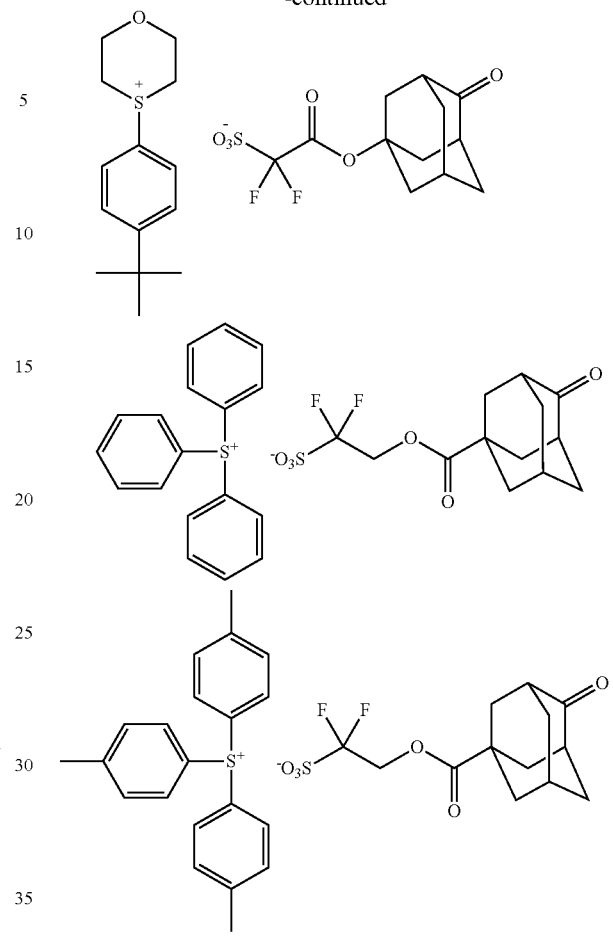

The compound represented by formula (I-b) is available on the market, examples of which include the following ones.

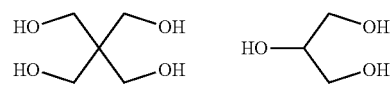 [SMILES: OCC(CO)(CO)CO ; OCC(O)CO]

<Acid Generator>

The acid generator of the present invention comprises Salt (a). The acid generator of the present invention can comprise two or more kinds of Salt (a).

The acid generator can comprise one or more known acid generators in addition to Salt (a).

The known acid generators may be an ionic acid generator or a nonionic acid generator, which are preferably an ionic acid generator.

Examples of the known acid generator include a salt which consists of an organic sulfonium and an organic sulfonic acid, and acid generators as mentioned in JP2013-68914A1, US2013/017501A1 and JP2013-11905A1.

Examples of the salt which consists of an organic sulfonium and an organic sulfonic acid include what consists of the cation represented by formula (b2-1) and a sulfonic acid represented by formula (B1):

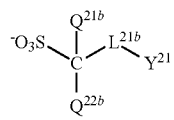
(B1)

wherein $Q^{21b}$ and $Q^{22b}$ independently each represent a fluorine atom or a C1-C6 perfluoroalkyl group;
$L^{21b}$ represents a C1-C24 divalent hydrocarbon group where a methylene group can be replaced by an oxygen atom or a carbonyl group and where a hydrogen atom can be replaced by a fluorine atom or a hydroxy group; and
$Y^{21}$ represents a methyl group or a C3-C18 alicyclic hydrocarbon group where a methylene group can be replaced by an oxygen atom, a carbonyl group or a sulfonyl group and where a hydrogen atom can be replaced by a substituent such as a fluorine atom or a hydroxy group.

Specific examples of the known acid generator include the following salts represented by formulae (B1-1) to (B1-28). Among them, those which comprise an arylsulfonium cation are preferred, the salts represented by formulae (B1-1), (B1-2), (B1-3), (B1-6), (B1-7), (B1-11), (B1-12), (B1-13), (B1-14), (B1-20), (B1-21), (B1-22), (B1-23), (B1-24), (B1-25) and (B1-26) are more preferred, and the salts represented by formulae (B1-1), (B1-2), (B1-3), (B1-6), (B1-7), (B1-11), (B1-12), (B1-13), (B1-14), (B1-20), (B1-21), (B1-23) and (B1-24) are still more preferred.

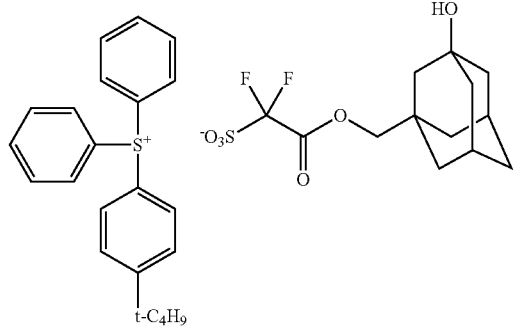
(B1-4)

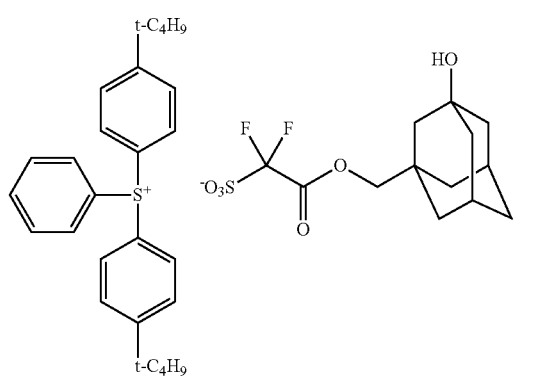
(B1-5)

(B1-1)
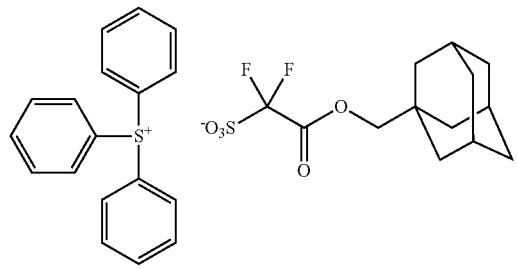

(B1-6)
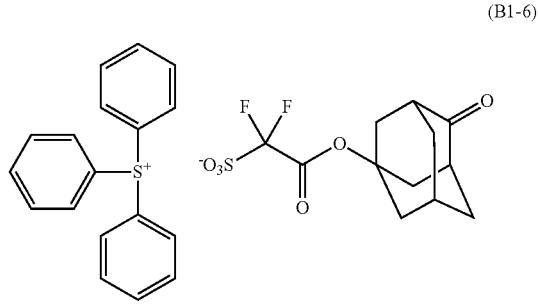

(B1-2)
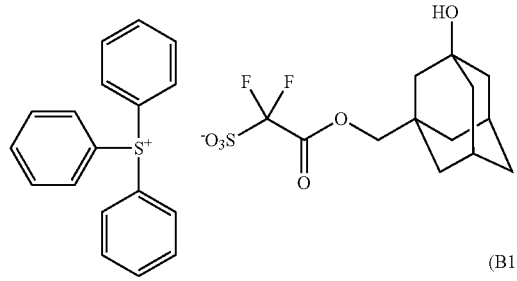

(B1-7)
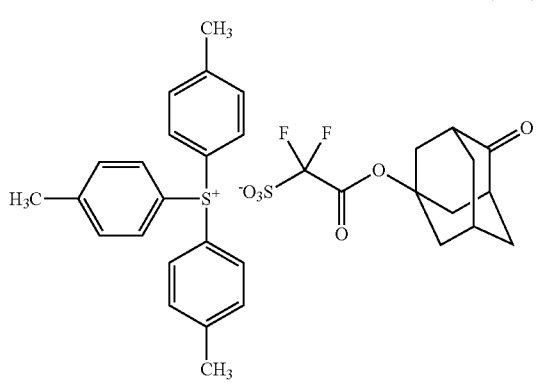

(B1-3)
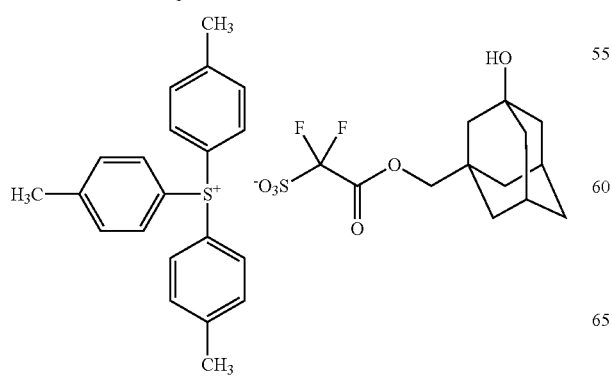

-continued
(B1-8)
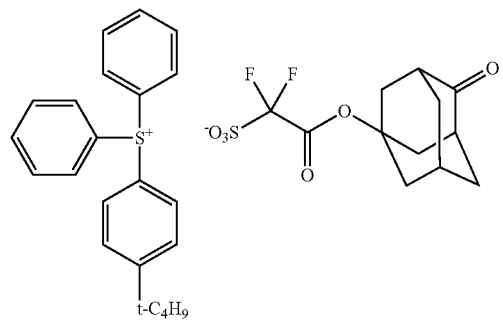
(B1-9)
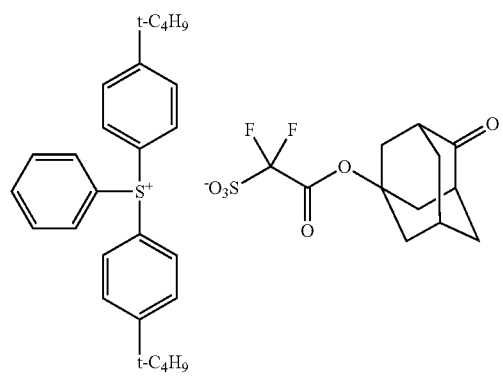
(B1-10)
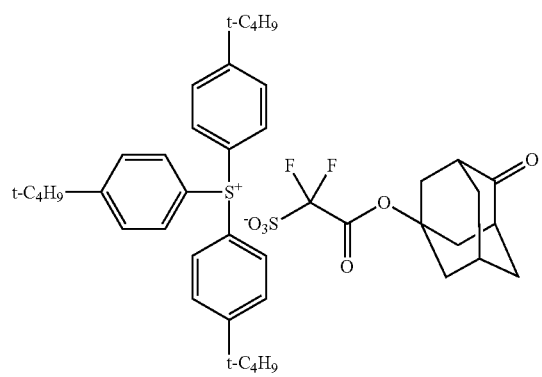
(B1-11)
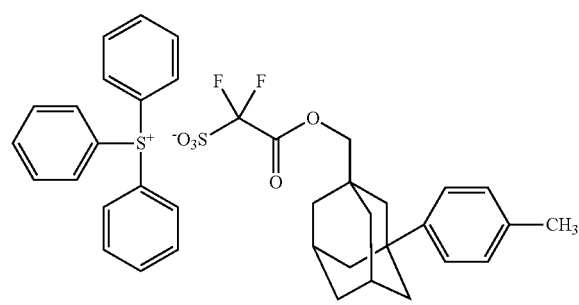
-continued
(B1-12)
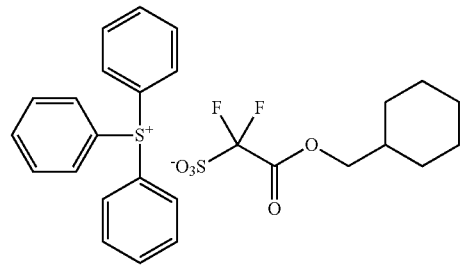
(B1-13)
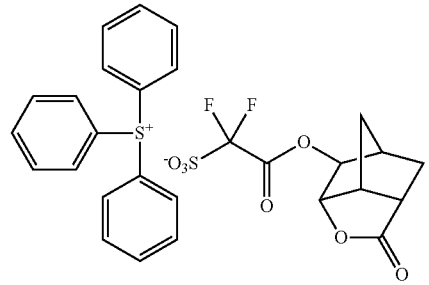
(B1-14)
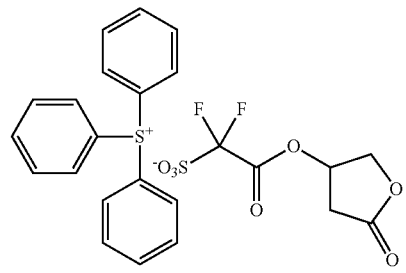
(B1-15)
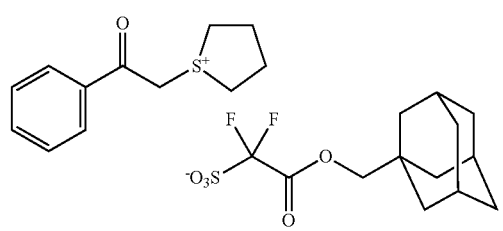
(B1-16)
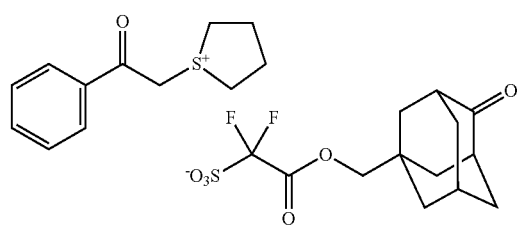
(B1-17)
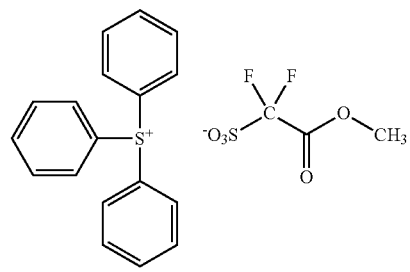

(B1-18)
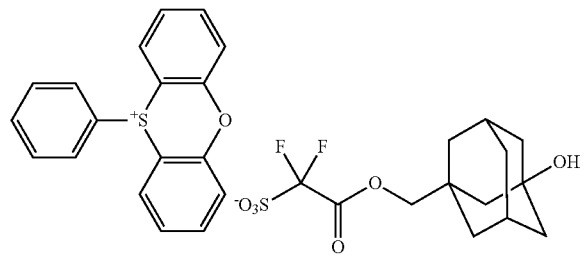
(B1-23)
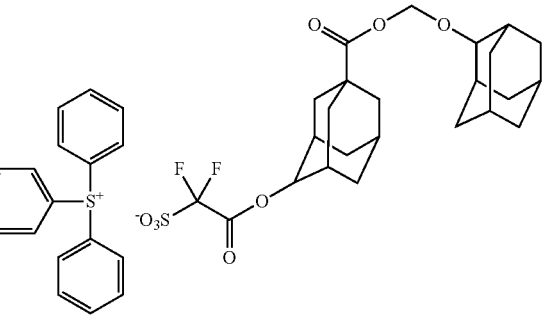
(B1-19)
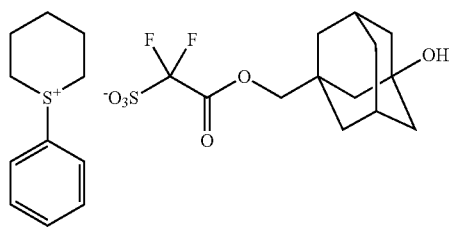
(B1-24)
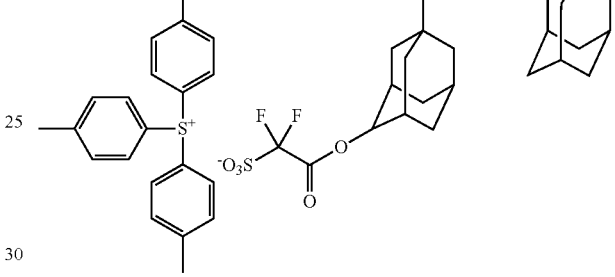
(B1-20)
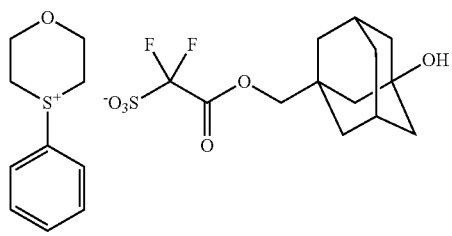
(B1-25)
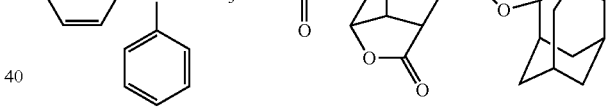
(B1-21)
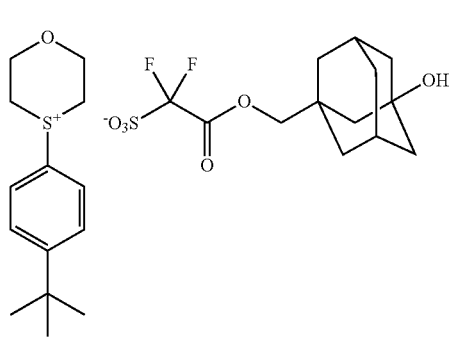
(B1-26)
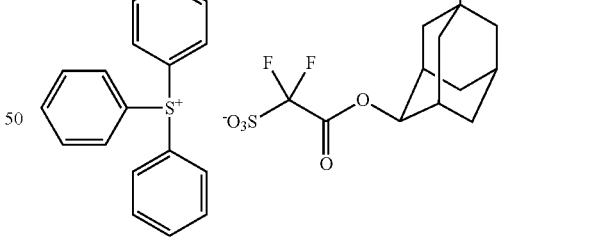
(B1-22)
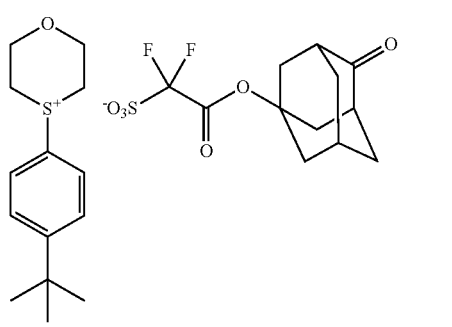
(B1-27)
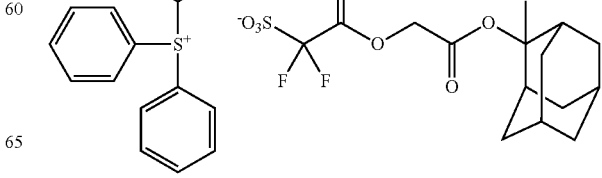

-continued (B1-28)

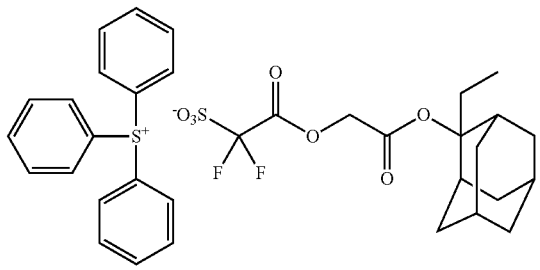

The acid generator of the present invention may consist of Salt (a). When the acid generator of the present invention comprises Salt (a) and the acid generator other than Salt (a), the weight ratio of Salt (a) and the other acids [=Salt (a): The other acids] is usually 1:99 to 100:0, preferably 1:99 to 99:1, more preferably 2:98 to 98:2, and still more preferably 5:95 to 95:5.

<Photoresist Composition>

The photoresist composition of the present invention comprises the acid generator and a resin having an acid-labile group which resin is sometimes referred to as "Resin (A)".

The photoresist composition may further comprise a basic compound or a solvent.

The basic compound is usually used as a quencher in the photoresist composition.

The photoresist composition comprises preferably a quencher, or a solvent, more preferably both of them.

The total content of the acid generator is preferably 1.5 parts by mass or more, more preferably 3 parts by mass or more, per 100 parts by mass of the resin. The content of the salt other than Salt (I) is preferably 40 parts by mass or less, more preferably 35 parts by mass or less, per 100 parts by mass of the resin.

<Resin (A)>

Resin (A) usually comprises a structural unit having an acid-labile group. Hereinafter, the structural unit is sometimes referred to as "structural unit (a1)".

Preferably Resin (A) further comprises another structural unit than the structural unit (a1), i.e. a structural unit having no acid-labile group, which is sometimes referred to as "structural unit (s)".

The structural unit (a1) is derived from a compound having an acid-labile group which compound is sometimes referred to as "Monomer (a1)".

Herein, "an acid-labile group" means a group which has a hydrophilic group, such as a hydroxy group or a carboxy group, resulting from removing a leaving group therefrom by the action of an acid.

For Resin (A), the acid-labile groups represented by formulae (1) and (2) are preferred:

(1)

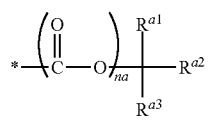

In formula (1), $R^{a1}$, $R^{a2}$ and $R^{a3}$ independently each represent a C1-C8 alkyl group, a C3-C20 alicyclic hydrocarbon group or a group consisting of them, and $R^{a1}$ and $R^{a2}$ can be bonded each other to form a C2-C20 divalent hydrocarbon group, na represents an integer of 0 or 1, and * represents a binding site.

(2)

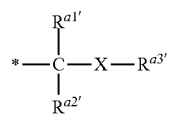

In formula (2), $R^{a1'}$ and $R^{a2'}$ independently each represent a hydrogen atom or a C1-C12 hydrocarbon group, and $R^{a3'}$ represents a C1-C20 hydrocarbon group, and $R^{a2'}$ and $R^{a3'}$ can be bonded each other to form a C2-C20 divalent hydrocarbon group, and one or more —CH$_2$— in the hydrocarbon group and the divalent hydrocarbon group can be replaced by —O— or —S—, X represents an oxygen atom or a sulfur atom, and * represents a binding site.

For $R^{a1}$, $R^{a2}$ and $R^{a3}$, specific examples of the alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, and the followings:

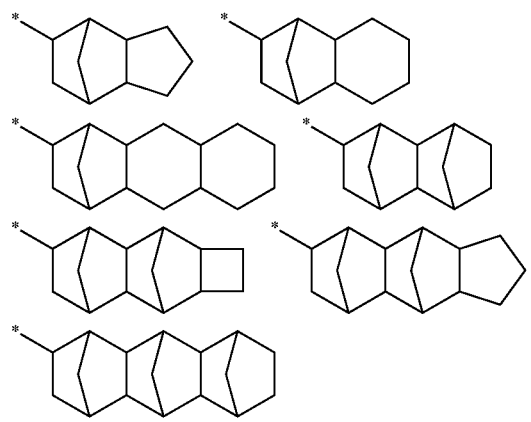

in which * represents a binding site.

The alicyclic hydrocarbon group preferably has 3 to 16 carbon atoms.

Examples of the group consisting of alkyl and alicyclic hydrocarbon group include a methylcyclohexyl group, a dimethylcyclohexyl group, a methylnorbornyl group, an adamantylmethyl group, and a norbornylethyl group.

The "na" is preferably 0.

When the divalent hydrocarbon group is formed by bonding $R^{a1}$ and $R^{a2}$ each other, examples of the moiety —C($R^{a1}$)($R^{a2}$)($R^{a3}$) include the following groups and the divalent hydrocarbon group preferably has 3 to 16 carbon atoms.

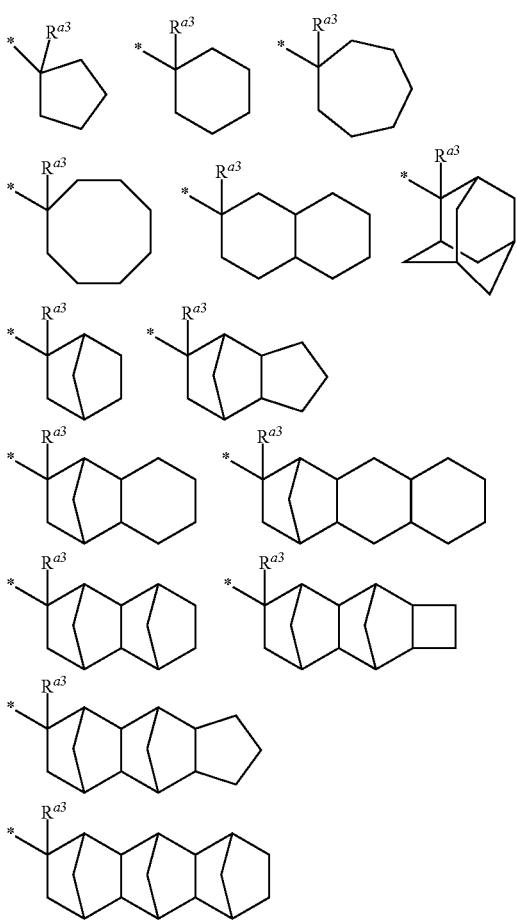

wherein $R^{a3}$ is the same as defined above and * represents a binding site.

The group represented by formula (1) wherein $R^{a1}$, $R^{a2}$ and $R^{a3}$ independently each represent a C1-C8 alkyl group such as a tert-butyl group, the group represented by formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferred.

For formula (2), examples of the hydrocarbon group include an alkyl group, an alicyclic hydrocarbon group, an aromatic hydrocarbon group and a group consisting of two or more of them.

Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

Examples of the divalent hydrocarbon group formed by bonding $R^{a2'}$ and $R^{a3'}$ each other include those formed by removing a hydrogen atom from the hydrocarbon group represented by $R^{a1'}$, $R^{a2'}$ and $R^{a3'}$.

It is preferred that at least one of $R^{a1'}$ and $R^{a2'}$ is a hydrogen atom.

Examples of the group represented by formula (2) include the following.

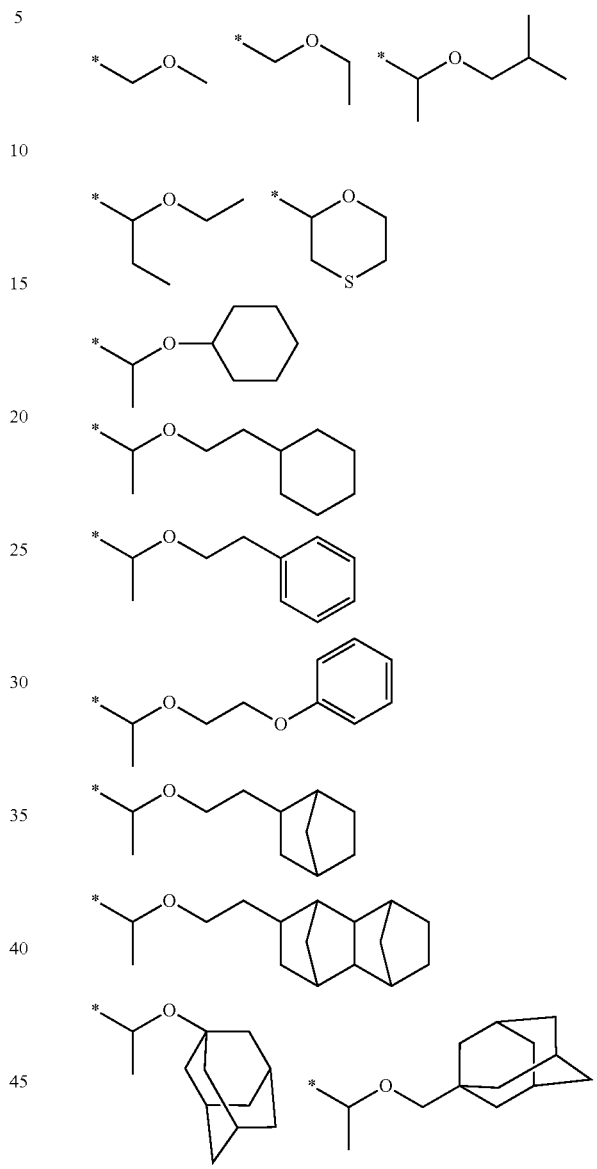

Monomer (a1) is preferably a monomer having an acid-labile group in its side chain and an ethylenic unsaturated group, more preferably a (meth)acrylate monomer having an acid-labile group in its side chain, and still more preferably a (meth)acrylate monomer having the group represented by formula (1) or (2).

The (meth)acrylate monomer having an acid-labile group in its side chain is preferably those which comprise a C5-C20 alicyclic hydrocarbon group. The resin which comprises a structural unit derived from such monomers can provide improved resolution for a photoresist pattern to be prepared therefrom.

The structural unit derived from a (meth)acrylate monomer having the group represented by formula (1) is preferably one of structural units represented by formulae (a1-0), (a1-1) and (a1-2).

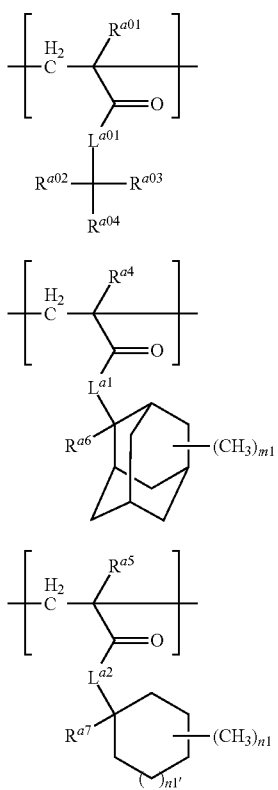

(a1-0)

(a1-1)

(a1-2)

In each formula, $L^{a01}$, $L^{a1}$ and $L^{a2}$ each independently represent —O— or *—O—(CH$_2$)$_{k1}$—CO—O— in which k1 represents an integer of 1 to 7 and * represents a binding site to —CO—, $R^{a01}$, $R^{a4}$ and $R^{a5}$ each independently represent a hydrogen atom or a methyl group, $R^{a02}$, $R^{a03}$, $R^{a04}$, $R^{a6}$ and $R^{a7}$ each independently represent a C1-C8 alkyl group, a C3-C18 alicyclic hydrocarbon group, or a group formed by combining them, m1 represents an integer of 0 to 14, n1 represents an integer of 0 to 10, and n1' represents an integer of 0 to 3.

Hereinafter, the structural units represented by formulae (a1-0), (a1-1) and (a1-2) are respectively referred to as "structural unit (a1-0)", "structural unit (a1-1)" and "structural unit (a1-2)". Resin (A) may comprise two or more of Such structural units.

$L^{a01}$ is preferably *—O— or *—O—(CH$_2$)$_{f1}$—CO—O— in which * represents a binding site to —CO—, and f1 represents an integer of 1 to 4, and is more preferably *—O— or *—O—CH$_2$—CO—O—, and is especially preferably *—O—.

$R^{a01}$ is preferably a methyl group.

For $R^{a02}$, $R^{a03}$ and $R^{a04}$, examples of the alkyl group, the alicyclic hydrocarbon group and the group formed by combining them include the same as referred for $R^{a1}$, $R^{a2}$ and $R^{a3}$.

The alkyl group preferably has 1 to 6 carbon atoms.

The alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

The group formed by combining them preferably has 18 carbon atoms or less in total, examples of which include a methylcyclohexyl group, a dimethylcyclohexyl group, and a methylnorbornyl group. Each of $R^{a02}$ and $R^{a03}$ is preferably a C1-C6 alkyl group, more preferably a methyl group and an ethyl group.

$R^{a04}$ is preferably a C1-C6 alkyl group and a C5-012 alicyclic hydrocarbon group, more preferably a methyl group, an ethyl group, a cyclohexyl group, and an adamantyl group.

Each of $L^{a1}$ and $L^{a2}$ is preferably *—O— or *—O—(CH$_2$)$_{f1}$—CO—O— in which * represents a binding site to —CO—, and f1 is the same as defined above, and is more preferably *—O— or *—O—CH$_2$—CO—, and is especially preferably *—O—.

Each of $R^{a4}$ and $R^{a5}$ is preferably a methyl group.

For $R^{a6}$ and $R^{a7}$, examples of the alkyl group include a methyl group, an ethyl group, a propyl group, an isopropyl group, a butyl group, a tert-butyl group, a pentyl group, a heptyl group, a 2-ethylheptyl group and an octyl group.

For $R^{a6}$ and $R^{a7}$, examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic alicyclic hydrocarbon group such as a decahydronaphthyl group, an adamantyl group, a norbornyl group, a methylnorbornyl group and the following. For $R^{a6}$ and $R^{a7}$, examples of the group consisting of an alkyl group and an alicyclic hydrocarbon group include an aralkyl group such as a benzyl group, and a phenethyl group.

The alkyl group represented by $R^{a6}$ and $R^{a7}$ is preferably a C1-C6 alkyl group.

The alicyclic hydrocarbon group represented by $R^{a6}$ and $R^{a7}$ is preferably a C3-C8 alicyclic hydrocarbon group, more preferably a C3-C6 alicyclic hydrocarbon group.

The "m1" is preferably an integer of 0 to 3, and is more preferably 0 or 1.

The "n1" is preferably an integer of 0 to 3, and is more preferably 0 or 1.

The "n1'" is preferably 0 or 1.

Examples of the structural unit (a1-0) include those represented by formulae (a1-0-1) to (a1-0-12), preferably those represented by formulae (a1-0-1) to (a1-0-10).

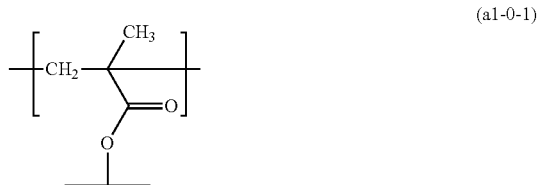

(a1-0-1)

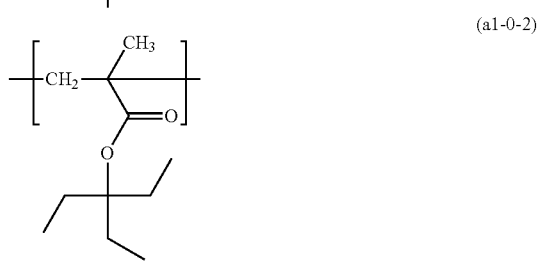

(a1-0-2)

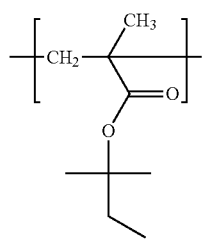 (a1-0-3)
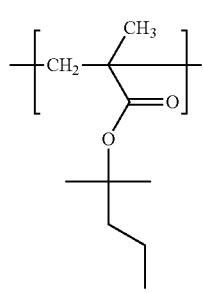 (a1-0-4)
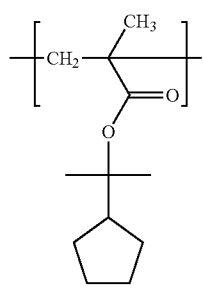 (a1-0-5)
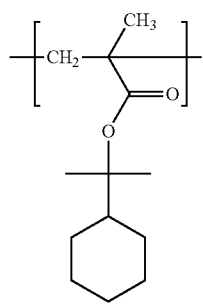 (a1-0-6)
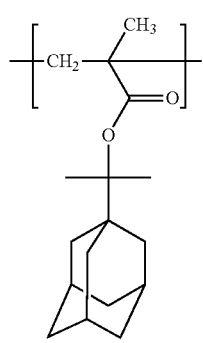 (a1-0-7)
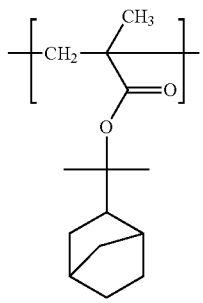 (a1-0-8)
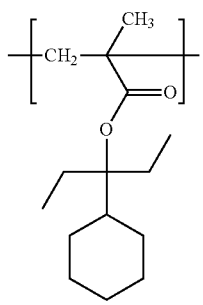 (a1-0-9)
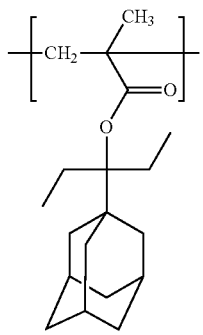 (a1-0-10)
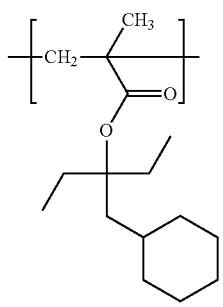 (a1-0-11)
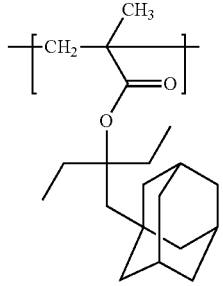 (a1-0-12)
Examples of the structural unit (a1-0) further include such groups that a methyl group has been replaced by a hydrogen atom in any one of formulae (a1-0-1) to (a1-0-12).

Examples of the monomer from which the structural unit (a1-1) is derived include the monomers described in JP2010-204646A1, and the following monomers represented by the formulae (a1-1-1) to (a1-1-8), preferably the following monomers represented by the formulae (a1-1-1) to (a1-1-4).

(a1-1-1)
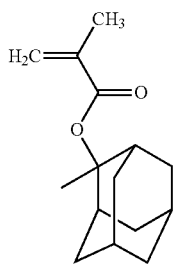

(a1-1-2)
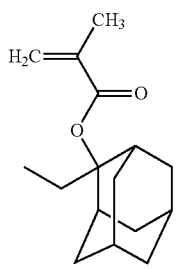

(a1-1-3)
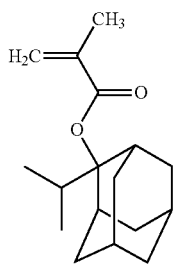

(a1-1-4)
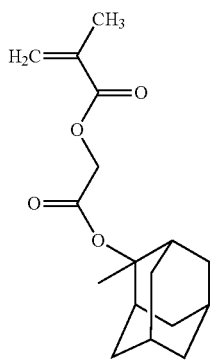

(a1-1-5)
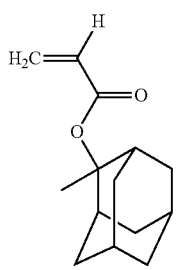

(a1-1-6)
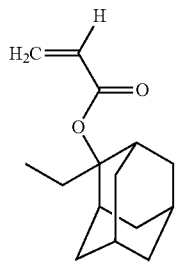

(a1-1-7)
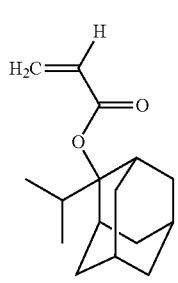

(a1-1-8)
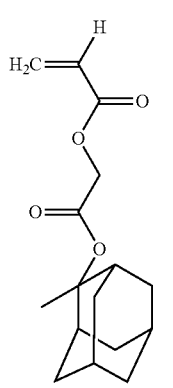

Examples of the monomer from which the structural unit (a1-2) is derived include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate, preferably the monomers represented by formulae (a1-2-1) to (a1-2-12), more preferably the monomers represented by formulae (a1-2-3), (a1-2-4), (a1-2-9) and (a1-2-10), still more preferably the monomers represented by formulae (a1-2-3) and (a1-2-9).

(a1-2-1)
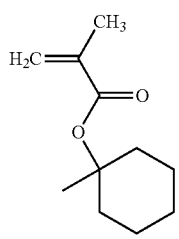

(a1-2-2) 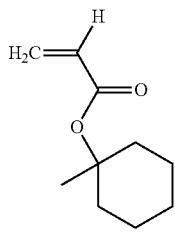

(a1-2-3) 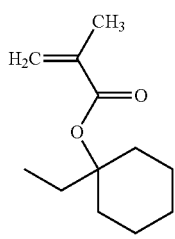

(a1-2-4) 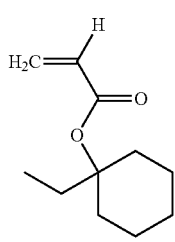

(a1-2-5) 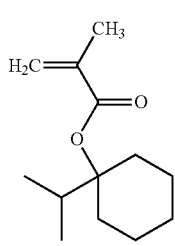

(a1-2-6) 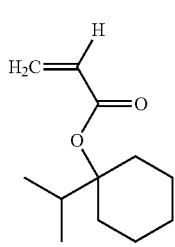

(a1-2-7) 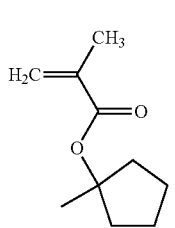

(a1-2-8) 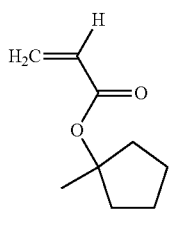

(a1-2-9) 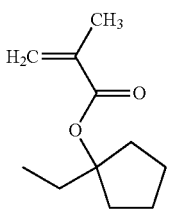

(a1-2-10) 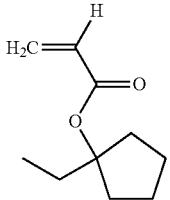

(a1-2-11) 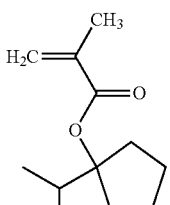

(a1-2-12) 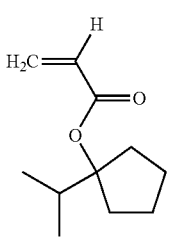

The content of the structural unit having an acid-labile group in the resin is usually 10 to 95% by mole, preferably 15 to 90% by mole and more preferably 20 to 85% by mole based on 100% by mole of all the structural units of the resin. The content of the structural unit having an acid-labile group in the resin can be adjusted by adjusting the amount of the monomer having an acid-labile group based on the total amount of the monomers used for producing the resin.

When the resin comprises one or more of the structural units represented by formulae (a1-0), (a1-1) and (a1-2), the total content of the structural units is usually 10 to 95% by mole, preferably 15 to 90% by mole and more preferably 15 to 90% by mole and still more preferably 20 to 85% by mole based on 100% by mole of all the structural units of the resin.

Other examples of the structural unit (a1) having a group represented by formula (1) include a structural unit represented by formula (a1-3):

(a1-3)

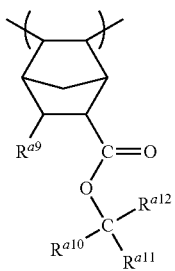

wherein $R^{a9}$ represents a hydrogen atom, a carboxyl group, a cyano group, a C1-C3 aliphatic hydrocarbon group which can have a hydroxy group, or a group represented by —COOR$^{a13}$ group in which $R^{a13}$ represents a C1-C8 alkyl group or a C3-C20 alicyclic hydrocarbon group, and a group composed of a C1-C8 aliphatic hydrocarbon group and a C3-C20 alicyclic hydrocarbon group, and the aliphatic hydrocarbon group and the alicyclic hydrocarbon group can have a hydroxy group, and a methylene in the alkyl group and the alicyclic hydrocarbon group can be replaced by —O— or —CO—, $R^{a10}$, $R^{a11}$ and $R^{a12}$ each independently represent a C1-C12 alkyl group or a C3-C20 alicyclic hydrocarbon group, and $R^{a10}$ and $R^{a11}$ can be bonded each other to form a C3-C20 ring together with the carbon atom to which $R^{a10}$ and $R^{a11}$ are bonded, and the alkyl group and the alicyclic hydrocarbon group can have a hydroxy group, and a methylene group in alkyl group and the alicyclic hydrocarbon group can be replaced by —O— or —CO—.

As $R^{a9}$, examples of the alkyl group which can have a hydroxy group include a methyl group, an ethyl group, a propyl group, a hydroxymethyl group and a 2-hydroxyethyl group.

Examples of the aliphatic hydrocarbon group represented by $R^{a13}$ include a methyl group, an ethyl group, a propyl group.

Examples of the alicylic hydrocarbon group represented by $R^{a13}$ include a cyclopropyl group, a cyclobutyl group, an adamantyl group, an adamantylmethyl group, a 1-adamantyl-1-methylethyl group, a 2-oxo-oxolan-3-yl group and a 2-oxo-oxolan-4-yl group.

Examples of the alkyl group represented by $R^{a10}$, $R^{a11}$ and $R^{a12}$ include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group.

The alicylic hydrocarbon group represented by $R^{a10}$, $R^{a11}$ and $R^{a12}$, which may be a monocyclic or polycyclic group. Examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group, a cycloheptyl group, a cyclodecyl group. Examples of the polycyclic alicyclic hydrocarbon group include a hydronaphthyl group, an adamantyl group, a 2-alkyladamantane-2-yl group, a 1-(adamantane-1-yl)alkane-1-yl group, a norbornyl group, a methylnorbornyl group, and an isobornyl group.

When the divalent hydrocarbon group is formed by bonding $R^{a10}$ and $R^{a11}$, examples of —C($R^{a10}$)($R^{a11}$)($R^{a12}$) include the following ones;

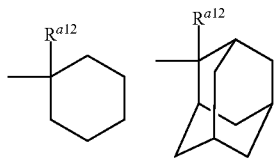

where $R^{a12}$ is as defined above.

Examples of the monomer from which the structural unit represented by formula (a1-3) is derived include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When the resin has a structural unit represented by formula (a1-3), the photoresist composition having excellent resolution and higher dry-etching resistance tends to be obtained.

When Resin (A) comprises the structural unit represented by formula (a1-3), the content of the structural unit is usually 10 to 95% by mole and preferably 15 to 90% by mole and more preferably 20 to 85% by mole based on total molar of all the structural units of the resin.

Other examples of the structural unit (a1) having a group represented by formula (2) include one represented by formula (a1-4):

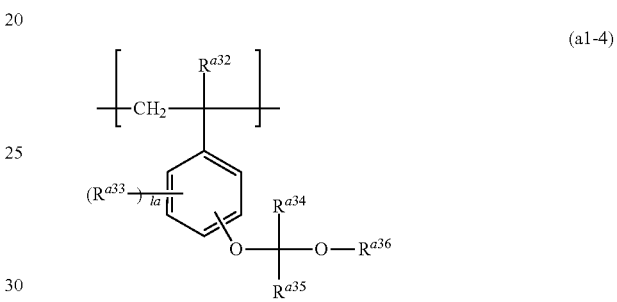

(a1-4)

wherein $R^{a32}$ represents a hydrogen atom, a halogen atom, a C1-C6 alkyl group or a C1-C6 halogenated alkyl group, $R^{a33}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, $l^a$ represents an integer of 0 to 4, $R^{a34}$ and $R^{a35}$ each independently represent a hydrogen atom or a C1-C12 hydrocarbon group, $R^{a36}$ represents a C1-C20 aliphatic hydrocarbon group in which a methylene group can be replaced by —O— or —S—, and $R^{a35}$ and $R^{a36}$ are bonded to each other to jointly represent a C2-C20 divalent hydrocarbon group in which a methylene group can be replaced by —O— or —S—.

Examples of the alkyl group represented by $R^{a32}$ and $R^{a33}$ include a methyl group, an ethyl group, a propyl group, a butyl group, a pentyl group, and a hexyl group, preferably a C1-C4 alkyl group, more preferably a methyl group and an ethyl group, and still more preferably a methyl group.

Examples of the alkoxy group represented by $R^{a33}$ include a methoxy group, an ethoxy group, a propoxy group, an isopropoxy group, a butoxy group, an isobutoxy group, a sec-butoxy group, a tert-butoxy group, a pentyloxy group and a hexyloxy group. Examples of the acyl group represented by $R^{a33}$ include an acetyl group, a propyonyl group and a butyryl group, and examples of the acyloxy group represented by $R^{a33}$ include an acetyloxy group, a propyonyloxy group and a butyryloxy group.

Examples of halogen atom represented by $R^{a32}$ and $R^{a33}$ include a fluorine atom, a chlorine atom, and a bromine atom.

Examples of the groups represented by $R^{a34}$ and $R^{a35}$ include those as referred to for $R^{a1'}$ and $R^{a2'}$.

Examples of the groups represented by $R^{a36}$ include those as referred to for $R^{a3'}$.

$R^{a32}$ preferably represents a hydrogen atom.

$R^{a33}$ is preferably a C1-C4 alkoxy group, more preferably a methoxy group and an ethoxy group, and still more preferably a methoxy group.

The symbol "la" preferably represents 0 or 1, more preferably 1.

$R^{a34}$ preferably represents a hydrogen atom.

$R^{a35}$ is preferably a C1-C12 monovalent hydrocarbon group, more preferably a methyl group and an ethyl group.

The hydrocarbon group represented by $R^{a36}$ includes a C1-C18 alkyl group, a C3-C18 monovalent alicyclic hydrocarbon group, a C6-C18 monovalent aromatic hydrocarbon group, and any combination of them, and preferably a C1-C18 alkyl group, a C3-C18 monovalent alicyclic hydrocarbon group and a C7-C18 aralkyl group. These groups may be unsubstituted or substituted. The alkyl group and the monovalent alicyclic hydrocarbon group are preferably unsubstituted. As the substituent for the monovalent aromatic hydrocarbon group, a C6-C10 aryloxy group is preferred.

Examples of the monomer from which the structural unit (a1-4) is derived include monomers recited in JP2010-204646A1. Among them, the monomers represented by formulae (a1-4-1), (a1-4-2), (a1-4-3), (a1-4-4), (a1-4-5), (a1-4-6) and (a1-4-7) are preferred, and the monomers represented by formulae (a1-4-1), (a1-4-2), (a1-4-3), (a1-4-4) and (a1-4-5) are more preferred.

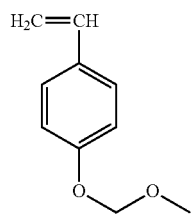

(a1-4-1)

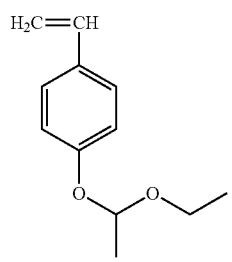

(a1-4-2)

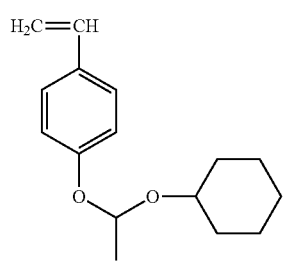

(a1-4-3)

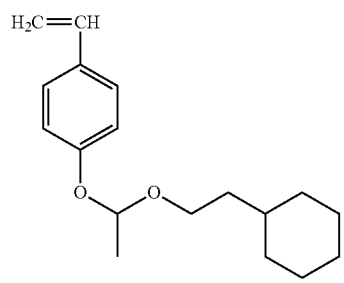

(a1-4-4)

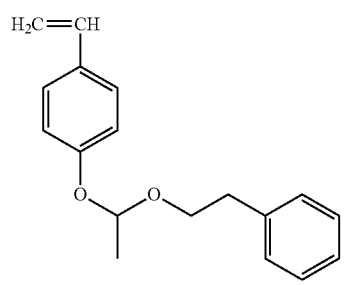

(a1-4-5)

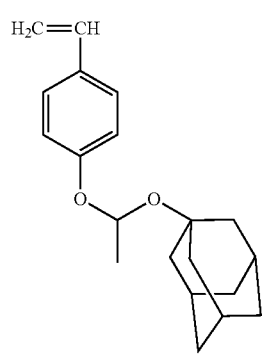

(a1-4-6)

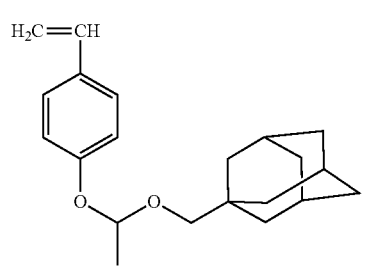

(a1-4-7)

When Resin (A) comprises a structural unit represented by formula (a1-4), its content is usually 10 to 95% by mole, preferably 15 to 90% by mole and more preferably 20 to 85% by mole based on 100% by mole of all the structural units of the resin.

Other examples of the structural unit having an acid-labile group include one represented by formula (a1-5):

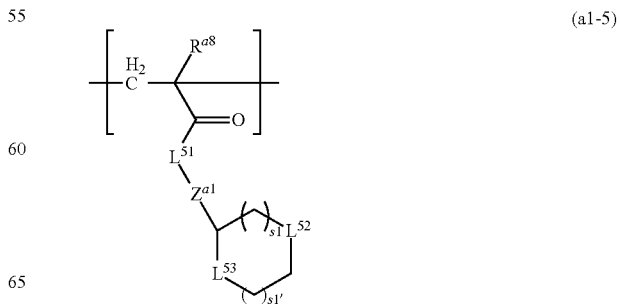

(a1-5)

In formula (1-5), $R^{a8}$ represents a hydrogen atom, a halogen atom, or a C1-C6 alkyl group which may have a halogen atom, $Z^{a1}$ represents a single bond or *—$(CH_2)_{h3}$—CO-$L^{54}$- in which k1 represents an integer of 1 to 4 and * represents a binding site to $L^{54}$, $L^{51}$, $L^{52}$, $L^{53}$ and $L^{54}$ each independently represent an oxygen atom or a sulfur atom, s1 represents an integer of 1 to 3, and s1' represents an integer of 0 to 3.

Herein, the structural unit represented by formula (a-5) is sometimes referred to as "structural unit (a-5)".

Examples of halogen atoms include a fluorine atom and chlorine atom, preferably a fluorine atom.

Examples of the alkyl group which may have a halogen atom include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group, a fluoromethyl group, and a trifluoromethyl group.

In the formula (a-5), $R^{a8}$ preferably represents a hydrogen atom, a methyl group, or trifluoromethyl group.

$L^{51}$ represents preferably an oxygen atom.

It is preferred that one of $L^{52}$ and $L^{53}$ represents an oxygen atom, while the other represents a sulfur atom.

s1 preferably represents 1. s1' represents an integer of 0 to 2.

$Z^{a1}$ preferably represents a single bond or *—$CH_2$—CO—O— wherein * represents a binding site to $L^{51}$.

Examples of the monomer from which the structural unit (a-5) is derived include one mentioned in JP2010-61117A1 and the following ones:

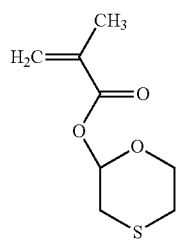

(a1-5-1)

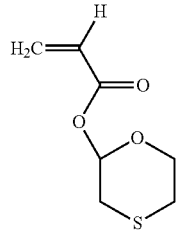

(a1-5-2)

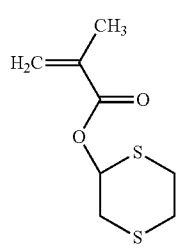

(a1-5-3)

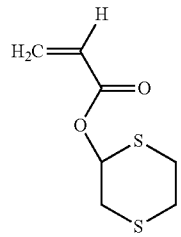

(a1-5-4)

When Resin (A) comprises a structural unit (a-5), its content is usually 1 to 50% by mole, preferably 3 to 45% by mole and more preferably 5 to 40% by mole based on 100% by mole of all the structural units of the resin.

Resin (A) comprises preferably one or more of the structural units (a-0), (a-1), (a-2) and (a-5), more preferably at least one of the structural units (a-1), (a-2) and (a-5), still more preferably two or more of the structural units (a-1), (a-2) and (a-5), and further more preferably the structural units (a-1) and (a-2) or the structural units (a-1) and (a-5).

Resin (A) comprises preferably the structural unit (a-1).

The structural unit (s) is derived from a monomer having no acid-labile group.

As to the monomer having no acid-labile group, monomers which have been known to in the art can be used as such monomer, and they are not limited to any specific one provided that it has no acid-labile group.

The structural unit having no acid-labile group preferably has a hydroxy group or a lactone ring. When the resin comprises the structural unit derived from the monomer having no acid-labile group and having a hydroxy group or a lactone ring, a photoresist composition capable of providing a photoresist film with good resolution and adhesiveness of photoresist to a substrate can be obtained.

Hereinafter, the structural unit having no acid-labile group and having a hydroxy group is referred to as "structural unit (a2)", and the structural unit having no acid-labile group and having a lactone ring is referred to as "structural unit (a3)".

The hydroxy group which the structural unit (a2) has may be an alcoholic hydroxy group or a phenolic hydroxy group.

When KrF excimer laser (wavelength: 248 nm) lithography system, or a high energy laser such as electron beam and extreme ultraviolet is used as an exposure system, the resin which comprises the structural unit (a2) having a phenolic hydroxy group is preferred. When ArF excimer laser (wavelength: 193 nm) is used as an exposure system, the resin which comprises the structural unit (a2) having an alcoholic hydroxy group is preferred and the resin which comprises the structural unit (a2-1) described later is more preferred.

Resin (A) may comprise one or more of the structural units (a2).

Examples of the structural unit (a2) having a phenolic hydroxy group include one represented by formula (a2-0):

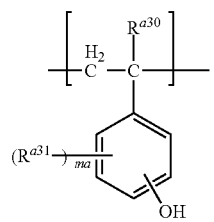

(a2-0)

In formula (a2-0), $R^{a30}$ represents a hydrogen atom, a halogen atom, a C1-C6 alkyl group or a C1-C6 halogenated alkyl group, $R^{a31}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, ma represents an integer of 0 to 4.

In the formula (a2-0), examples of the halogen atom include a fluorine atom, a chlorine atom, a bromine atom or iodine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferred and a C1-C2 alkyl group is more preferred and a methyl group is especially preferred.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferred and a C1-C2 alkoxy group is more preferred and a methoxy group is especially preferred. Examples of the C2-C4 acyl group include an acetyl group, a propyonyl group and a butyryl group, and examples of the C2-C4 acyloxy group include an acetyloxy group, a propyonyloxy group and a butyryloxy group.

In the formula (a2-0), ma is preferably 0, 1 or 2, and is more preferably 0 or 1, and especially preferably 0.

Among them, the structural units represented by formulae (a2-0-1), (a2-0-2), (a2-0-3) and (a2-0-4) are preferred as the structural unit (a2-0), and those represented by formulae (a2-0-1) and (a2-0-2) are more preferred.

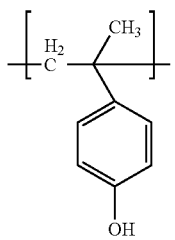

(a2-0-1)

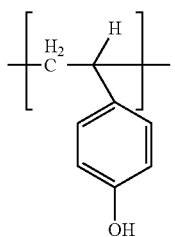

(a2-0-2)

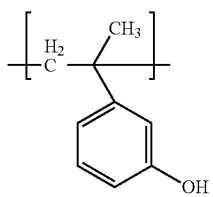

(a2-0-3)

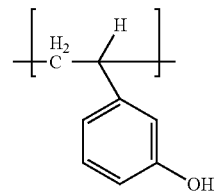

(a2-0-4)

Resin (A) which comprises a structural unit represented by formula (a2-0) can be produced, for example, by polymerizing a monomer where its phenolic hydroxy group has been protected with a suitable protecting group, followed by deprotection. Examples of the protecting group for a phenolic hydroxy group include an acetyl group.

When Resin (A) comprises the structural unit represented by formula (a2-0), its content is usually 5 to 95% by mole and preferably 10 to 85% by mole and more preferably 15 to 80% by mole based on total molar of all the structural units of the resin.

Examples of the structural unit (a2) having an alcoholic hydroxy group include one represented by formula (a2-1):

$$\text{(a2-1)}$$

wherein $R^{a14}$ represents a hydrogen atom or a methyl group, $R^{a15}$ and $R^{a16}$ each independently represent a hydrogen atom, a methyl group or a hydroxy group, $L^{a3}$ represents *—O— or *—O—$(CH_2)_{k2}$—CO—O— in which * represents a binding site to —CO—, and k2 represents an integer of 1 to 7, and o1 represents an integer of 0 to 10.

Hereinafter, the structural unit represented by formula (a2-1) is referred to as "structural unit (a2-1)".

In the formula (a2-1), $R^{a14}$ is preferably a methyl group. $R^{a15}$ is preferably a hydrogen atom. $R^{a16}$ is preferably a hydrogen atom or a hydroxy group. $L^{a3}$ is preferably *—O— or *—O—$(CH_2)_{r2}$—CO—O— in which * represents a binding site to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

Examples of monomers from which the structural unit (a2-1) is derived include compounds mentioned in JP2010-204646A.

Preferred examples of the structural unit (a2-1) include those represented by formulae (a2-1-1) to (a2-1-6).

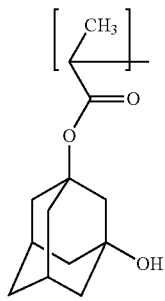
(a2-1-1)

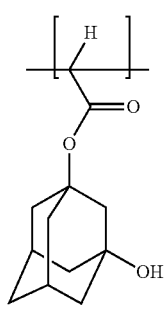
(a2-1-2)

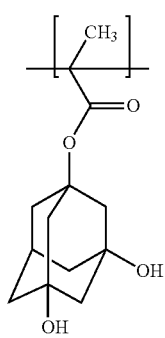
(a2-1-3)

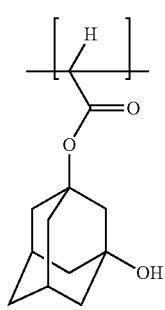
(a2-1-4)

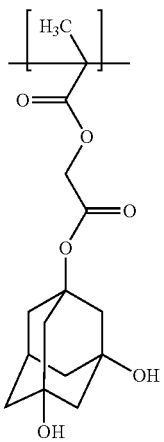
(a2-1-5)

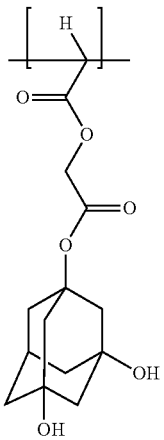
(a2-1-6)

Among them, more preferred are the structural units represented by formulae (a2-1-1), (a2-1-2), (a2-1-3) and (a2-1-4), still more preferred are the structural units represented by formulae (a2-1-1) and (a2-1-3).

When Resin (A) comprises the structural unit (a2-1), its content is usually 1 to 45% by mole, preferably 1 to 40% by mole, and more preferably 1 to 35% by mole, and especially preferably 2 to 20% by mole, based on total molar of all the structural units of the resin.

Examples of the lactone ring of the structural unit (a3) include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring. Preferred examples of the structural unit (a3) include those represented by formulae (a3-1), (a3-2), (a3-3) and (a3-4):

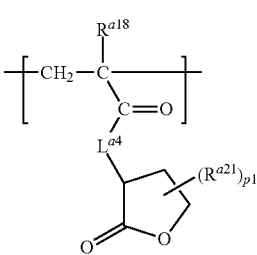
(a3-1)

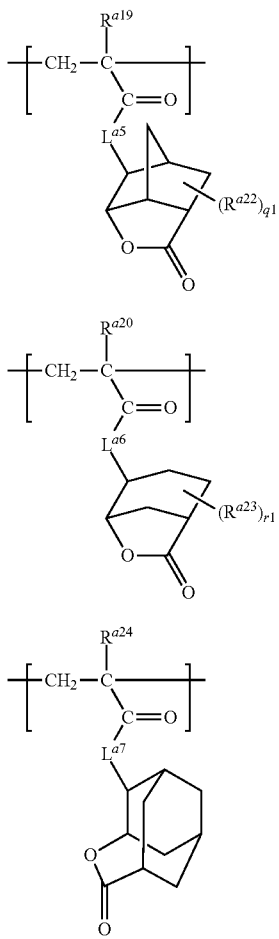

(a3-2)

(a3-3)

(a3-4)

In formulae, $L^{a4}$, $L^{a5}$ and $L^{a6}$ each independently represent *—O— or *—O—$(CH_2)_{k3}$—CO—O— in which * represents a binding site to —CO— and k3 represents an integer of 1 to 7, $R^{a18}$, $R^{a19}$ and $R^{a20}$ each independently represent a hydrogen atom or a methyl group, $R^{a21}$ represents a C1-C4 monovalent aliphatic hydrocarbon group, $R^{a22}$ and $R^{a23}$ are independently in each occurrence a carboxyl group, a cyano group or a C1-C4 monovalent aliphatic hydrocarbon group, $R^{a24}$ each independently represent a hydrogen atom, a halogen atom, or a C1-C6 alkyl group which may have a halogen atom, $L^{a7}$ represents a single bond, $*^1$-$L^{a8}$-O—, $*^1$-$L^{a8}$-CO—O—, $*^1$-$L^{a8}$-CO—O-$L^{a9}$-CO—O— or $*^1$-$L^{a8}$-CO—O-$L^{a9}$-O— in which $L^{a8}$ and $L^{a9}$ each independently represent C1-C6 divalent alkanediyl group, $*^1$ represents a binding site to —O—, and p1 represents an integer of 0 to 5, q1 and r1 independently each represent an integer of 0 to 3.

Examples of halogen atom represented by $R^{a24}$ include a fluorine atom, a chlorine atom, a bromine atom and an iodine atom.

Examples of the alkyl group represented by $R^{a24}$ include a methyl group, an ethyl group, a propyl group, a butyl group, a pentyl group, and a hexyl group, preferably a C1-C4 alkyl group, and more preferably a methyl group and an ethyl group.

As to $R^{a24}$, examples of the alkyl group which has an halogen atom include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a trichloromethyl group, a tribromomethyl group, and a triiodomethyl group.

As to $L^{a8}$ and $L^{a9}$, examples of the alkanediyl group include a methylene group, an ethylene group, a propane-1,3-diyl group, a butane-1,4-diyl group, a pentane-1,5-diyl group and a hexane-1,6-diyl group, a butane-1,3-diyl group, 2-methylpropane-1,3-diyl group, a 2-methylpropane-1,2-diyl group, a pentane-1,4-diyl group and a 2-methylbutane-1,4-diyl group.

It is preferred that $L^{a4}$, $L^{a5}$ and $L^{a6}$ each independently represent *—O— or *—O—$(CH_2)_{d1}$—CO—O— in which * represents a binding site to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group.

It is preferred that p1, q1 and r1 each independently represent an integer of 0 to 2, and it is more preferred that p1, q1 and r1 each independently represent 0 or 1.

$R^{a24}$ is preferably a hydrogen atom or a C1-C4 alkyl group, more preferably a hydrogen atom, a methyl group or an ethyl group, and still more preferably a hydrogen atom or a methyl group.

$L^{a7}$ represents preferably a single bond or $*^1$-$L^{a8}$-CO—O—, more preferably a single bond, $*^1$—$CH_2$—CO—O— or $*^1$—$C_2H_4$—CO—O—.

Examples of the structural unit (a3) include the following ones.

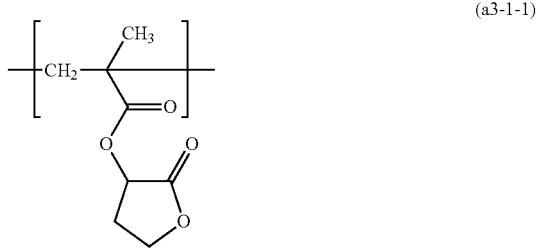

(a3-1-1)

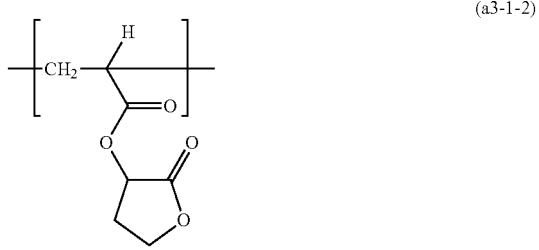

(a3-1-2)

-continued
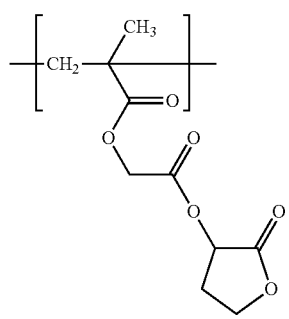 (a3-1-3)
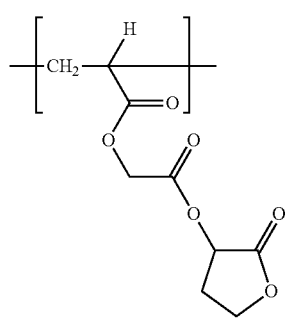 (a3-1-4)
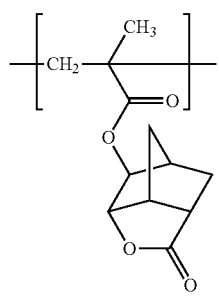 (a3-2-1)
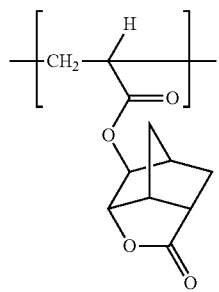 (a3-2-2)
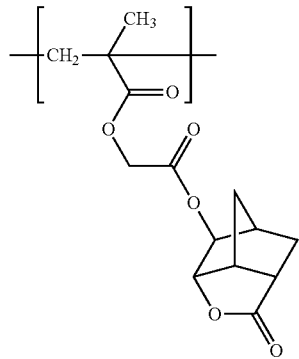 (a3-2-3)
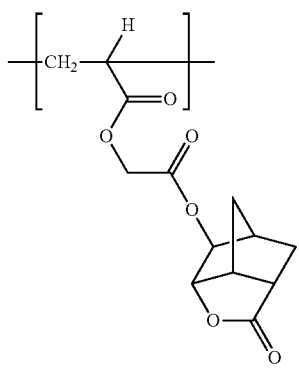 (a3-2-4)
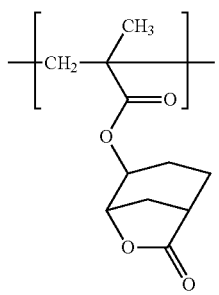 (a3-3-1)
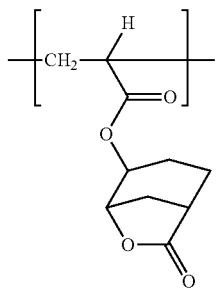 (a3-3-2)
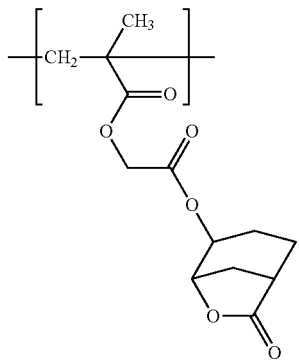 (a3-3-3)

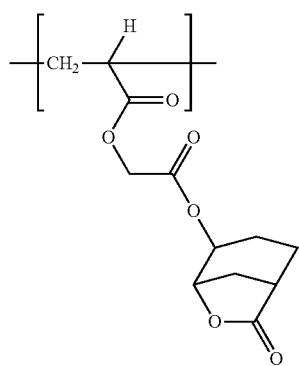
(a3-3-4)
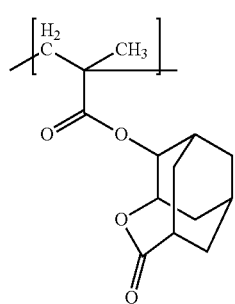
(a3-4-1)
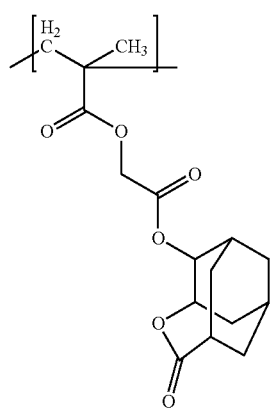
(a3-4-2)
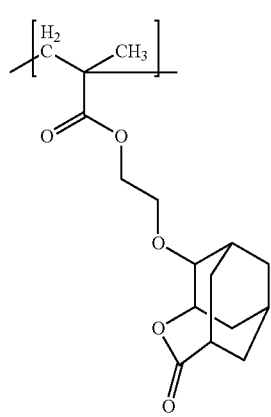
(a3-4-3)
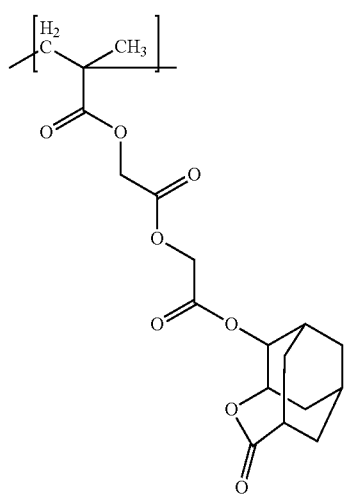
(a3-4-4)
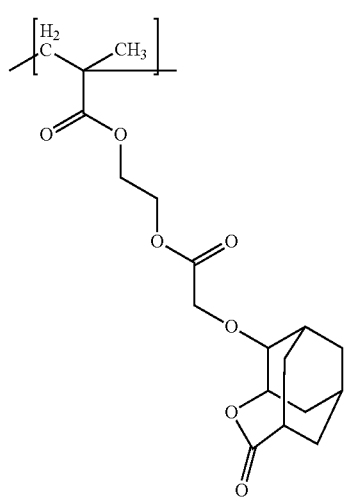
(a3-4-5)
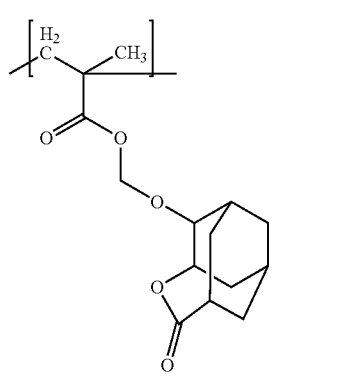
(a3-4-6)
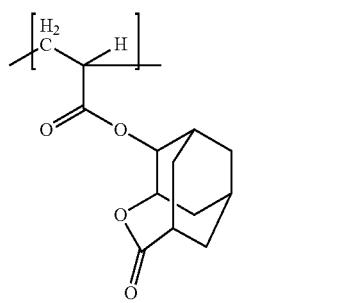
(a3-4-7)

-continued

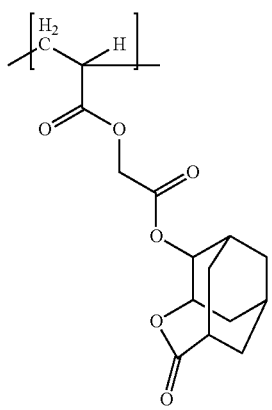
(a3-4-8)

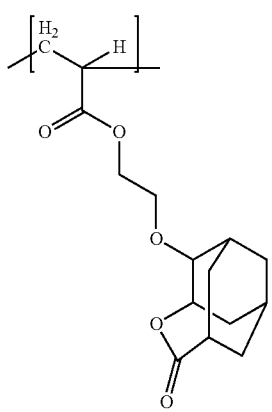
(a3-4-9)

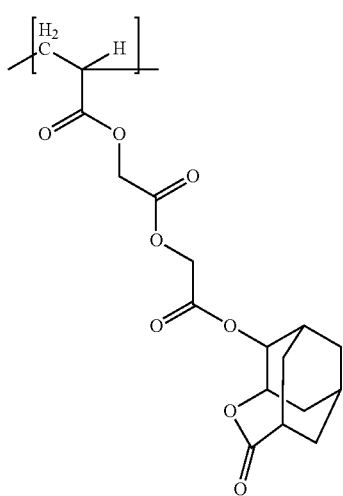
(a3-4-10)

-continued

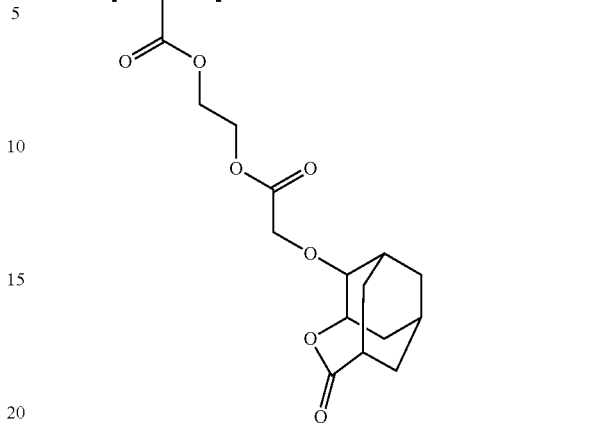
(a3-4-11)
(a3-4-12)

The structural unit (a3) is preferably one of formulae (a3-1-1) to (a3-1-4), formulae (a3-2-1) to (a3-2-4), formulae (a3-3-1) to (a3-3-4) and formulae (a3-4-1) to (a3-4-12), more preferably one of formulae (a3-1-1), formula (a3-1-2), formulae (a3-2-3) to (a3-2-4) and formulae (a3-4-1) to (a3-4-2), and still more preferably one of formulae (a3-1-1), (a3-2-3) and (a3-4-2).

Examples of the monomer from which the structural unit (a3) is derived include those mentioned in US2010/203446A1, US2002/098441A1 and US2013/143157A1.

When Resin (A) comprises the structural unit (a3), its content thereof is preferably 5 to 70% by mole, and more preferably 10 to 65% by mole and more preferably 10 to 60% by mole, based on total molar of all the structural units of the resin.

Examples of another structural unit having no acid-labile group include a structural unit having a fluorine atom and a structural unit which has a hydrocarbon not being removed therefrom by action of an acid.

Examples of the structural unit having a fluorine atom include the following one.

Hereinafter, the structural unit having no acid-labile group but having a halogen atom is referred to as "structural unit (a4)". Halogen atoms for the structural unit (a4) may be a fluorine atom, a chlorine atom, a bromine atom, or an iodine atom. The structural unit (a4) has preferably a fluorine atom.

Examples of the structural unit (a4) include one represented by formula (a4-0):

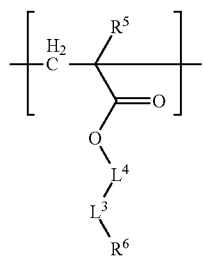
(a4-0)

wherein R⁵ represents a hydrogen atom or a methyl group;

L⁴ represents a single bond or a C1-C4 aliphatic saturated hydrocarbon group, preferably a C1-C4 aliphatic saturated hydrocarbon group;

L³ represents a C1-C8 perfluoroalkanediyl group or a C3-C12 alicyclic perfluorohydrocarbon group; and R⁶ represents a hydrogen atom or a fluorine atom.

Examples of the perfluoroalkanediyl group for L³ include a difluoromethylene group, a perfluoroethylene group, a (perfluoroethyl)fluoromethylene group, a perfluoropropane-1,3-diyl group, a perfluoropropane-1,2-diyl group, a perfluorobutane-1,4-diyl group, a perfluoropentane-1,5-diyl group, a perfluorohexane-1,6-diyl group, a perfluoroheptane-1,7-diyl group, and a perfluorooctane-1,8-diyl group.

Examples of the alicyclic perfluorohydrocarbon group for L³ include a perfluoroadamantandiyl group.

L⁴ is preferably a methylene group or an ethylene group, more preferably a methylene group.

L³ is preferably a C1-C6 perfluoroalkanediyl group, more preferably a C1-C3 perfluoroalkanediyl group.

Examples of the structural unit represented by formula (a4-0) include the following ones and those in which a methyl group has been replaced by a hydrogen atom in each of the following formulae.

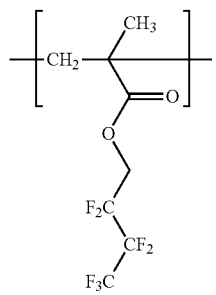
(a4-0-1)

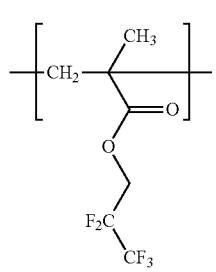
(a4-0-2)

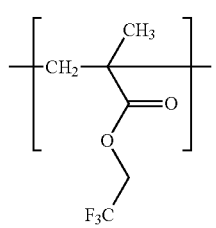
(a4-0-3)

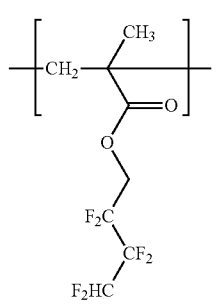
(a4-0-4)

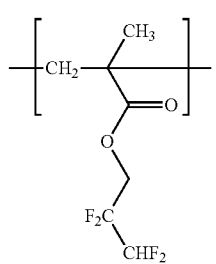
(a4-0-5)

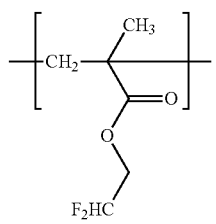
(a4-0-6)

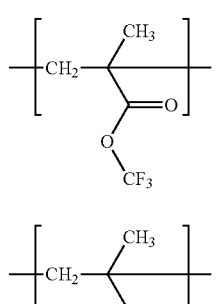
(a4-0-7)

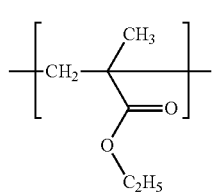
(a4-0-8)

(a4-0-9) 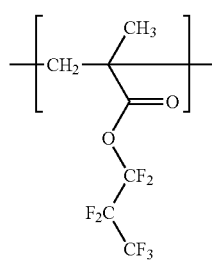
(a4-0-10) 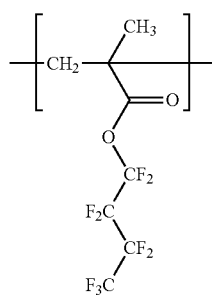
(a4-0-11) 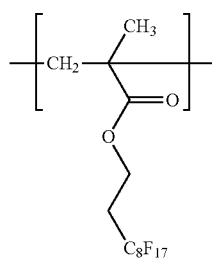
(a4-0-12) 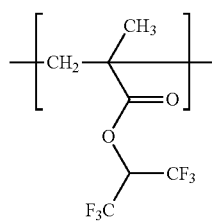
(a4-0-13) 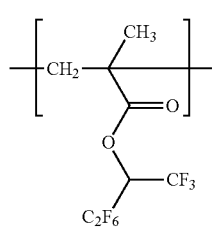
(a4-0-14) 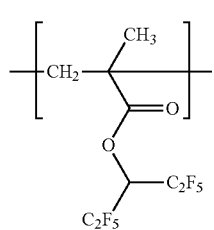
(a4-0-15) 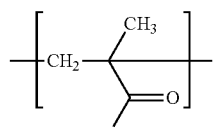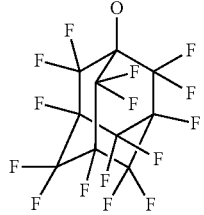
(a4-0-16) 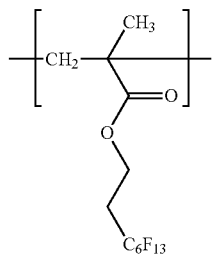
(a4-0-17) 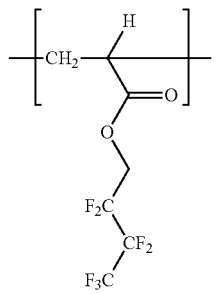
(a4-0-18) 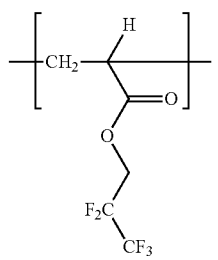
(a4-0-19) 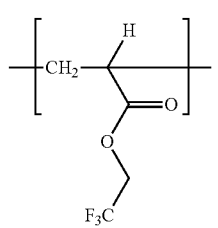

(a4-0-20) 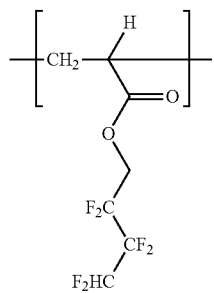
(a4-0-21) 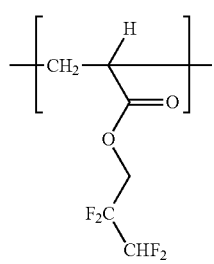
(a4-0-22) 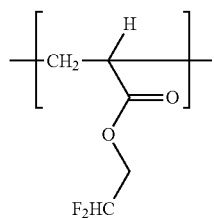
(a4-0-23) 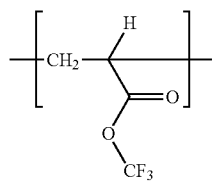
(a4-0-24) 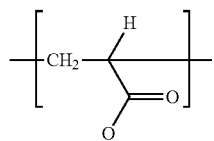
(a4-0-25) 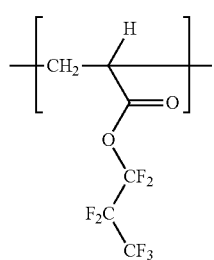
(a4-0-26) 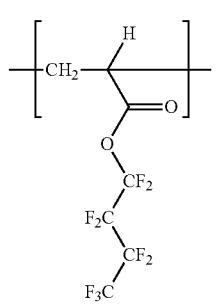
(a4-0-27) 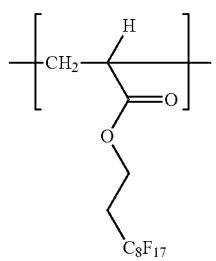
(a4-0-28) 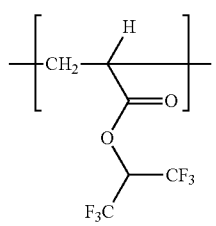
(a4-0-29) 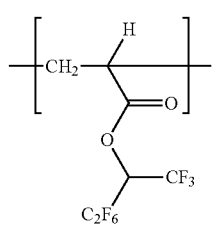
(a4-0-30) 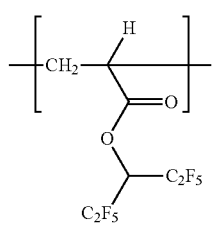
(a4-0-31) 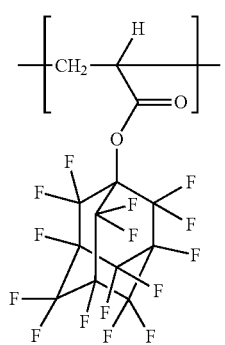

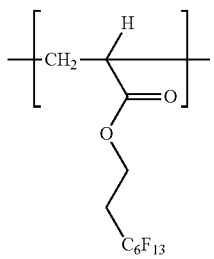

(a4-O-32)

Examples of the structural unit (a4) include one represented by formula (a4-1):

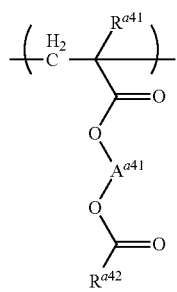

(a4-1)

wherein $R^{a41}$ represents a hydrogen atom or a methyl group; $A^{a41}$ represents a C1-C6 divalent alkanediyl group which may have a substituent or a moiety represented by formula (a-g1):

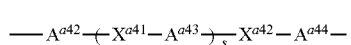

(a-g1)

in which s represents an integer of 0 to 1,
$A^{a42}$ and $A^{a44}$ respectively represent a C1-C5 divalent hydrocarbon group which may have a substituent,
$A^{a43}$ represents a single bond or a C1-C5 divalent hydrocarbon group which may have a substituent,
$X^{a41}$ and $X^{a42}$ respectively represent —O—, —CO—, —CO—O—, or —O—CO—, provided that the sum of carbon atoms of $A^{a42}$, $A^{a43}$, $A^{a44}$, $X^{a41}$ and $X^{a42}$ is 6 or less;
$R^{a42}$ represents a C1-C20 monovalent hydrocarbon group which may have a substituent, provided that each or both of $A^{a41}$ and $R^{a42}$ have a halogen atom; and
$A^{a44}$ is bonded to —O—CO—$R^{a42}$.

Examples of halogen atom for formula (a4-1) include a fluorine atom, a chlorine atom, a bromine atom and an iodine atom.

The divalent hydrocarbon group is preferably a divalent saturated hydrocarbon group while it may have a carbon-carbon double bond.

Examples of the divalent saturated hydrocarbon group include alkanediyl groups which may be a linear or branched one, divalent alicyclic hydrocarbon groups, and combination of them.

Examples of the monovalent hydrocarbon group for $R^{a42}$ include monovalent chain or cyclic saturated hydrocarbon groups, a monovalent aromatic hydrocarbon group, and combination of them.

Examples of monovalent chain hydrocarbon group include a methyl group, an ethyl group, a propyl group, a butyl group, a pentyl group, a hexyl group, a heptyl group, an octyl group, a decyl group, a dodecyl group, a hexadecyl group, a pentadecyl group, a hexyldecyl group, heptadecyl group and an octadecyl group.

Examples of monovalent cyclic hydrocarbons include cycloalkyl groups such as a cyclopentyl group, a cyclohexyl group, a cycloheptyl group and a cyclooctyl group; and monovalent polycyclic hydrocarbon groups such as a decahydronaphthyl group, an adamantyl group, a norbornyl group, and the following groups where * represents a binding position.

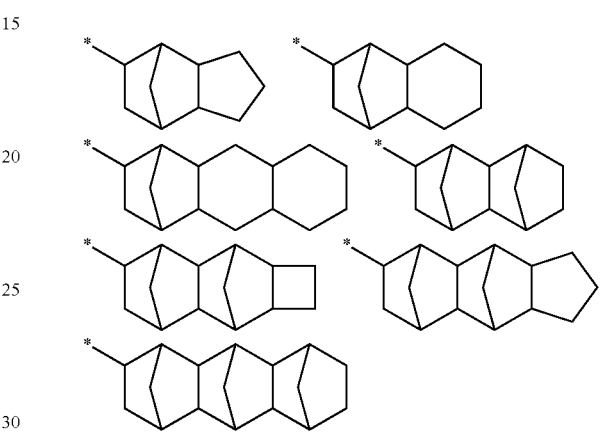

Examples of monovalent aromatic hydrocarbon groups include a phenyl group, a naphthyl group, an anthryl group, a biphenylyl group, a phenanthryl group and a fluorenyl group.

The monovalent hydrocarbon group for $R^{a42}$ is preferably monovalent chain and cyclic hydrocarbon groups and combination of them, which may have a carbon-carbon double bond, and more preferably a monovalent chain hydrocarbon group and cyclic hydrocarbon group and combination of them.

$R^{a42}$ is preferably a monovalent aliphatic hydrocarbon group which has a substituent, more preferably a monovalent aliphatic hydrocarbon group which has a halogen atom and/or a group represented by formula (a-g3).

(a-g3)

in which $X^{a43}$ represents an oxygen atom, a carbonyl group, a carbonyloxy group or an oxycarbonyl group,
$A^{a45}$ represents a C3-C17 monovalent saturated hydrocarbon group which may have a fluorine atom.

When $R^{a42}$ is a monovalent saturated hydrocarbon group which has a group represented by formula (a-g3), $R^{a42}$ has preferably 15 or less carbon atoms, more preferably 12 or less carbon atoms in total including the carbon atoms of formula (a-g3). If $R^{a42}$ has a group represented by formula (a-g3), the number of the group is preferably 1.

The monovalent saturated hydrocarbon group which has a group represented by formula (a-g3) is preferably a compound represented by formula (a4-g2):

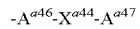

(a-g2)

in which $A^{a46}$ represents a C3-C17 divalent saturated hydrocarbon group which may have a fluorine atom, $X^{a44}$ represents a carbonyloxy group or an oxycarbonyl group, and $A^{a47}$ represents a C3-C17 divalent saturated hydrocarbon group which may have a fluorine atom, provided that $A^{a46}$, $A^{a47}$ and $X^{a44}$ have 18 or less of carbon atoms in total and one or both of $A^{a46}$ and $A^{a47}$ have a fluorine atom.

The halogen-containing saturated hydrocarbon group represented by $R^{a42}$ is preferably a monovalent fluorine-containing saturated hydrocarbon group, more preferably a perfluoroalkyl group or a perfluorocycloalkyl group, still more preferably a C1-C6 perfluoroalkyl group, and further more preferably a C1-C3 perfluoroalkyl group.

Examples of perfluoroalkyl group include a perfluoromethyl group, a perfluoroethyl group, a perfluoropropyl group, a perfluorobutyl group, a perfluoropentyl group, a perfluorohexyl group, a perfluoroheptyl group, and a perfluorooctyl group. Examples of the perfluorocycloalkyl group include perfluorocyclohexyl group.

The divalent saturated hydrocarbon group represented by $A^{a46}$ has preferably 1 to 6, more preferably 1 to 3 carbon atoms.

The monovalent saturated hydrocarbon group represented by $A^{a47}$ has preferably 4 to 15, more preferably 5 to 12 carbon atoms. $A^{a47}$ is more preferably a cyclohexyl group or an adamantyl group.

Examples of the moiety represented by $-A^{a46}-X^{a44}-A^{a47}$ include the following ones.

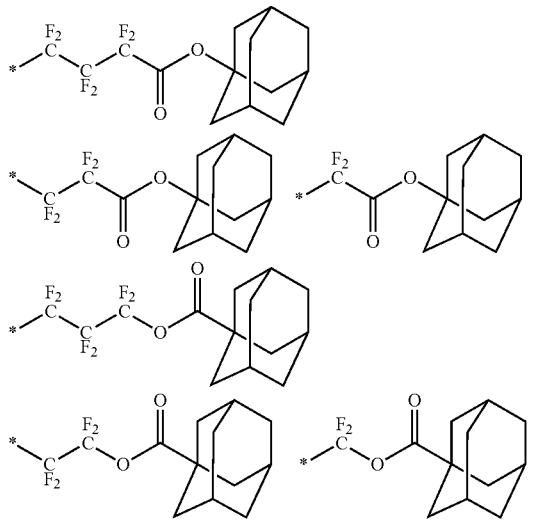

In each formula, * represents a binding position to a carbonyl group.

Examples of $A^{a41}$ typically include a C1-C6 alkanediyl group which may be a linear chain or branched chain. Specific examples of them include linear chain alkanediyl groups such as a methylene group, an ethylene group, a propane-1,3-diyl group, a butane-1,4-diyl group, a pentane-1,5-diyl group, or a hexane-1,6-diyl group; and branched chain alkanediyl groups such as a propane-1,3-diyl group, a butane-1,3-diyl group, a 1-methylbutane-1,2-diyl group, or a 2-methylbutane-1,4-diyl group. Examples of the substituents which such alkanediyl group may have include a hydroxy group or a C1-C6 alkoxy group.

$A^{a41}$ is preferably a C1-C4 alkanediyl group, more preferably a C2-C4 alkanediyl group, and still more preferably an ethylene group.

Examples of the alkanediyl group represented by $A^{a42}$, $A^{a43}$ and $A^{a44}$ include a methylene group, an ethylene group, a propane-1,3-diyl group, a butane-1,4-diyl group, a 2-methylpropane-1,3-diyl group, or a 2-methylbutane-1,4-diyl group. Examples of the substituents which such alkanediyl group may have include a hydroxy group or a C1-C6 alkoxy group.

$X^{a42}$ represents —O—, —CO—, —CO—O—, or —O—CO—.

Examples of the moiety represented by formula (a-g1) where $X^{a42}$ is an oxygen atom, a carbonyl group, a carbonyloxy group or an oxycarbonyl group include the following ones:

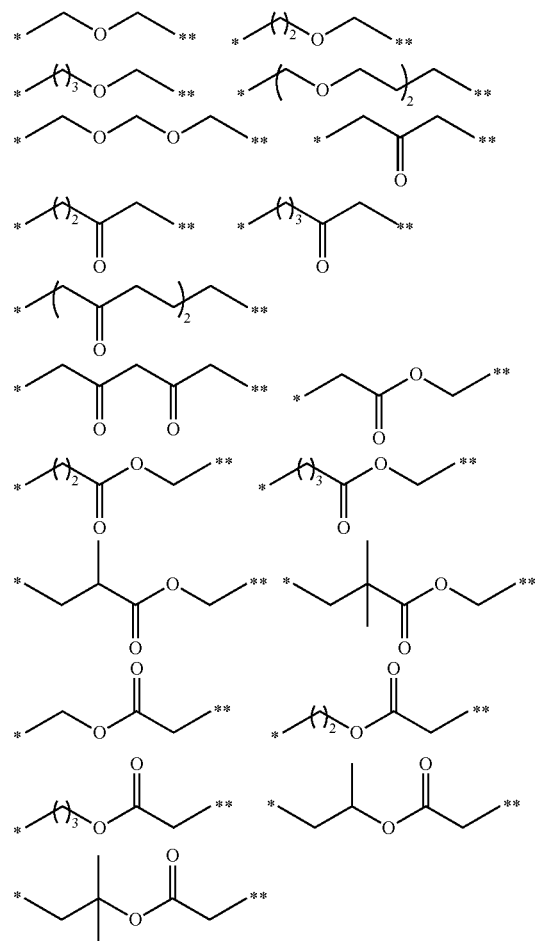

in which * and  represent binding sites, and  represents a binding site to —O—CO—$R^{a42}$.

The structural unit represented by formula (a4-1) is preferably one represented by formula (a4-2) or (a4-3).

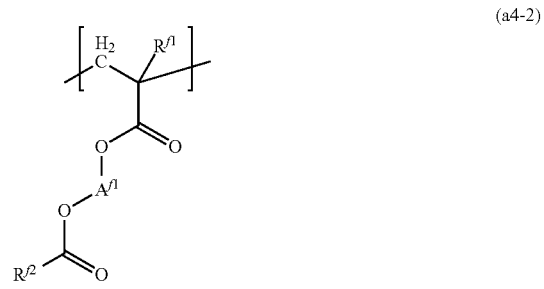

(a4-2)

In formula, $R^{f1}$ represents a hydrogen atom or a methyl group.

$A^{f1}$ represents C1-C6 alkanediyl group.

$R^{f2}$ represents a C1-C20, preferably C1-C10, monovalent hydrocarbon group having a fluorine atom.

The alkanediyl groups represented by $A^{f1}$ may be a linear chain or branched chain. Specific examples of them include linear chain alkanediyl groups such as a methylene group, an ethylene group, a propane-1,3-diyl group, a butane-1,4-diyl group, a pentane-1,5-diyl group, or a hexane-1,6-diyl group; and branched chain alkanediyl groups such as a propane-1,3-diyl group, a butane-1,3-diyl group, a 1-methylbutane-1,2-diyl group, or a 2-methylbutane-1,4-diyl group. Examples of the substituents which such alkanediyl group may have include a hydroxy group or a C1-C6 alkoxy group.

The monovalent hydrocarbon group represented by $R^{f2}$ includes monovalent saturated hydrocarbon groups and monovalent aromatic hydrocarbon groups. The monovalent saturated hydrocarbon groups may be a chain or cyclic saturated hydrocarbon group, or a combined group of them.

The monovalent saturated hydrocarbon groups are preferably an alkyl group or a monovalent alicyclic hydrocarbon group.

Examples of the alkyl group include a methyl group, an ethyl group, n-propyl group, isopropyl group, n-butyl group, sec-butyl group, a tert-butyl group, a pentyl group, a hexyl group and 2-ethylhexyl group.

The monovalent alicyclic hydrocarbon groups may be monocyclic or polycyclic groups. Examples of monovalent monocyclic hydrocarbon groups include a cyclopropyl group, a cyclobutyl group, a cyclopentyl group, a cyclohexyl group, a methylcyclohexyl group, a dimethylcyclohexyl group, a cycloheptyl group, a cyclooctyl group, a cycloheptyl group and a cyclodecyl group.

Examples of monovalent polycyclic hydrocarbon groups include a decahydronaphthyl group, an adamantyl group, a norbornyl group, and an isobornyl group.

Examples of the combined group of the above-mentioned hydrocarbon group include a 2-alkyladamantane-2-yl group, a 1-(adamantane-1-yl)alkane-1-yl group, and a methylnorbornyl group.

Examples of monovalent hydrocarbon groups having a fluorine atom for $R^{f2}$ include monovalent fluoroalkyl groups and monovalent fluorine atom-containing alicyclic hydrocarbon groups.

Specific examples of monovalent fluoroalkyl groups include a fluoromethyl group, a trifluoromethyl group, 1,1-difluoroethyl group, 2,2-difluoroethyl group, 2,2,2-trifluoroethyl group, perfluoroethyl group, 1,1,2,2-tetrafluoropropyl group, 1,1,2,2,3,3-hexafluoropropyl group, perfluoroethylmethyl group, 1-(trifluoromethyl)-1,2,2,2-tetrafluoroethyl group, perfluoropropyl group, 1,1,2,2-tetrafluorobutyl group, 1,1,2,2,3,3-hexafluorobutyl group, 1,1,2,2,3,3,4,4-octafluorobutyl group, perfluorobutyl group, 1,1-bis(trifluoro)methyl-2,2,2-trifluoroethyl group, 2-(perfluoropropyl)ethyl group, 1,1,2,2,3,3,4,4-octafluoropentyl group, perfluoropentyl group, 1,1,2,2,3,3,4,4,5,5-decafluoropentyl group, 1,1-bis(trifluoromethyl)-2,2,3,3,3-pentafluoropropyl group, 2-(perfluorobutyl) ethyl group, 1,1,2,2,3,3,4,4,5,5-decafluorohexyl group, 1,1,2,2,3,3,4,4,5,5,6,6-dodecafluorohexyl group, a perfluoropentylmethyl group and a perfluorohexyl group.

Specific examples of monovalent fluorine-containing alicyclic hydrocarbon groups include fluorocycloalkyl groups such as a perfluorocyclohexyl group and a perfluoroadamantyl group.

In formula (a4-2), $A^{f1}$ is preferably a C2-C4 alkylene group, and more preferably an ethylene group. $R^{f2}$ is preferably a C1-C6 fluoroalkyl group.

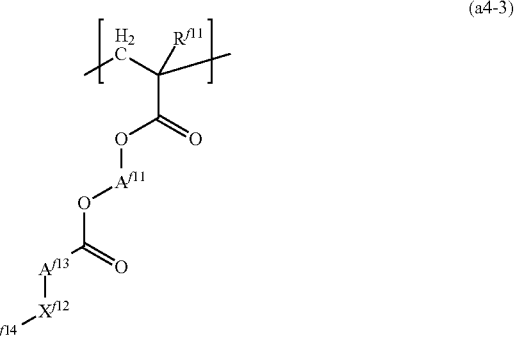

(a4-3)

In formula, $R^{f11}$ represents a hydrogen atom or a methyl group.

$A^{f11}$ represents a C1-C6 alkanediyl group.

$A^{f13}$ represents a C1-C18 divalent saturated hydrocarbon group which may have a fluorine atom.

$X^{f12}$ represents a carbonyloxy group or an oxycarbonyl group.

$A^{f14}$ represents a C1-C17 divalent saturated hydrocarbon group which may have a fluorine atom, provided that one or both of $A^{f13}$ and $A^{f14}$ represents a fluorine-containing saturated hydrocarbon group.

Examples of the alkanediyl group represented by $A^{f11}$ include those as referred to for $A^{f12}$.

As to $A^{f13}$, the divalent saturated hydrocarbon group includes chain saturated hydrocarbon groups, cyclic saturated hydrocarbon groups and combined groups of these groups.

As to $A^{f13}$, the divalent saturated hydrocarbon group which may have a fluorine atom is preferably a divalent saturated chain hydrocarbon group which may have a fluorine atom, more preferably a perfluoroalkanediyl group.

Examples of the divalent aliphatic hydrocarbon group which may have a fluorine atom include an alkanediyl group such as a methyl group, an ethylene group, a propanediyl group, a butanediyl group and pentanediyl group; and a perfluoroalkanediyl group such as a difluoromethylene group, a perfluoroethylene group, a perfluoropropanediyl group, a perfluorobutanediyl group and perfluoropentanediyl group.

The divalent cyclic hydrocarbon group which may have a fluorine atom may be a divalent monocyclic or polycyclic group.

Examples of the divalent monocyclic hydrocarbon group which may have a fluorine atom include a cyclohexanediyl group and a perfluorocyclohexanediyl group.

Examples of the divalent polycyclic hydrocarbon group which may have a fluorine atom include an adamantanediyl group, norbornanediyl group, and a perfluoroadamantanediyl group.

In the group represented by $A^{f14}$, the monovalent saturated hydrocarbon group includes chain saturated hydrocarbon groups, cyclic saturated hydrocarbon groups and combined groups of these saturated hydrocarbon groups.

As to $A^{f14}$, the monovalent aliphatic hydrocarbon group which may have a fluorine atom is preferably a monovalent saturated aliphatic hydrocarbon group which may have a fluorine atom, more preferably a perfluoroalkanediyl group.

Examples of the monovalent aliphatic hydrocarbon group which may have a fluorine atom include a trifluoromethyl group, a fluoromethyl group, a methyl group, a perfluoroethyl group, a 1,1,1-trifluoroethyl group, a 1,1,2,2-tetrafluoroethyl group, an ethyl group, a perfluoropropyl group, a 1,1,1,2,2-pentafluoropropyl group, propyl group, a perfluorobutyl group, 1,1,2,2,3,3,4,4-octafluorobutyl group, a butyl group, a perfluoropentyl group, 1,1,1,2,2,3,3,4,4-nonafluoropentyl group, a pentyl group, a hexyl group, a perfluorohexyl group, a heptyl group, a perfluoroheptyl group, an octyl group and a perfluorooctyl group.

The monovalent cyclic hydrocarbon group which may have a fluorine atom may be monocyclic or polycyclic monovalent group.

Examples of the monovalent monocyclic cyclic hydrocarbon group which may have a fluorine atom include a cyclopropyl group, cyclopentyl group, cyclohexyl group, and perfluorocyclohexyl group.

Examples of the monovalent polycyclic hydrocarbon group which may have a fluorine atom include an adamantyl group, a norbornyl group, and a perfluoroadamantyl group.

Examples of the combined groups of the above-mentioned aliphatic hydrocarbon group include a cyclopropylmethyl group, a cyclobutylmethyl group, an adamantylmethyl group, a norbornylmethyl group and a perfluoroadamantylmethyl group.

In formula (a4-3), $A'^{11}$ is preferably an ethylene group.

The divalent aliphatic hydrocarbon group represented by $A'^{13}$ has preferably 6 or less, more preferably 2 to 3, of carbon atoms.

The monovalent aliphatic hydrocarbon group represented by $A'^{14}$ has preferably 3 to 12, more preferably 3 to 10, of carbon atoms.

$A'^{14}$ has preferably a C3-C12 monovalent alicyclic hydrocarbon group, more preferably a cyclopropylmethyl group, a cyclopentyl group, a cyclohexyl group, a norbornyl group or an adamantyl group.

Examples of the structural unit of formula (a4-2) include preferably those represented by formulae (a4-1-1) to (a4-1-22).

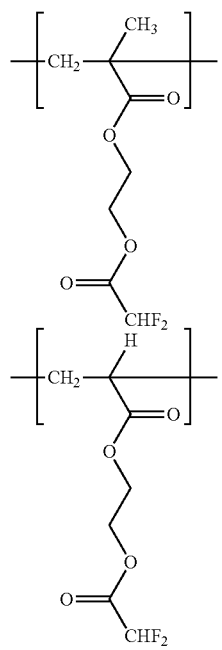

(a4-1-1)

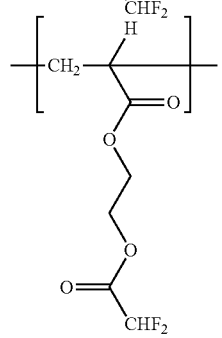

(a4-1-2)

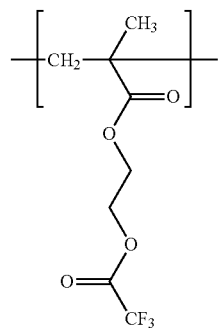

(a4-1-3)

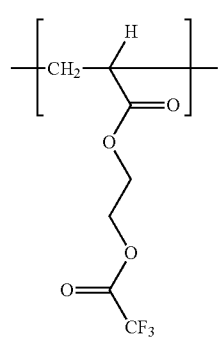

(a4-1-4)

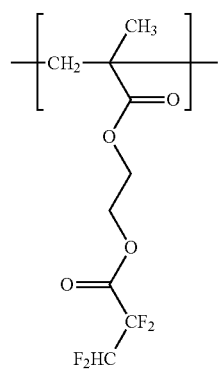

(a4-1-5)

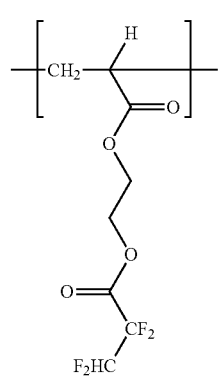

(a4-1-6)

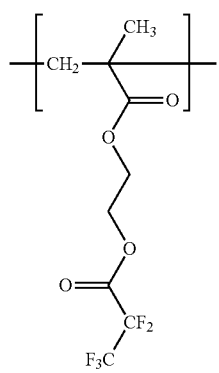
(a4-1-7)
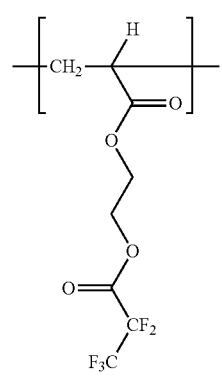
(a4-1-8)
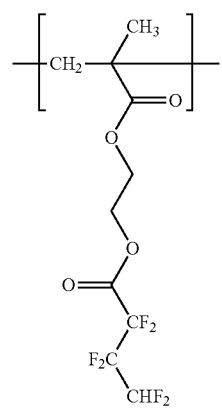
(a4-1-9)
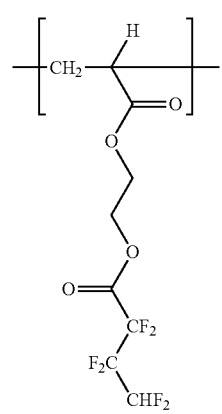
(a4-1-10)
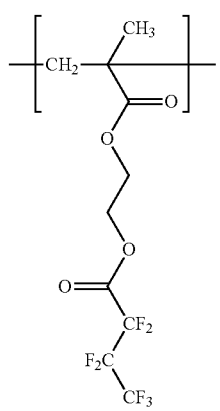
(a4-1-11)
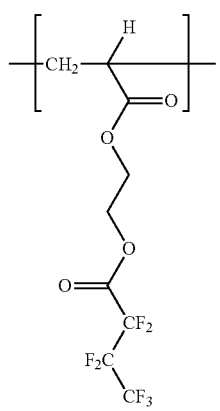
(a4-1-12)
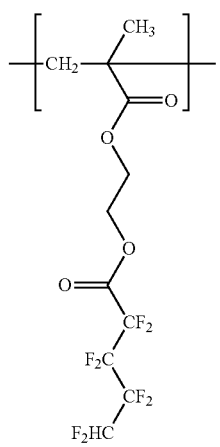
(a4-1-13)

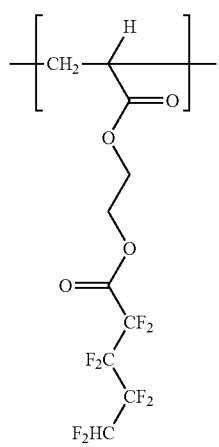
(a4-1-14)
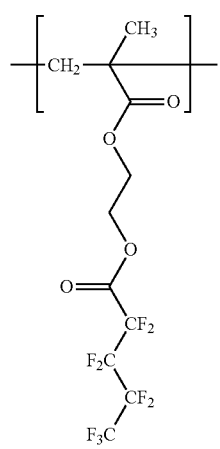
(a4-1-15)
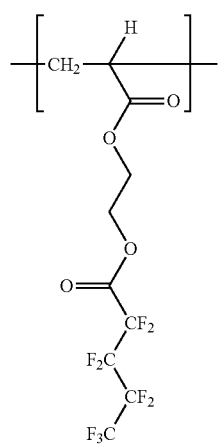
(a4-1-16)
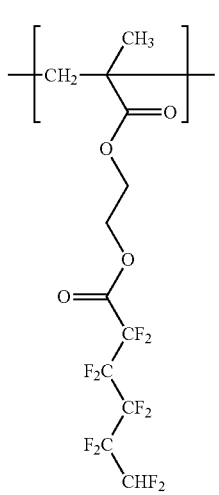
(a4-1-17)
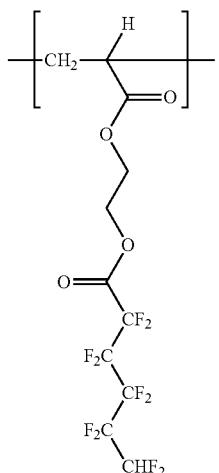
(a4-1-18)
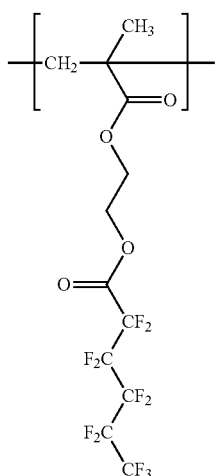
(a4-1-19)

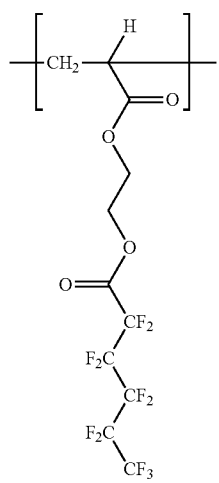 (a4-1-20)
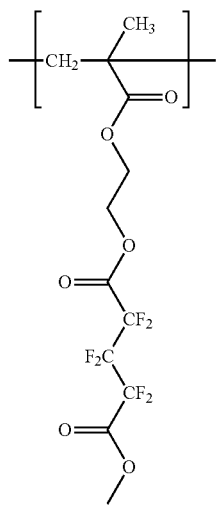 (a4-1'-1)
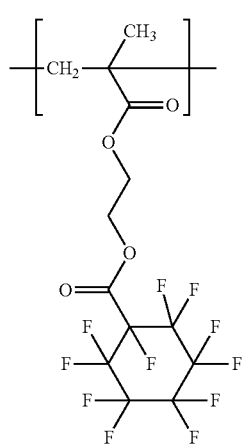 (a4-1-21)
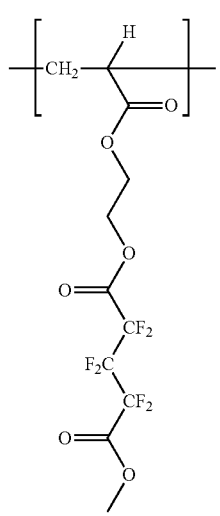 (a4-1'-2)
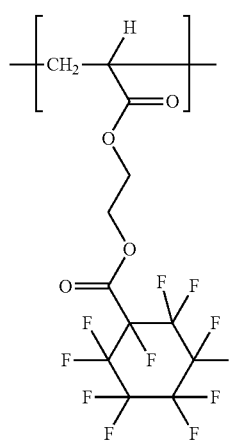 (a4-1-22)
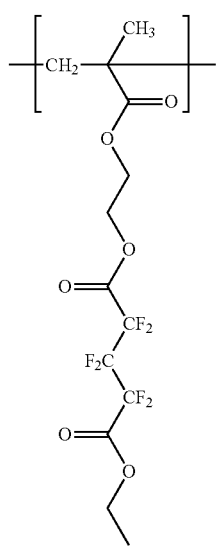 (a4-1'-3)
Examples of the structural unit represented by formula (a4-3) include preferably those represented by formulae (a4-1'-1) to (a4-1'-22)

(a4-1'-4)
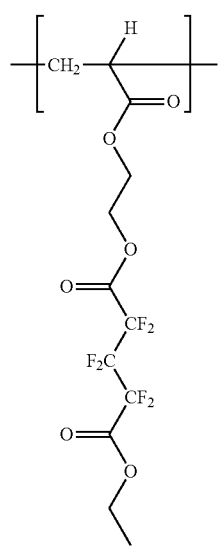
(a4-1'-5)
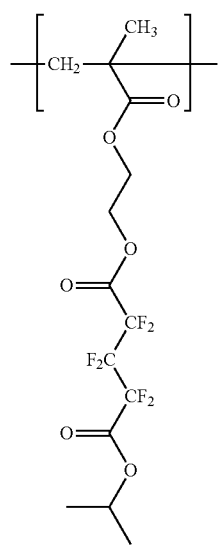
(a4-1'-6)
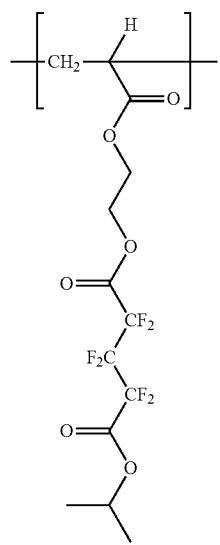
(a4-1'-7)
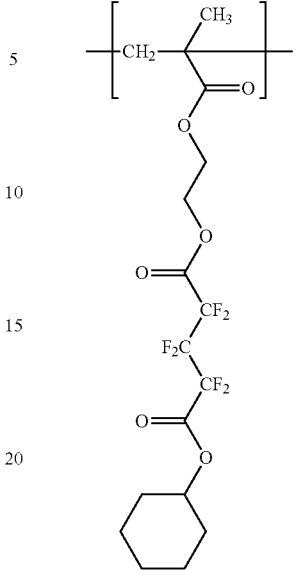
(a4-1'-8)
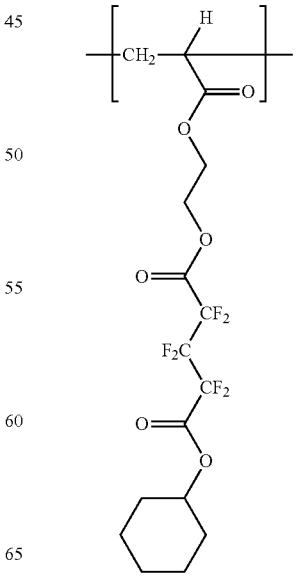

(a4-1'-9)
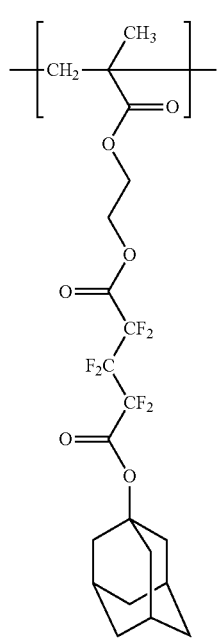
(a4-1'-11)
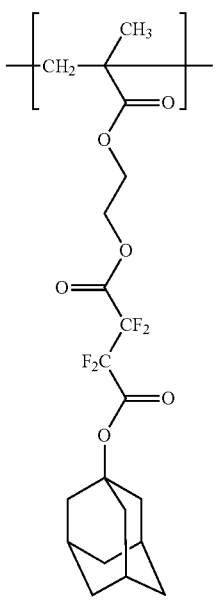
(a4-1'-10)
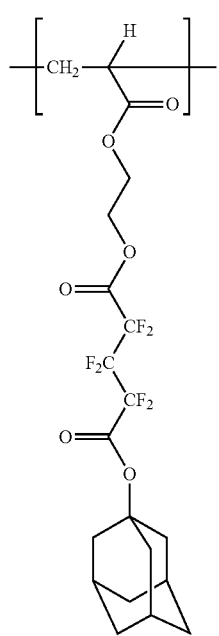
(a4-1'-12)
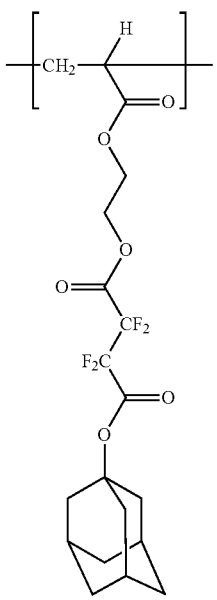

(a4-1'-13)
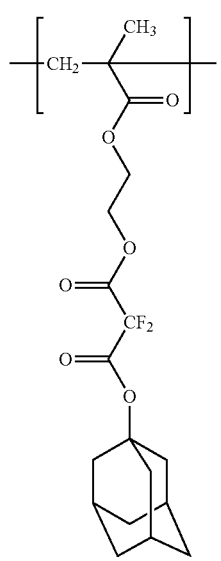
(a4-1'-15)
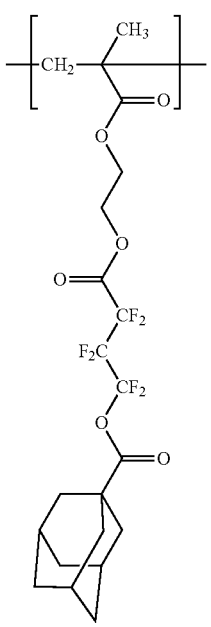
(a4-1'-14)
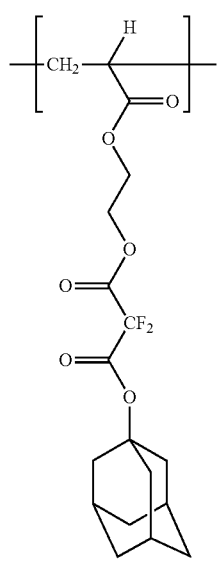
(a4-1'-16)
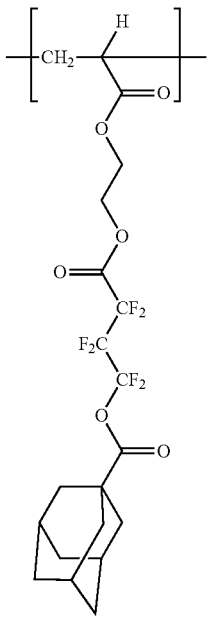

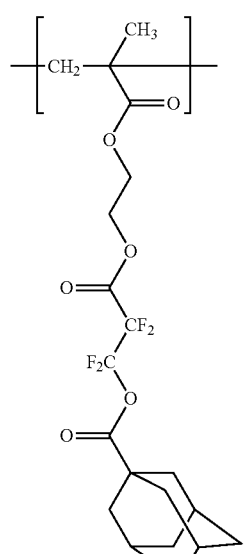 (a4-1'-17)
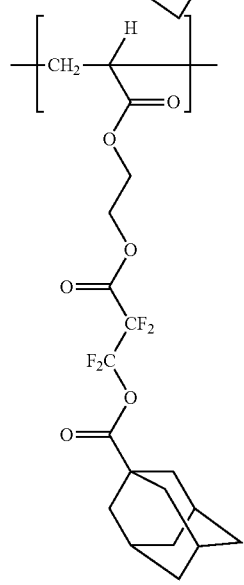 (a4-1'-18)
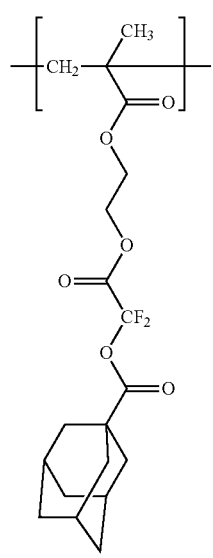 (a4-1'-19)
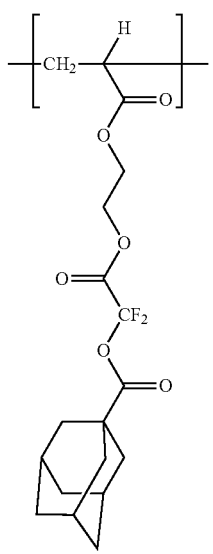 (a4-1'-20)
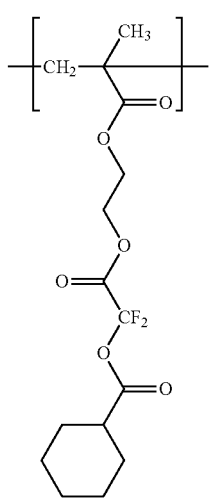 (a4-1'-21)
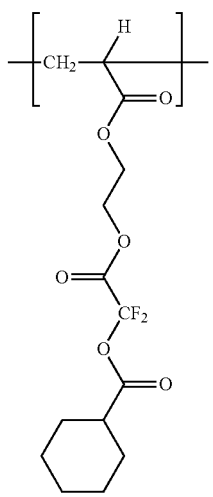 (a4-1'-22)

Another example of the structural unit (a4) includes those represented by formula (a4-4)

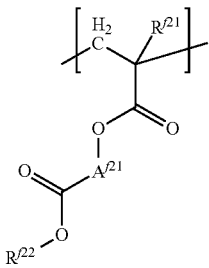
(a4-4)

In formula (a4-4), wherein $R^{/21}$ represents a hydrogen atom or a methyl group;

$A^{/21}$ represents —$(CH_2)_{j1}$—, —$(CH_2)_{j2}$—O—$(CH_2)_{j3}$— or —$(CH_2)_{j4}$—CO—O—$(CH_2)_{j5}$— where j1, j2, j3, j4 or j5 each independently represent an integer of 1 to 6; and $R^{/22}$ represents a C1-C10 monovalent hydrocarbon group having a fluorine atom.

For $R^{/22}$, examples of monovalent hydrocarbon group having a fluorine atom include those as referred to for $R^{/22}$.

$R^{/22}$ is preferably a C1-C10 monovalent alkyl group having a fluorine atom or a C3-C10 monovalent alicyclic hydrocarbon group having a fluorine atom, more preferably a C1-C10 monovalent alkyl group having a fluorine atom, and still more preferably a C1-C6 monovalent alkyl group having a fluorine atom.

In formula (a4-4), $A^{/21}$ is preferably —$(CH_2)_{j1}$—, more preferably a methylene or ethylene group, and still more preferably a methylene group.

Examples of the structural unit (a4-4) include preferably the following ones.

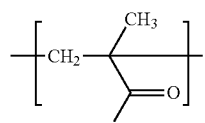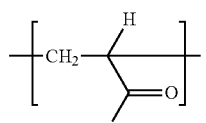

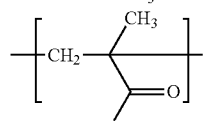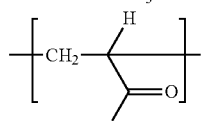

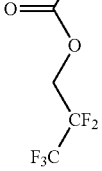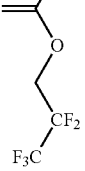

-continued

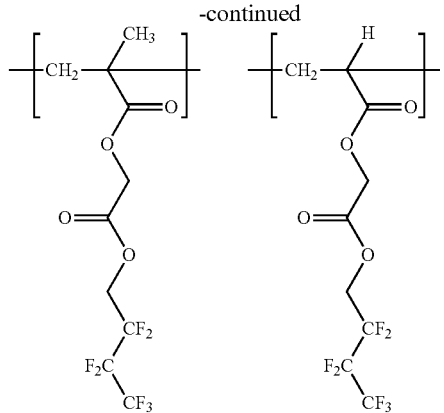

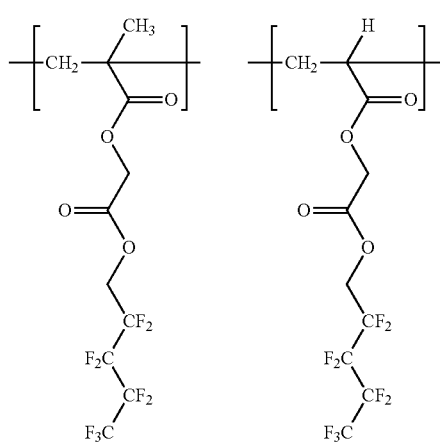

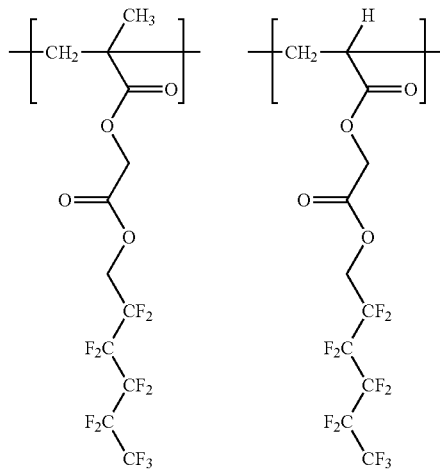

123
-continued
124
-continued
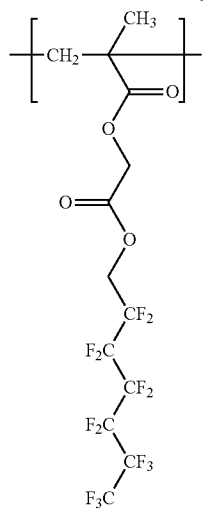
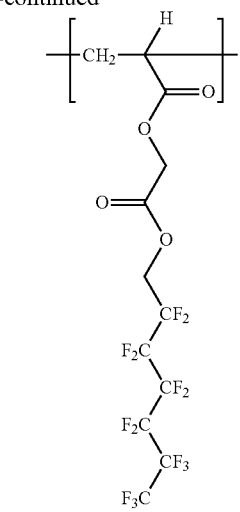
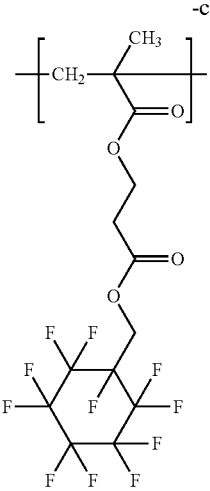
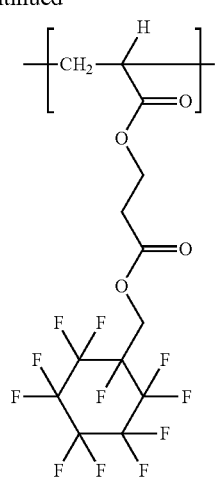

-continued

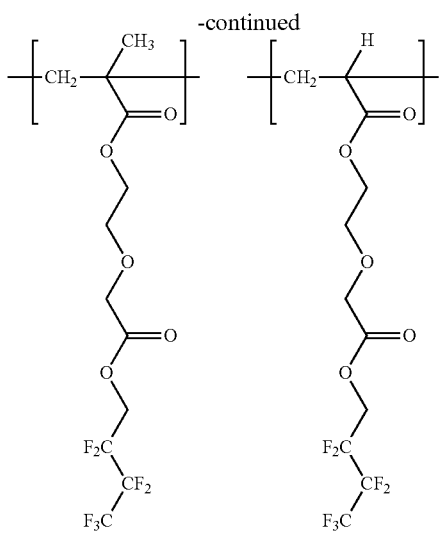

When Resin (A) comprises the structural unit represented by formula (a4), its content is preferably 1 to 20% by mole, more preferably 2 to 15% by mole and still more preferably 3 to 10% by mole based on 100% by mole of all the structural units of the resin.

Other examples of the structural unit having no acid-labile group include one having an acid-stable hydrocarbon group.

Herein, the term "acid-stable hydrocarbon group" means such a hydrocarbon group that is not removed from the structural unit having the group by action of an acid generated from an acid generator as described later.

The acid-stable hydrocarbon group may be a linear, branched or cyclic hydrocarbon group.

The structural unit which has a hydrocarbon not being removed therefrom by action of an acid may have a linear, branched or cyclic hydrocarbon, preferably an alicyclic hydrocarbon group.

Examples of the structural unit having an acid-stable hydrocarbon group include one represented by formula (a5-1):

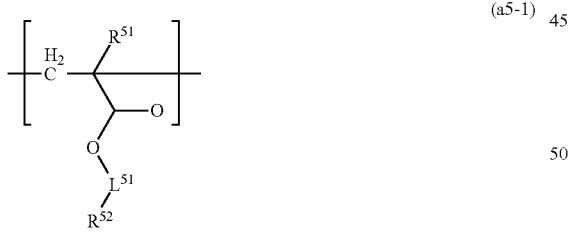

(a5-1)

where $R^{51}$ represents a hydrogen atom or a methyl group; $R^{52}$ represents a C3-C18 monovalent alicyclic hydrocarbon group which may have a C1-C8 monovalent aliphatic hydrocarbon group as a substituent, provided that the alicyclic hydrocarbon group has no substituent on the carbon atom bonded to $L^{51}$; and
$L^{51}$ represents a single bond or a C1-C18 divalent saturated hydrocarbon group where a methylene group can be replaced by an oxygen atom or carbonyl group.

The alicyclic hydrocarbon group represented by $R^{52}$ may be monocyclic or polycyclic one.

Examples of the alicyclic hydrocarbon group include a monocyclic hydrocarbon group such as a C3-C18 cycloalkyl group (e.g. a cyclopropyl group, a cyclobutyl group, a cyclopentyl group, a cyclohexyl group) and a polycyclic alicyclic hydrocarbon group such as an adamantyl group, or a norbornyl group.

Examples of the aliphatic hydrocarbon group include an alkyl groups such as a methyl group, an ethyl group, n-propyl group, isopropyl group, n-butyl group, sec-butyl group, tert-butyl group, a pentyl group, a hexyl group, an octyl group and 2-ethylhexyl group.

Examples of the alicyclic hydrocarbon group having a substituent include a 3-hydroxyadamantyl group, and a 3-methyladamantyl group. $R^{52}$ is preferably a C3-C18 unsubstituted alicyclic hydrocarbon group, more preferably an adamantyl group, a norbornyl group or a cyclohexyl group.

Examples of the divalent saturated hydrocarbon group represented by $L^{51}$ include divalent aliphatic hydrocarbon groups and divalent alicyclic hydrocarbon groups, preferably divalent aliphatic hydrocarbon groups.

Examples of divalent aliphatic hydrocarbon groups include alkanediyl groups such as a methylene group, an ethylene group, a propanediyl group, a butanediyl group and a pentanediyl group.

The divalent alicyclic hydrocarbon groups may be monocyclic or polycyclic one.

Examples of divalent monocyclic hydrocarbon groups include cycloalkanediyl groups such as a cyclopentanediyl group and a cyclohexanediyl group. Examples of divalent polycyclic alicyclic hydrocarbon groups include an adamantanediyl group and a norbornanediyl group.

Examples of the divalent hydrocarbon group where a methylene group has been replaced by an oxygen atom or carbonyl group include those represented by formulae (L1-1) to (L1-4).

 (L1-1)

 (L1-2)

 (L1-3)

 (L1-4)

In these formulae, * represents a binding position to an oxygen atom.

$X^{x1}$ is a carbonyloxy group or an oxycarbonyl group; and $L^{x1}$ is a C1-C16 divalent saturated hydrocarbon group, and $L^{x2}$ is a single bond or a C1-C15 divalent aliphatic saturated hydrocarbon group, provided that the total number of the carbon atoms in $L^{x1}$ and $L^{x2}$ is 16 or less.

$L^{x3}$ is a C1-C17 divalent saturated hydrocarbon group, and $L^{x4}$ is a single bond or a C1-C16 divalent aliphatic saturated hydrocarbon group, provided that the total number of the carbon atoms in $L^{x3}$ and $L^{x4}$ is 17 or less.

$L^{x5}$ is a C1-C15 divalent saturated hydrocarbon group, and $L^{x6}$ and $L^{x7}$ are a single bond or a C1-C14 divalent aliphatic saturated hydrocarbon group, provided that the total number of the carbon atoms in $L^{x5}$, $L^{x6}$ and $L^{x7}$ is 15 or less.

$L^{x8}$ and $L^{x9}$ are each independently a single bond or a C1-C12 divalent aliphatic saturated hydrocarbon group, and $W^{x1}$ is a C3-C15 divalent cyclic saturated hydrocarbon group, provided that the total number of the carbon atoms in $L^{x8}$, $L^{x9}$ and $W^{x1}$ is 15 or less.

$L^{x1}$ is preferably a C1-C8 divalent saturated hydrocarbon group, more preferably a methylene group or an ethylene group.

$L^{x2}$ is preferably a single bond, or a C1-C8 divalent saturated hydrocarbon group, more preferably a single bond.

$L^{x3}$ is preferably a C1-C8 divalent saturated hydrocarbon group, more preferably a methylene group or an ethylene group.

$L^{x4}$ is preferably a single bond or a C1-C8 divalent saturated hydrocarbon group, more preferably a single bond, a methylene group or an ethylene group.

$L^{x5}$ is preferably a C1-C8 divalent saturated hydrocarbon group, more preferably a methylene group or an ethylene group.

$L^{x6}$ is preferably a single bond or a C1-C8 divalent saturated hydrocarbon group, more preferably a methylene group or an ethylene group.

$L^{x7}$ is preferably a single bond or a C1-C8 divalent saturated hydrocarbon group, more preferably a methylene group or an ethylene group.

$L^{x8}$ is preferably a single bond or a C1-C8 divalent saturated hydrocarbon group, more preferably a single bond or a methylene group.

$L^{x9}$ is preferably a single bond or a C1-C8 divalent saturated hydrocarbon group, more preferably a single bond or a methylene group.

$W^{x1}$ is a preferably C3-C10 divalent cyclic saturated hydrocarbon group, more preferably a cyclohexanediyl group or an adamantanediyl group.

Examples of the divalent hydrocarbon group represented by formula (L1-1) include the following ones.

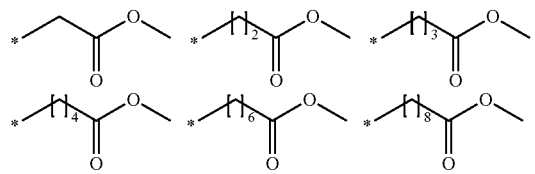
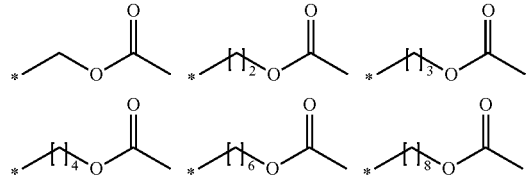
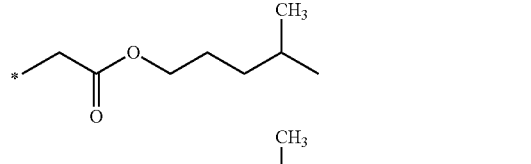
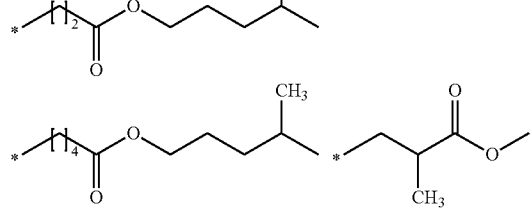

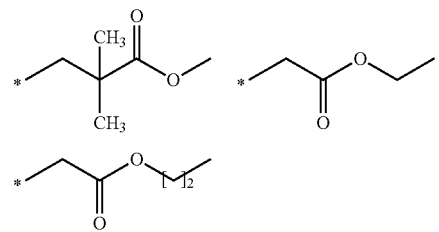

In these formulae, * represents a binding position to an oxygen atom.

Examples of the divalent hydrocarbon group represented by formula (L1-2) include the following ones.

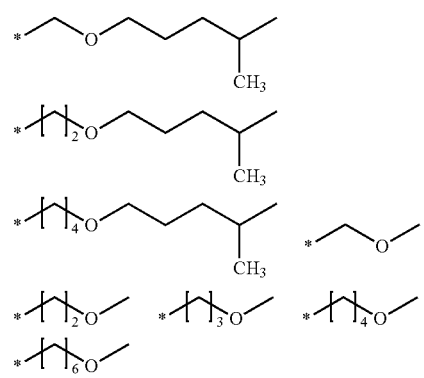

In these formulae, * represents a binding position to an oxygen atom.

Examples of the divalent hydrocarbon group represented by formula (L1-3) include the following ones.

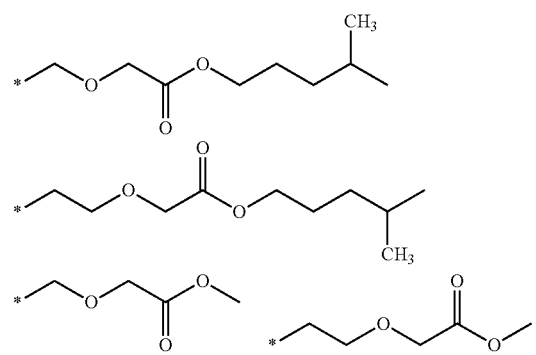

In these formulae, * represents a binding position to an oxygen atom.

Examples of the divalent hydrocarbon group represented by formula (L1-4) include the following ones.

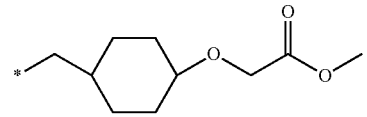

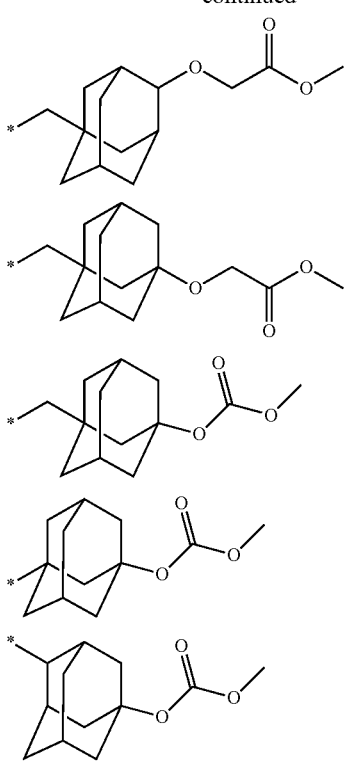
In these formulae, * represents a binding position to an oxygen atom.
$L^{51}$ is preferably a single bond or a group represented by formula (L1-1).
Examples of the structural unit represented by formula (a5-1) include the following ones and those where a methyl group has been replaced by a hydrogen atom in each formula.
(a5-1-1)
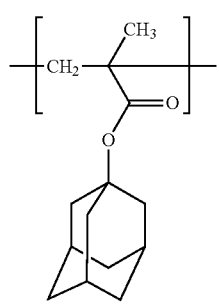
(a5-1-2)
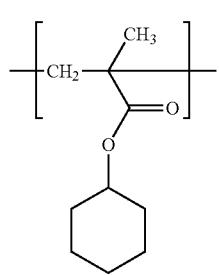
(a5-1-3)
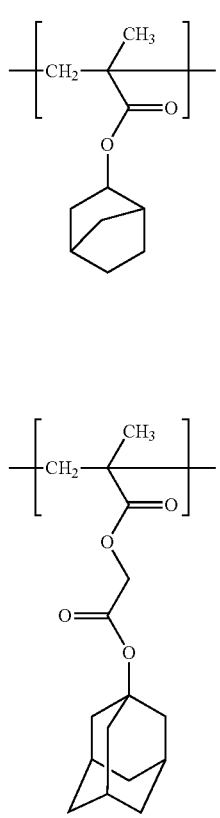
(a5-1-4)
(a5-1-5)
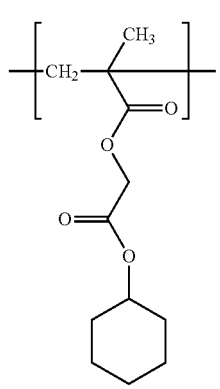
(a5-1-6)
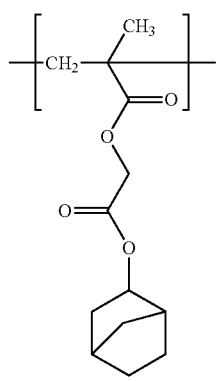

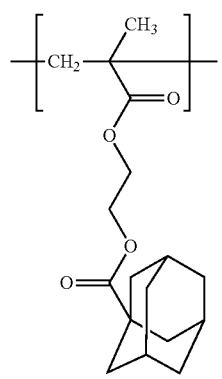 (a5-1-7)
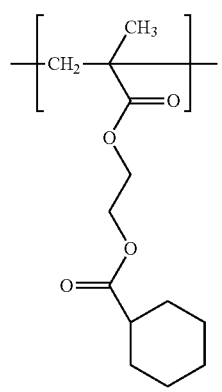 (a5-1-8)
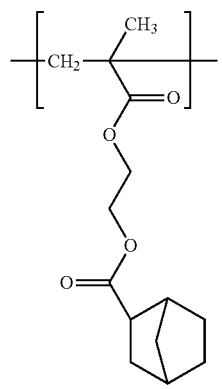 (a5-1-9)
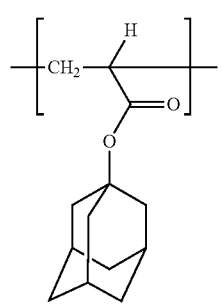 (a5-1-10)
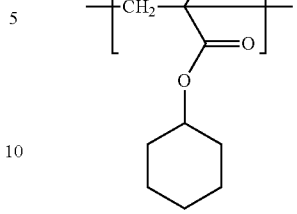 (a5-1-11)
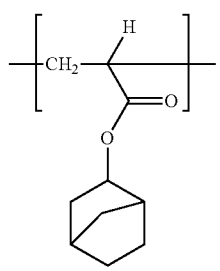 (a5-1-12)
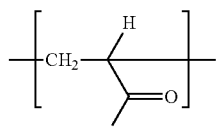 (a5-1-13)
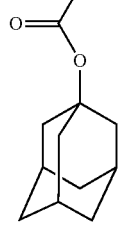 
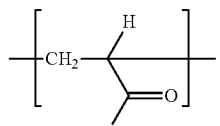 (a5-1-14)

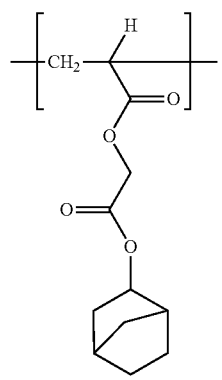
(a5-1-15)
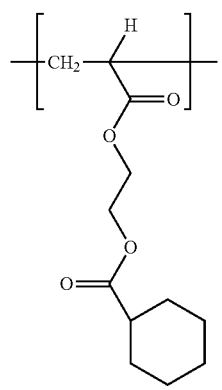
(a5-1-16)
(a5-1-17)
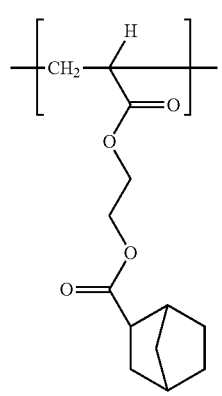
(a5-1-18)
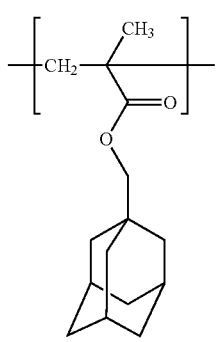
(a5-1-19)
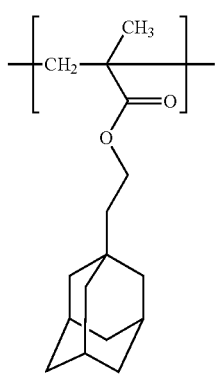
(a5-1-20)
(a5-1-21)
(a5-1-22)

(a5-1-23) 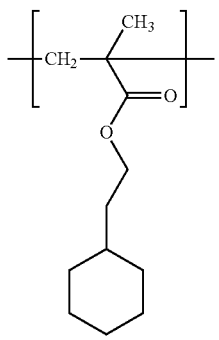

(a5-1-24) 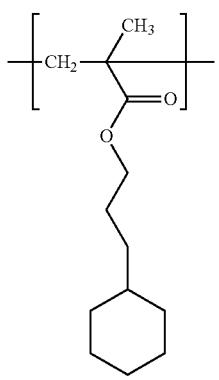

(a5-1-25) 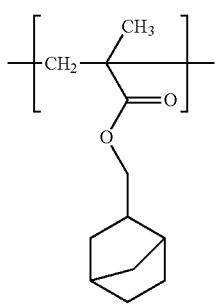

(a5-1-26) 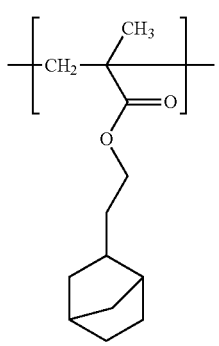

(a5-1-27) 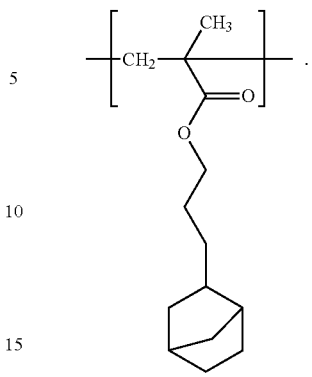

Resin (A) comprises preferably the structural unit (a1) and the structural unit having no acid-labile group.

In Resin (A), the structural unit (a1) is one of the structural unit (a1-1) and the structural unit (a1-2), more preferably the structural unit (a1-2). The structural unit (a1-2) is preferably which comprises a cyclohexyl group or a cyclopentyl group.

The structural unit having no acid-labile group is preferably one of the structural unit (a2) and the structural unit (a3). The structural unit (a2) is preferably the structural unit (a2-1). The structural unit (a3) is preferably one of the structural unit (a3-1), the structural unit (a3-2) and the structural unit (a3-4). Resin (A) comprises preferably the structural unit (a1) derived from a structural unit having an adamantyl group, preferably structural unit (a1-1). The content of the structural unit having an adamantyl group is preferably 15% by mole or more of the total amount of the structural unit (a1). The more is the structural unit having an adamantyl group, the more improved is the resistance of the photoresist film to dry etching.

Resin (A) can be produced according to known polymerization methods such as radical polymerization.

The resin has usually 2,000 or more of the weight-average molecular weight, preferably 2,500 or more of the weight-average molecular weight, more preferably 3,000 or more of the weight-average molecular weight. The resin has usually 50,000 or less of the weight-average molecular weight, preferably more 30,000 or less of the weight-average molecular weight, and preferably more 15,000 or less of the weight-average molecular weight.

The weight-average molecular weight can be measured with gel permeation chromatography.

Examples of another resin than Resin (A) include what consists of structural units having no acid-labile group, preferably what comprises, not the structural unit (a1), but the structural unit having a fluorine atom. Here, such another resin is referred to as "Resin (X)".

Resin (X) may be one which consists of the structural unit having a fluorine atom, or one which further comprise the structural unit (a2), the structural unit (a3) or another structural unit having no acid-labile group, known in the art.

In Resin (X), the content of the structural unit having a fluorine atom is preferably 40% by mole or more, more preferably 45% by mole or more, still more preferably 50% by mole or more, based on sum of the structural units in the resin.

Resin (X) usually has 8000 or more of the weight-average molecular weight, preferably 10000 or more of the weight-average molecular weight. The resin usually has 80,000 or less of the weight-average molecular weight, preferably has 60,000 or less of the weight-average molecular weight.

The weight-average molecular weight can be measured with known methods such as liquid chromatography or gas chromatography.

When the photoresist composition comprises Resin (X), the content of the resin is preferably 1 to 60 weight parts, more preferably 1 to 50 weight parts, and still more preferably 1 to 40 weight parts, and further still more preferably 2 to 30 weight parts, relative to 100 parts of Resin (A).

The total content of the resins in the photoresist composition of the present invention is usually 80% by mass or more based on sum of solid component, and usually 99% by mass or less.

In this specification, "solid component" means components other than solvent in the photoresist composition.

The photoresist composition of the present invention may comprise a solvent.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention. The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the present invention may further comprise a quencher such as a basic compound. The "quencher" has the property that it can trap an acid, especially an acid generated from the acid generator by applying a radiation.

Examples of the quencher include a basic nitrogen-containing organic compound and a salt which generates an acid having acidity weaker than an acid generated from Salt (a) or the above-mentioned known acid generators.

Examples of the basic nitrogen-containing organic compound include an amine compound such as an aliphatic amine, an aromatic amine and an ammonium salt. Examples of the aliphatic amine include a primary amine, a secondary amine and a tertiary amine. Examples of the aromatic amine include an aromatic amine.

Examples of the quencher include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, 2 tris[2-(2-methoxyethoxy)ethyl] amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenyl methane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy) ethane, di(2-pyridyl) ketone, 4,4'-dipyridyl sulfide, 4,4'-dipyridyl disulfide, 2,2'-dipyridylamine, 2,2'-dipicolylamine and bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

Herein, the acidity in the salts is shown by the acid dissociation constant (pKa).

The acid dissociation constant of acid generated from the salt for a quencher is usually a salt of $-3<pKa$.

The salt for a quencher is preferably a salt of $-1<pKa<7$, and more preferably a salt of $0<pKa<5$.

Specific examples of the salt for a quencher include the following ones, the salt of formula (D), and salts recited in US2012/328986A1, US2011/171576A1, US2011/201823A1, JP2011-39502A1, and US2011/200935A1.

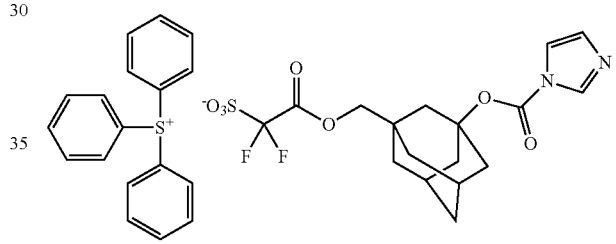

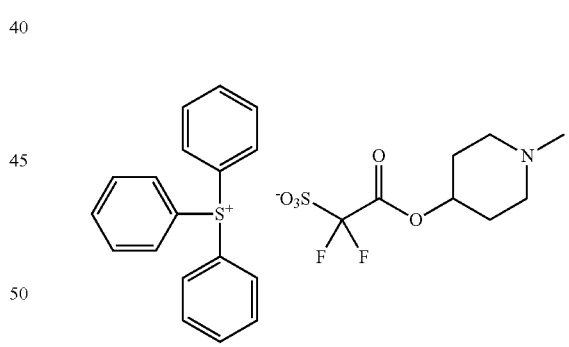

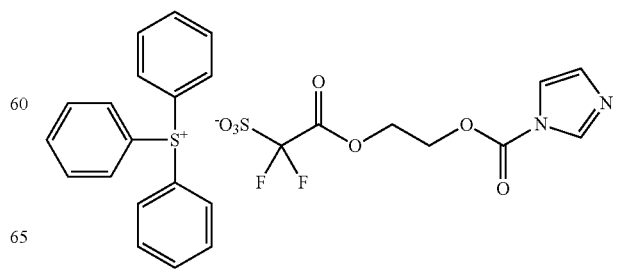

-continued

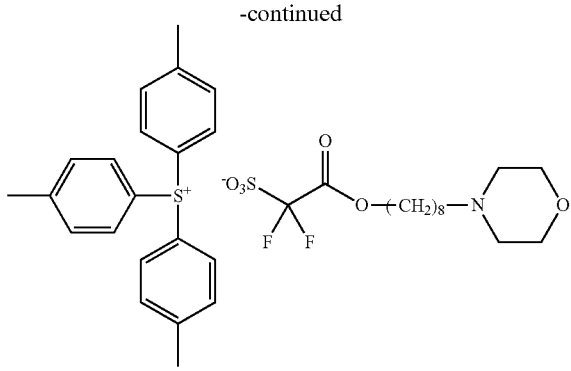

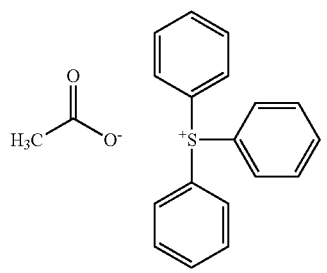

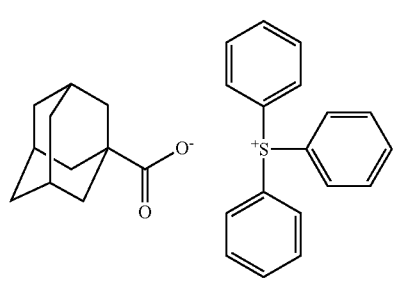

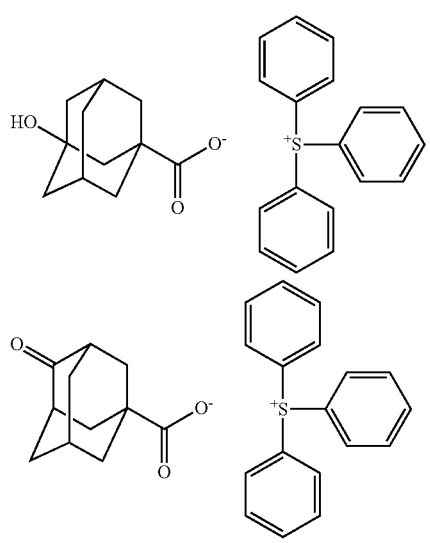

-continued

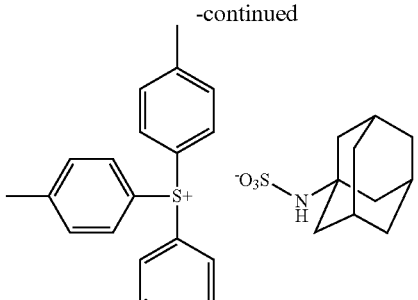

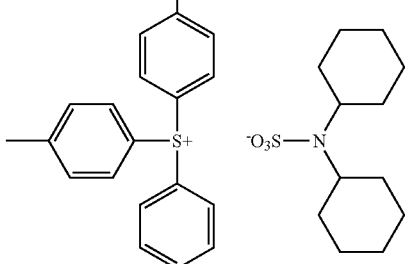

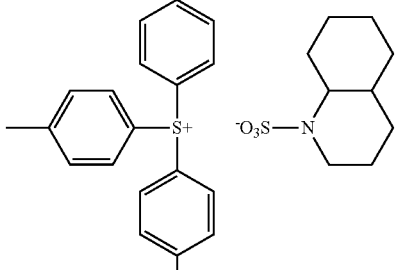

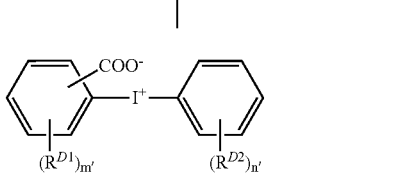

(D)

In formula (D), $R^{D1}$ and $R^{D2}$ respectively represent a C1-C12 monovalent hydrocarbon group, a C1-C6 alkoxy group, a C2-C7 acyl group, a C2-C7 acyloxy group, a C2-C7 alkoxycarbonyl group, a nitro group or a halogen atom.

The symbols m' and n' each independently represent an integer of 0 to 4.

The hydrocarbon group represented by $R^{D1}$ and $R^{D2}$ includes a C1-C12 alkyl group, a C3-C12 monovalent alicyclic hydrocarbon group, a C6-C12 monovalent aromatic hydrocarbon group, and any combination of them.

Examples of the monovalent hydrocarbon group include alkyl groups such as a methyl group, an ethyl group, n-propyl group, an isopropyl group, n-butyl group, sec-butyl group, tert-butyl group, a pentyl group, a hexyl group, a heptyl group, an octyl group, a nonyl group. Examples of the alicyclic hydrocarbon group, which may be a monocyclic or polycyclic one, include cycloalkyl groups such as a cyclopropyl group, a cyclobutyl group, a cyclopentyl group, a cyclohexyl group, a cycloheptyl group, a cyclooctyl group, a cycloheptyl group, a cyclodecyl group, and norbonyl group and adamantyl group.

Examples of the aromatic hydrocarbon group include an aryl group such as a phenyl group, a 1-naphthyl group, a 2-naphthyl group, a 2-methylphenyl group, a 3-methylphenyl group, 4-methylphenyl group, a 4-ethylphenyl group, a 4-propylphenyl group, a 4-isopropylphenyl group, a 4-butylphenyl group, a 4-t-butylphenyl group, a 4-hexylphenyl group, a 4-cyclohexylphenyl group, an anthryl group, a p-adamantylphenyl group, a tolyl group, a xylyl group, a cumenyl group, a mesityl group, a biphenyl group, a phenanthryl group, a 2,6-diethylphenyl group and a 2-methyl-6-ethylphenyl group. Examples of the combination include alkyl-cycloalkyl groups, cycloalkyl-alkyl groups, aralkyl groups such as a benzyl group, a 1-phenylethyl group, a 2-phenylethyl group, a 1-phenyl-1-propyl group, a 1-phenyl-2-propyl group, a 2-phenyl-2-propyl group, a 3-phenyl-1-propyl group, a 4-phenyl-1-butyl, a 5-phenyl-1-pentyl group and 6-phenyl-1-hexyl group.

Examples of alkoxy groups include a methoxy group and an ethoxy group.

Examples of acyl groups include an acetyl group, a propanoyl group, a benzoyl group, a cyclohexanecarbonyl group.

Examples of acyloxy group include groups where an oxy group [—O-] is attached to any one of the acyl groups as mentioned above.

Examples of alkoxycarbonyl group include groups where a carbonyl group [—CO-] is attached to any one of the alkoxy groups as mentioned above.

Examples of halogen atoms include fluorine atoms, a chlorine atom, and a bromine atom.

Examples of the compounds of formula (D) include the following ones.

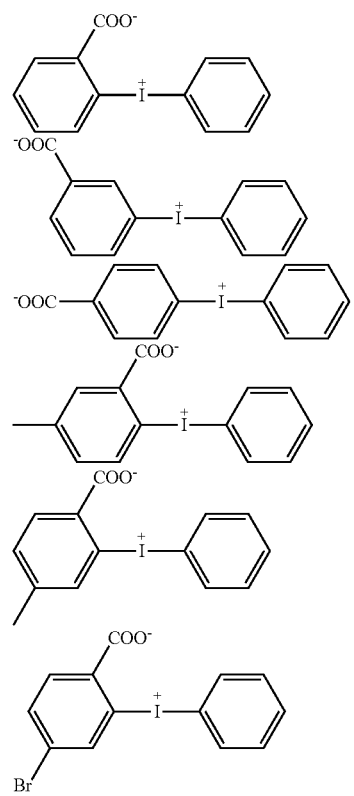

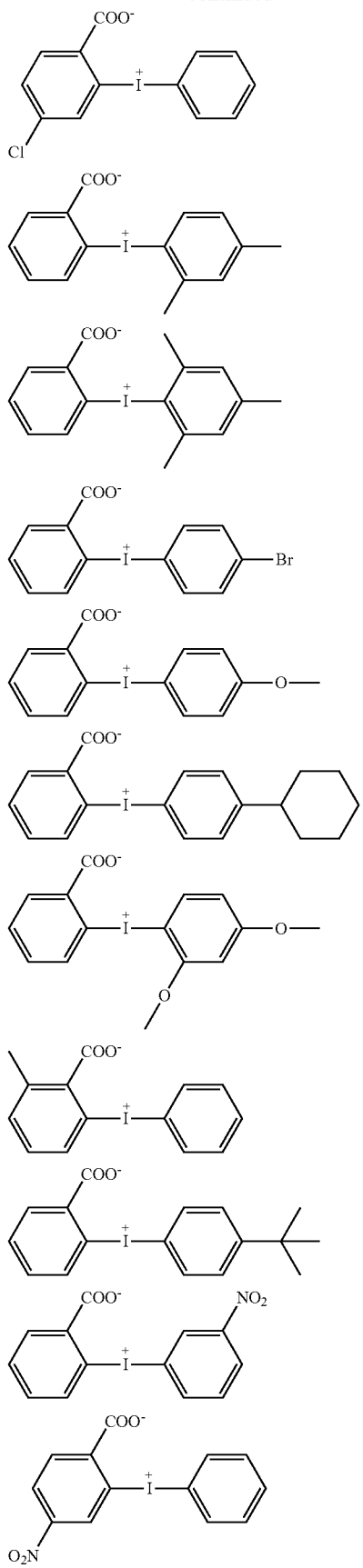

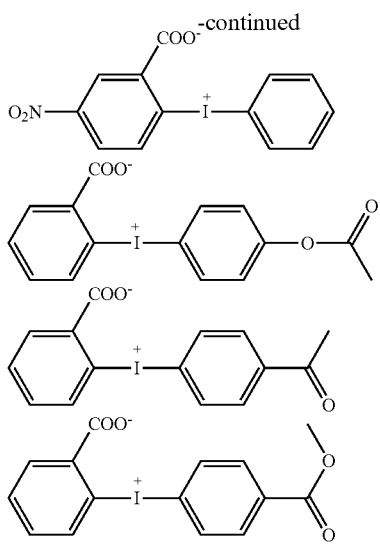

The content of quencher is preferably 0.01 to 5% by mass, more preferably 0.01 to 3% by mass, and still more preferably 0.01 to 1% by mass, based on sum of solid component.

The photoresist compositions of the present invention may comprise, if necessary, a small amount of various additives such as a sensitizer, a dissolution inhibitor, other polymers, a surfactant, a stabilizer and a dye as long as the effect of the present invention is not prevented.

The photoresist compositions of the present invention can usually be prepared by mixing, in a solvent, Salt (I) and Resin (A), and if necessary a known acid generator, a quencher, and/or additives at a suitable ratio for the composition, optionally followed by filtrating the mixture with a filter having 0.003 μm to 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the present invention are useful for a chemically amplified photoresist composition.

The photoresist compositions of the present invention are useful for a chemically amplified photoresist composition.

A photoresist pattern can be produced by the following steps (1) to (5):

(1) a step of applying the photoresist composition of the present invention on a substrate,
(2) a step of forming a composition film by conducting drying,
(3) a step of exposing the composition film to radiation,
(4) a step of baking the exposed composition film, and
(5) a step of developing the baked composition film with an alkaline developer.

The applying of the photoresist composition on a substrate is usually conducted using a conventional apparatus such as spin coater. The photoresist composition is preferably filtrated with filter having a pore size of 0.01 to 0.2 μm before applying. Examples of the substrate include a silicon wafer or a quartz wafer on which a sensor, a circuit, a transistor or the like is formed.

The formation of the composition film is usually conducted using a heating apparatus such as hot plate or a decompressor, and the heating temperature is usually 50 to 200° C. When the pressure is reduced during heating, the operation pressure is usually 1 to $1.0*10^5$ Pa. The heating time is usually 10 to 180 seconds.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed composition film is usually 50 to 200° C., and preferably 70 to 150° C.

The development of the baked composition film is usually carried out using a development apparatus. The development method includes dipping methods, paddle methods, spray methods and dynamic dispense method. The developing temperature is preferably 5 to 60° C., and the developing time is preferably 5 to 300 seconds.

The positive and negative type photoresist patterns can be obtained by the development depending on a developer to be used therefor.

When a positive type photoresist pattern is prepared from the photoresist composition of the present invention, the development can be conducted with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The alkaline developer may comprise a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the present invention, the development can be conducted with a developer containing an organic solvent, such developer is sometimes referred to as "organic developer".

Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 50% to 100% by weight, more preferably from 90% to 100% by weight. Preferred is that the organic developer essentially consists of butyl acetate and/or 2-heptanone.

The organic developer may comprise a surfactant or a very small amount of water.

Development with an organic developer can be stopped by replacing the developer by other solvent than it such as alcohol.

The photoresist composition of the present invention is suitable for KrF excimer laser lithography, ArF excimer laser lithography, EUV (extreme ultraviolet) lithography, EUV immersion lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on amass basis unless otherwise specifically noted.

The weight-average molecular weight of any material used in the following examples was determined with gel permeation chromatography under the following condition.

Equipment: HLC-8120 GCP type, manufactured by TOSOH CORPORATION

Column: Three of TSKgel Multipore HXL-M with guard column, manufactured by TOSOH CORPORATION Solvent: tetrahydrofuran Flow rate: 1.0 mL/min.

Detector: RI Detector

Column temperature: 40° C.

Injection volume: 100 μL

Standard reference material: Standard polystyrene (manufactured by TOSOH CORPORATION)

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Here, the values at the peaks of the spectrum are referred to as "MASS."

Example 1

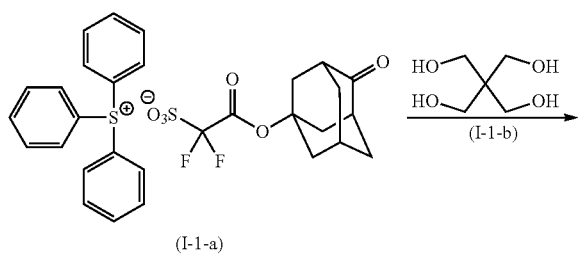

(I-1-a)

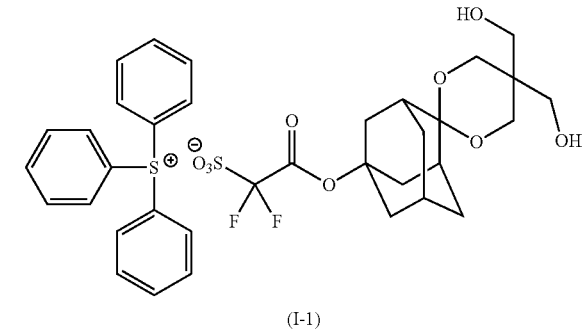

(I-1)

The salt represented by formula (I-1-a) was prepared in the manner of the method according to JP2007-224008A1.

To a reactor, 7 parts of the salt represented by formula (I-1-a), 6.5 parts of the compound represented by formula (I-1-b), 35 parts of chloroform, 14 parts of acetonitrile and 14 parts of dimethylformamide were added and then they were stirred at 23° C. for 30 minutes.

To the resultant mixture, 0.07 parts of p-toluenesulfonic acid were added, and then refluxed and stirred for 3 hours.

Then the obtained reaction mixture was cooled to 23° C., and 155 parts of chloroform were added thereto and stirred, followed by being filtrated.

To the collected filtrate, 40 parts of 5% aqueous potassium carbonate solution were fed thereinto, followed by stirring at 23° C. for 30 minutes. Then the mixture was set still and separated into an organic phase.

To the organic phase, 45 parts of ion-exchanged water were fed, stirred at 23° C. for 30 minutes, followed by separating into an organic phase therefrom for washing: The washing step was conducted three times.

After washing, to the obtained organic phase, 95 parts of ethyl acetate were added and stirred, followed by removing its supernatant therefrom. The obtained residues were dissolved in acetonitrile and concentrated to obtain 4.38 parts of the compound represented by formula (I-1).

MS (ESI(+) Spectrum): M$^+$ 263.1
MS (ESI(−) Spectrum): M$^-$ 441.1

Example 2

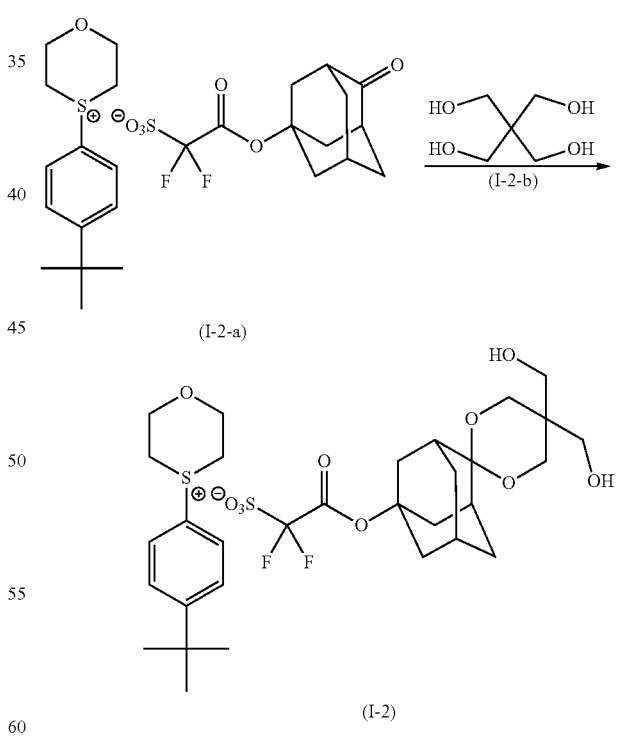

The salt represented by formula (I-2-a) was prepared in the manner of the method according to JP2012-224611A1.

To a reactor, 10 parts of the salt represented by formula (I-2-a), 9.71 parts of the compound represented by formula (I-2-b) and 100 parts of dimethylformamide were added and then they were stirred at 23° C. for 30 minutes.

To the resultant mixture, 0.1 part of p-toluenesulfonic acid was added, and then refluxed and stirred for 3 hours.

Then the obtained reaction mixture was cooled to 23° C., and 240 parts of chloroform were added thereto and stirred, followed by being filtrated.

To the collected filtrate, 45 parts of 5% aqueous potassium carbonate solution were fed thereinto, followed by stirring at 23° C. for 30 minutes. Then the mixture was set still and separated into an organic phase.

To the organic phase, 70 parts of ion-exchanged water were fed and stirred at 23° C. for 30 minutes, followed by separating into an organic phase therefrom for washing: The washing step was conducted three times.

After washing, the obtained organic phase was concentrated to obtain 6.33 parts of the compound represented by formula (I-2).

MS (ESI(+) Spectrum): M⁺ 237.1
MS (ESI(−) Spectrum): M⁻ 441.1

Example 3

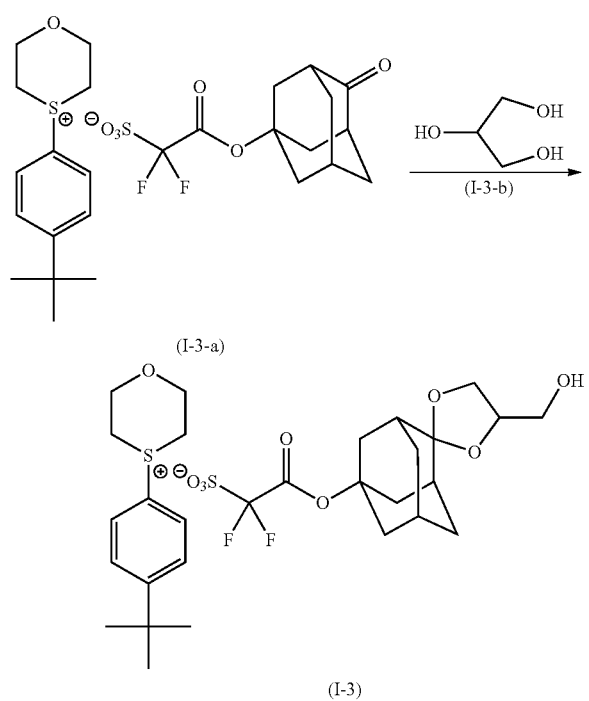

The salt represented by formula (I-3-a) was prepared in the manner of the method according to JP2012-224611A1.

To a reactor, 10 parts of the salt represented by formula (I-3-a), 6.57 parts of the compound represented by formula (I-3-b) and 100 parts of chloroform were added and then they were stirred at 23° C. for 30 minutes.

To the resultant mixture, 0.1 part of p-toluenesulfonic acid was added, and then refluxed and stirred for 3 hours.

Then the obtained reaction mixture was cooled to 23° C., and 240 parts of chloroform were added thereto and stirred, followed by being filtrated.

To the collected filtrate, 45 parts of 5% aqueous potassium carbonate solution were fed thereinto, followed by stirring at 23° C. for 30 minutes. Then the mixture was set still and separated into an organic phase.

To the organic phase, 70 parts of ion-exchanged water were fed, stirred at 23° C. for 30 minutes, followed by separating into an organic phase therefrom for washing: The washing step was conducted three times.

After washing, the obtained organic phase was concentrated to obtain 11.01 parts of the compound represented by formula (I-3).

MS (ESI(+) Spectrum): M⁺ 237.1
MS (ESI(−) Spectrum): M⁻ 397.1

Example 4

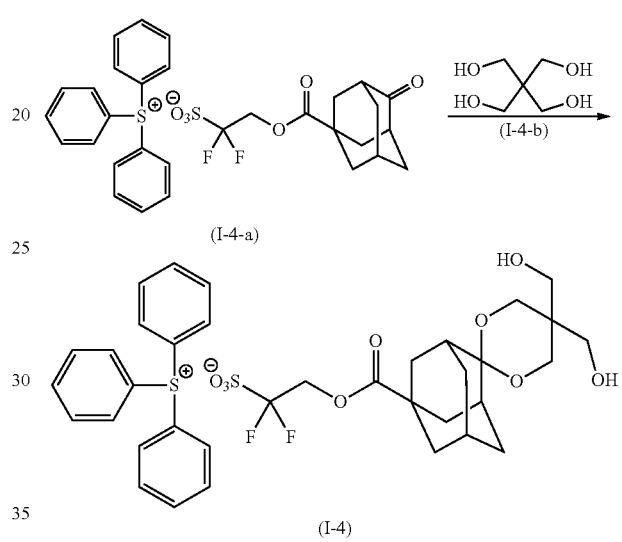

The salt represented by formula (I-4-a) was prepared in the manner of the method according to JP2010-134445A1.

To a reactor, 7.18 parts of the salt represented by formula (I-4-a), 6.5 parts of the compound represented by formula (I-4-b), 35 parts of chloroform, 14 parts of acetonitrile and 14 parts of dimethylformamide were added and then they were stirred at 23° C. for 30 minutes.

To the resultant mixture, 0.07 parts of p-toluenesulfonic acid were added, and then refluxed and stirred for 3 hours.

Then the obtained reaction mixture was cooled to 23° C., and 155 parts of chloroform were added thereto and stirred, followed by being filtrated.

To the collected filtrate, 40 parts of 5% aqueous potassium carbonate solution were fed thereinto, followed by stirring at 23° C. for 30 minutes. Then the mixture was set still and separated into an organic phase.

To the organic phase, 45 parts of ion-exchanged water were fed, stirred at 23° C. for 30 minutes, followed by separating into an organic phase therefrom for washing: The washing step was conducted three times.

After washing, to the obtained organic phase, 95 parts of ethyl acetate were added and stirred, followed by removing its supernatant therefrom. The obtained residues were dissolved in acetonitrile and concentrated to obtain 4.62 parts of the compound represented by formula (I-4).

MS (ESI(+) Spectrum): M⁺ 263.1
MS (ESI(−) Spectrum): M⁻ 455.1

Example 5

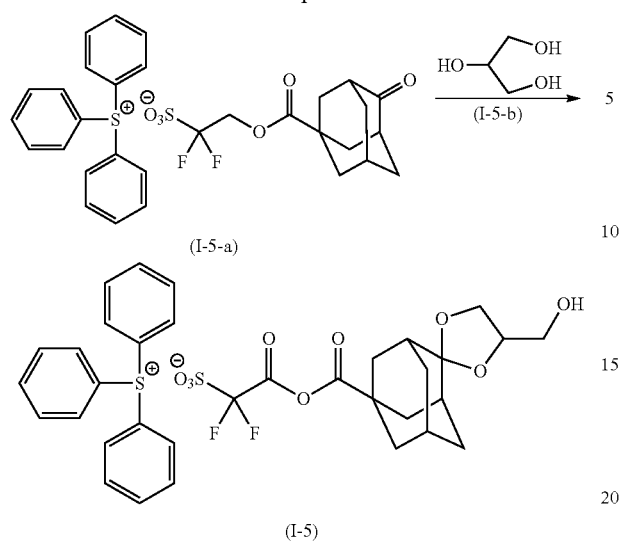

The salt represented by formula (I-5-a) was prepared in the manner of the method according to JP2010-134445A1.

To a reactor, 10.71 parts of the salt represented by formula (I-5-a), 6.57 parts of the compound represented by formula (I-5-b) and 100 parts of chloroform were added and then they were stirred at 23° C. for 30 minutes.

To the resultant mixture, 0.1 part of p-toluenesulfonic acid was added, and then refluxed and stirred for 3 hours.

Then the obtained reaction mixture was cooled to 23° C., and 240 parts of chloroform were added thereto and stirred, followed by being filtrated.

To the collected filtrate, 45 parts of 5% aqueous potassium carbonate solution were fed thereinto, followed by stirring at 23° C. for 30 minutes. Then the mixture was set still and separated into an organic phase.

To the organic phase, 70 parts of ion-exchanged water were fed, stirred at 23° C. for 30 minutes, followed by separating into an organic phase therefrom for washing: The washing step was conducted three times.

After washing, the obtained organic phase was concentrated to obtain 10.64 parts of the compound represented by formula (I-5).

MS (ESI(+) Spectrum): M⁺ 263.1
MS (ESI(−) Spectrum): M⁻ 411.1

Synthesis Example 1

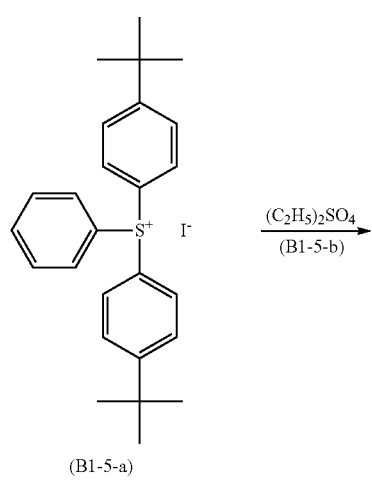

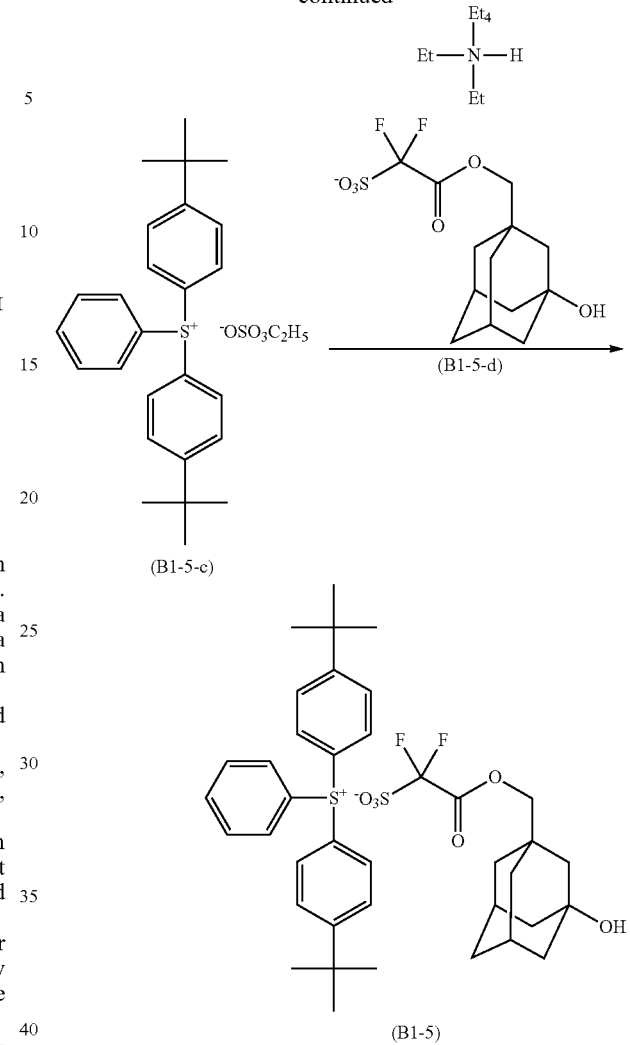

To a reactor, 50.49 parts of the salt represented by formula (B1-5-a) and 252.44 parts of chloroform were added and they were stirred at 23° C. for 30 minutes. Then 16.27 parts of the salt represented by formula (B1-5-b) were dropped thereto and then stirred at 23° C. for an hour to obtain a solution containing the salt represented by formula (B1-5-c)

To the obtained solution, 48.8 parts of the salt represented by formula (B1-5-d) and 84.15 parts of ion-exchanged water were added then stirred at 23° C. for 12 hours to obtain a reaction solution with two separated phases. Then chloroform layer was separated therefrom, and 84.15 parts of ion-exchanged water were added thereto for washing: This washing step was conducted 5 times.

To the washed chloroform layer, 3.88 parts of active carbon were added and then they were stirred, followed by conducting filtration.

The collected filtrate was concentrated. To the obtained residue, 125.87 parts of acetonitrile was added and stirred, followed by being concentrated.

To the obtained residue, 20.62 parts of acetonitrile and 309.30 parts of tert-butylmethylether were added and stirred at 23° C. for 30 minutes, followed by removing its supernatant therefrom. Then To the residue, 200 parts of n-heptane were added and stirred at 23° C. for 30 minutes, followed by being filtrated to obtain 61.54 parts of the salt represented by formula (B1-5).

MS (ESI(+) Spectrum): M⁺ 375.2
MS (ESI(−) Spectrum): M⁻ 339.1

Synthesis Example 2

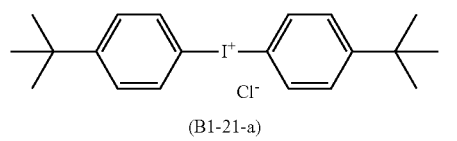

(B1-21-a)

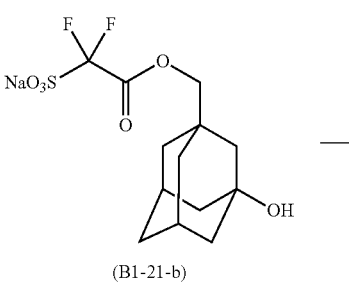

(B1-21-b)

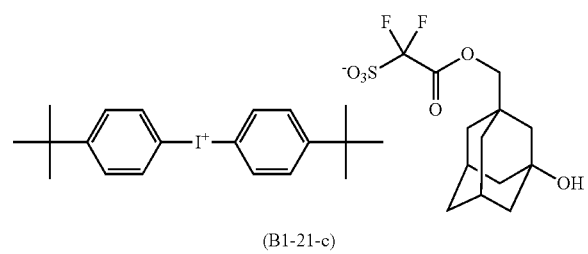

(B1-21-c)

In a reactor, 30.00 parts of the salt represented by formula (B1-21-b) which had been produced according to the method described in JP 2008-209917 A, 35.50 parts of the salt represented by formula (B1-21-a), 100 parts of chloroform and 50 parts of ion-exchanged water were fed and stirred at 23° C. for 15 hours. From the obtained reaction mixture which had two phases, a chloroform phase was collected with separation.

The chloroform phase was washed with 30 parts of ion-exchanged water for washing: This washing was conducted five times.

The washed chloroform phase was concentrated. To the obtained residue, 100 parts of tert-butylmethylether was added and then stirred at 23° C. for 30 minutes, followed by being filtrated to obtain 48.57 parts of the salt represented by formula (B1-21-c).

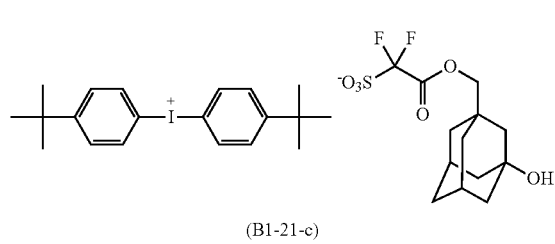

(B1-21-c)

-continued

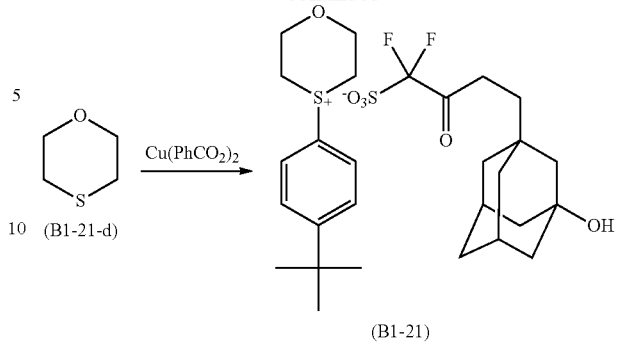

(B1-21)

Into a reactor, 20.00 parts of the salt represented by formula (B1-21-c), 2.84 parts of the compound represented by formula (B1-21-d) and 250 parts of monochlorobenzene were fed and then they were stirred at 23° C. for 30 minutes.

To the resultant mixture, 0.21 part of copper (II) dibenzoate was added. The resultant mixture was stirred at 100° C. for 1 hour. The mixture was concentrated, and then 200 parts of chloroform and 50 parts of ion-exchanged water were added to the obtained residue, followed by being stirred at 23° C. for 30 minutes. Then the organic phase was collected by separation. The organic layer was washed with 50 parts of ion-exchanged water and then they were stirred at 23° C. for 30 minutes, followed by collecting an organic phase by separation: This washing was conducted five times.

The washed organic layer was concentrated. To the residue, 53.51 parts of acetonitrile was added, and the resultant mixture was concentrated. TO the residue, 113.05 parts of tert-butylmethylether was added and then they were stirred, followed by being filtrated to obtain 10.47 parts of the salt represented by formula (B1-21).

MS (ESI(+) Spectrum): M⁺ 237.1
MS (ESI(−) Spectrum): M⁻ 339.1

Synthesis Example 3

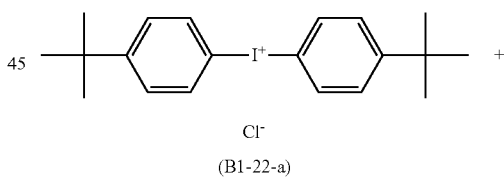

(B1-22-a)

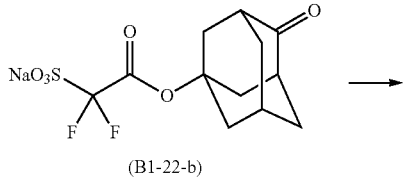

(B1-22-b)

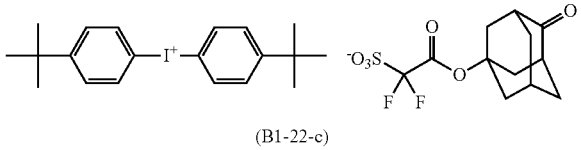

(B1-22-c)

Into a reactor, 11.26 parts of the salt represented by formula (B1-22-a), 10.00 parts of the compound represented by formula (B1-22-b), 50 parts of chloroform and 25 parts of ion-exchanged water were fed and then they were stirred at 23° C. for 15 hours. From the obtained reaction mixture which had two phases, a chloroform phase was collected with separation.

The chloroform phase was washed with 15 parts of ion-exchanged water for washing: This washing was conducted five times.

The washed chloroform phase was concentrated. To the obtained residue, 50 parts of tert-butylmethylether was added and then stirred at 23° C. for 30 minutes, followed by being filtrated to obtain 11.75 parts of the salt represented by formula (B1-22-c).

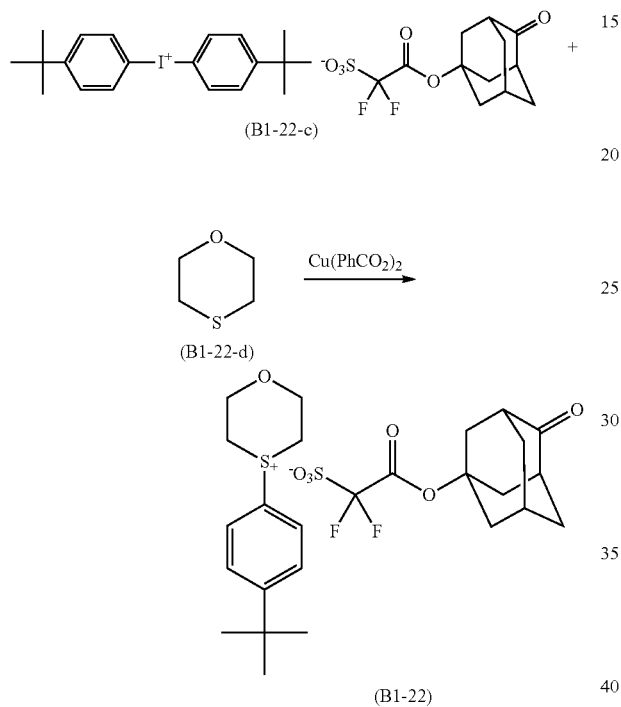

Into a reactor, 11.71 parts of the salt represented by formula (B1-22-c), 1.70 parts of the compound represented by formula (B1-22-d) and 46.84 parts of monochlorobenzene were fed and then they were stirred at 23° C. for 30 minutes.

To the resultant mixture, 0.12 part of copper (II) dibenzoate were added. The resultant mixture was stirred at 100° C. for 30 minutes.

The mixture was concentrated, and then 50 parts of chloroform and 12.50 parts of ion-exchanged water were added to the obtained residue, followed by being stirred at 23° C. for 30 minutes. Then the organic phase was collected by separation. The organic layer was washed with 12.50 parts of ion-exchanged water and then they were stirred at 23° C. for 30 minutes, followed by collecting an organic phase by separation: This washing was conducted eight times.

The washed organic layer was concentrated. To the residue, 50 parts of tert-butylmethylether was added, followed by being filtrated to obtain 6.84 parts of the salt represented by formula (B1-22).

MS (ESI(+) Spectrum): $M^+$ 237.1

MS (ESI(−) Spectrum): $M^-$ 323.0

Compounds used as monomers in the following Synthesis Examples are shown as follow.

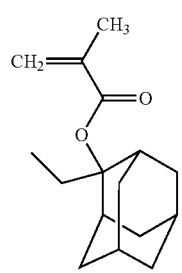
(a1-1-2)

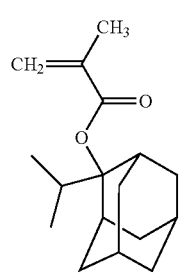
(a1-1-3)

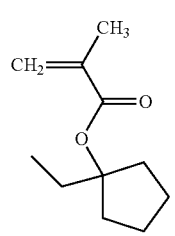
(a1-2-9)

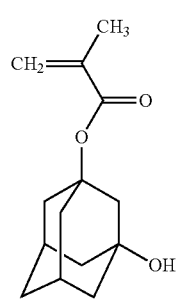
(a2-1-1)

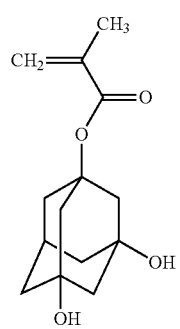
(a2-1-3)

-continued (a3-1-1) 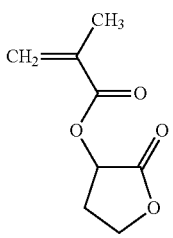

(a3-4-2) 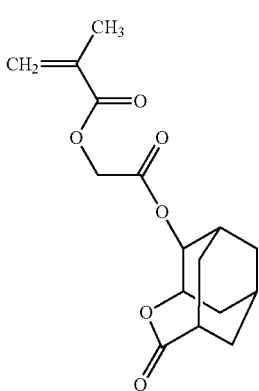

(a4-0-1) 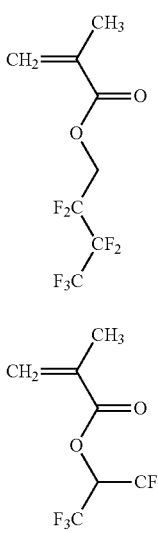

(a4-0-12)

(a4-1-7) 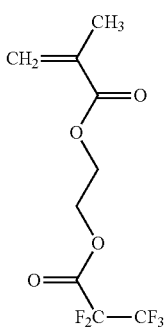

-continued (a5-1-1) 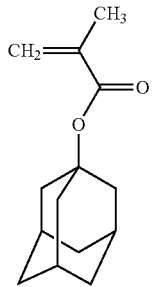

Here, each of the compounds is referred as to "monomer (X)" where "X" is the symbol of the formula representing the monomer.

Synthesis Example 4

There were mixed monomers (a1-1-3), (a1-2-9), (a2-1-3) and (a3-4-2) in a molar ratio of 45/14/2.5/38.5 (monomer (a1-1-3)/monomer (a1-2-9)/monomer (a2-1-3)/monomer (a3-4-2)) as well as propyleneglycolmonomethylether acetate in 1.5 times part based on total parts of all monomers to prepare a mixture. To the mixture, azobisisobutyronitrile as an initiator in the ratio of 1 mol % based on all monomer molar amount and azobis(2,4-dimethylvaleronitrile) as an initiator in the ratio of 3 mol % based on all monomer molar amount were added, and the obtained mixture was heated at 73° C. for about 5 hours. The reaction mixture was poured into a large amount of a mixture of methanol and water to cause precipitation. The precipitate was collected by filtration.

Then the filtrates were dissolved in propyleneglycolmonomethylether acetate and poured the resultant solution into a large amount of a mixture of methanol and water to cause precipitation, followed by being filtrated: This operation was conducted twice for purification.

As a result, a resin having a weight-average molecular weight of about $7.6 \times 10^3$ was obtained in yield of 68%. This resin is called as Resin A1. Resin A1 had the following structural units.

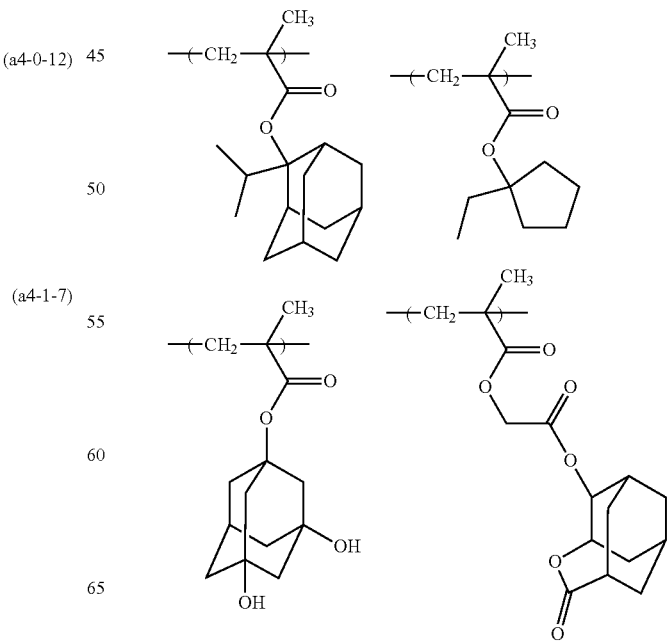

Synthesis Example 5

There were mixed monomers (a1-1-2), (a2-1-1) and (a3-1-1) in a molar ratio of 50/25/25 [monomer (a1-1-2)/monomer (a2-1-1)/monomer (a3-1-1)] as well as propyleneglycolmonomethylether acetate in 1.5 times part based on total parts of all monomers to prepare a mixture.

To the mixture, azobisisobutyronitrile as an initiator in the ratio of 1 mol % based on all monomer molar amount and azobis(2,4-dimethylvaleronitrile) as an initiator in the ratio of 3 mol % based on all monomer molar amount were added, and the obtained mixture was heated at 75° C. for about 5 hours. The reaction mixture was poured into a large amount of a mixture of methanol and water to cause precipitation. The precipitate was collected by filtration.

Then the filtrates were dissolved in propyleneglycolmonomethylether acetate and poured the resultant solution into a large amount of a mixture of methanol and water to cause precipitation, followed by being filtrated: This operation was conducted twice for purification.

As a result, a resin having a weight-average molecular weight of about $9.1 \times 10^3$ was obtained in yield of 66%. This resin is called as resin A2. Resin A2 had the following structural units.

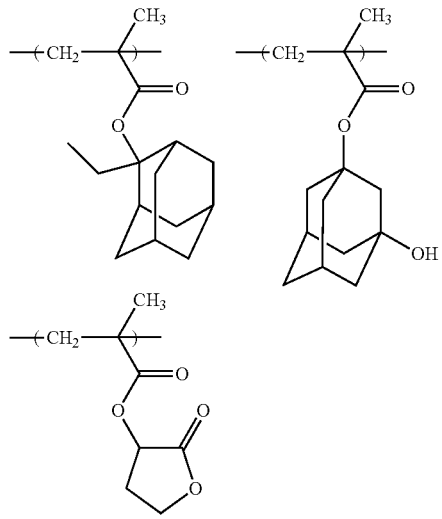

Synthesis Example 6

There were mixed monomer (a4-1-7) and 1,4-dioxane in 1.5 times part based on total parts of all monomers to prepare a mixture. To the mixture, azobisisobutyronitrile as an initiator in the ratio of 0.7 mol % based on all monomer molar amount and azobis(2,4-dimethylvaleronitrile) as an initiator in the ratio of 2.1 mol % based on all monomer molar amount were added, and the obtained mixture was heated at 75° C. for about 5 hours.

The reaction mixture was poured into a large amount of a mixture of methanol and water to cause precipitation. The precipitate was collected by filtration.

Then the reaction mixture was poured into a large amount of a mixture of methanol and water to cause precipitation. The precipitate was collected by filtration: This operation was conducted twice for purification.

As a result, a resin having a weight-average molecular weight of about $1.8 \times 10^4$ was obtained in yield of 77%. This resin is called as resin X1. Resin X1 had the following structural unit.

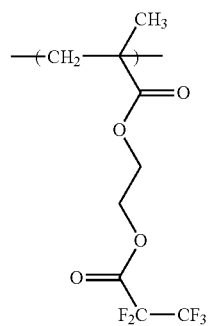

Synthesis Example 7

There were mixed monomers (a5-1-1) and (a4-0-1) in a molar ratio of 75/25 [monomers (a5-1-1)/monomer (a4-0-1)] as well as methylisobutylketone in 1.2 times part based on total parts of all monomers to prepare a mixture.

To the mixture, azobisisobutyronitrile as an initiator in the ratio of 2 mol % based on all monomer molar amount was added, and the obtained mixture was heated at 70° C. for about 5 hours.

The reaction mixture was poured into a large amount of a mixture of methanol and water to cause precipitation.

As a result, a resin having a weight-average molecular weight of about $1.7 \times 10^4$ was obtained in yield of 87%. This resin is called as resin X2. Resin X2 had the following structural units.

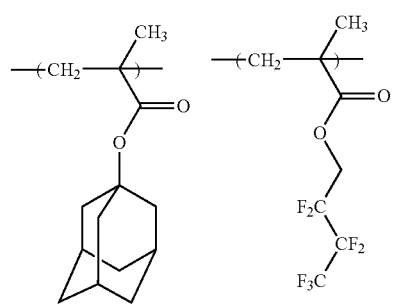

Synthesis Example 8

There were mixed monomers (a5-1-1) and (a4-0-12) in a molar ratio of 50/50 [monomers (a5-1-1)/monomer (a4-0-12)] as well as methylisobutylketone in 1.2 times part based on total parts of all monomers to prepare a mixture.

To the mixture, azobisisobutyronitrile as an initiator in the ratio of 3 mol % based on all monomer molar amount was added, and the obtained mixture was heated at 70° C. for about 5 hours.

The reaction mixture was poured into a large amount of a mixture of methanol and water to cause precipitation.

As a result, a resin having a weight-average molecular weight of about $1.0 \times 10^4$ was obtained in yield of 91%. This resin is called as resin X3. Resin X3 had the following structural units.

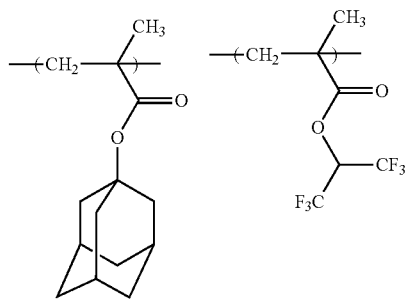

Examples 6 to 17 and Comparative Example 1

<Production of Photoresist Compositions>

The following components as listed in Table 1 were mixed and dissolved in the solvent as mentioned below, and then filtrated through a fluorine resin filter having pore diameter of 0.2 μm, to prepare photoresist compositions.

TABLE 1

| Comp. No. | Resin (kind/amount (part)) | Acid generator (kind/amount, (part)) | Salt (I) (kind/amount (part)) | Quencher (kind/amount (part)) | PB (° C.)/ PEB (° C.) |
|---|---|---|---|---|---|
| Comp. 1 | A1/10 X1/0.7 | B1-5/0.20 B1-22/0.40 | I-1/0.2 | D1/0.28 | 90/85 |
| Comp. 2 | A1/10 X1/0.7 | B1-21/0.95 B1-22/0.20 | I-2/0.2 | D1/0.28 | 90/85 |
| Comp. 3 | A1/10 X1/0.7 | B1-21/0.95 B1-22/0.20 | I-3/0.2 | D1/0.28 | 90/85 |
| Comp. 4 | A1/10 X1/0.7 | None | I-1/0.6 | D1/0.28 | 90/85 |
| Comp. 5 | A1/10 X1/0.7 | None | I-2/1.35 | D1/0.28 | 90/85 |
| Comp. 6 | A1/10 X1/0.7 | None | I-3/1.35 | D1/0.28 | 90/85 |
| Comp. 7 | A2/10 X1/0.7 | None | I-1/0.6 | D1/0.28 | 110/105 |
| Comp. 8 | A2/10 X1/0.7 | None | I-1/0.6 | D1/0.28 | 110/105 |
| Comp. 9 | A1/10 X1/0.7 | None | I-4/0.6 | D1/0.28 | 90/85 |
| Comp. 10 | A1/10 X1/0.7 | None | I-5/0.6 | D1/0.28 | 90/85 |
| Comp. 11 | A1/10 X2/0.7 | None | I-3/1.35 | D1/0.28 | 90/85 |
| Comp. 12 | A1/10 X3/0.7 | None | I-3/1.35 | D1/0.28 | 90/85 |
| Compar. Comp. 1 | A2/10 | 1X-1/0.60 | None | D1/0.28 | 110/105 |

In Table 1, each of symbols represents the following component:

<Resin>
A1: Resin A1, A2: Resin A2, X1: Resin X1, X2: Resin X2, X3: Resin X3

<Salt (I)>
I-1: Salt Represented by Formula (I-1)

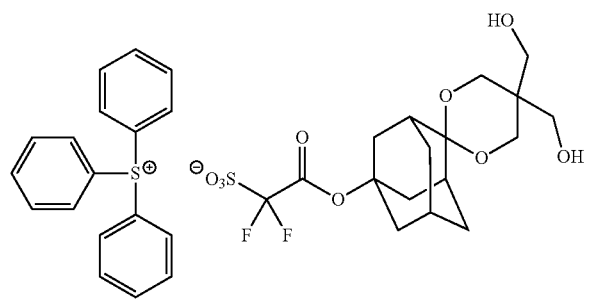

I-2: Salt Represented by Formula (I-2)

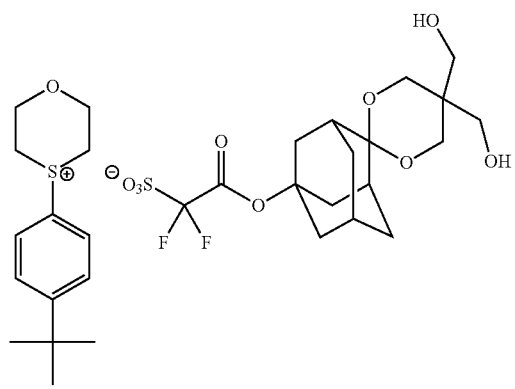

I-3: Salt Represented by Formula (I-3)

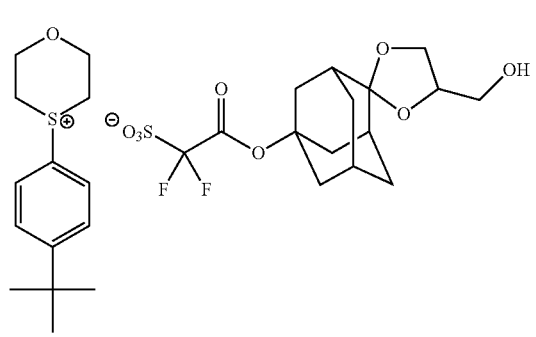

I-4: Salt Represented by Formula (I-4)

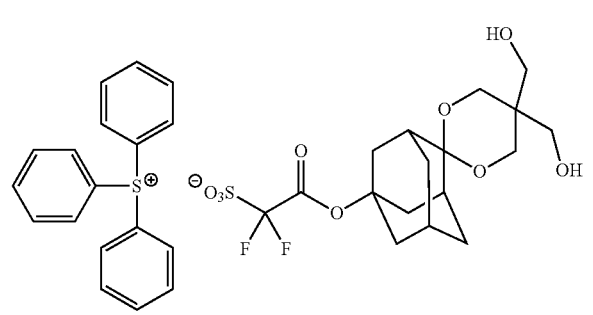

I-5: Salt represented by formula (I-5)

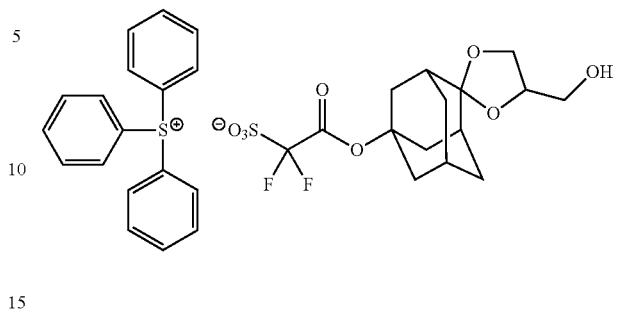

B1-x: The salt as shown below, produced in the manner of a method according to Examples of JP2011-37837A1

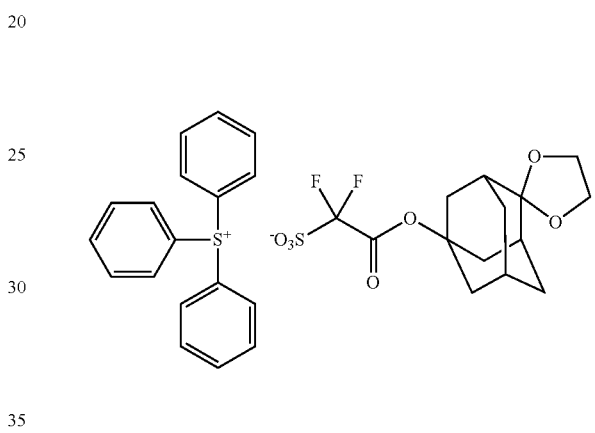

<Acid Generator>
B1-5: Salt represented by formula (B1-5)
B1-21: Salt represented by formula (B1-21)
B1-22: Salt represented by formula (B1-22)

<Quencher>
D1: The compound of the following formula, which was manufactured by Tokyo Chemical Industries, Co., Ltd.

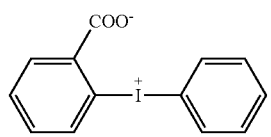

<Solvent>
Mixture of the Following Solvents

| | |
|---|---|
| propyleneglycolmonomethylether acetate | 265 parts |
| propyleneglycolmonomethylether | 20 parts |
| 2-heptanone | 20 parts |
| γ-butyrolactone | 3.5 parts |

<Evaluation>

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 100 nm after drying. The silicon wafers thus coated with the respective photoresist compositions were each prebaked on a direct hotplate at a temperature shown in the column "PB" in Table 1 for 60 seconds. Using an ArF excimer stepper for immersion exposure ("XT: 1900Gi" manufactured by ASML, NA=1.35, $\sigma_{out}$=0.85, $\sigma_{in}$=0.65, X-Y polarization), each wafer thus formed with the respective resist film was subjected to exposure with the exposure quantity being varied stepwise. For the exposure, a photomask for forming a trench pattern, which has 120 nm of its pitch and 40 nm of its trench width, was used. Ultrapure water was used as an immersion medium.

After the exposure, each wafer was subjected to post-exposure baking on a hotplate at a temperature shown in the column "PEB" in Table 1 for 60 seconds and then to development in the manner of dynamic dispense method at 23° C. for 20 seconds with butyl acetate (manufactured by Tokyo Chemical Industries, Co., Ltd) to make a photoresist pattern.

Effective sensitivity (ES): It was expressed as the exposure quantity that the width of the trench pattern became 40 nm after exposure and development.

Line Edge Roughness (LER): The photoresist patterns were obtained using any one of the compositions, with the exposure at Effective sensitivity and development in the above-mentioned manners. Then each of the photoresist patterns was observed with a scanning electron microscope. The difference between the height of the highest point and height of the lowest point as to the scabrous wall surface of the photoresist pattern was measured. When the difference was 3.5 nm or less, the evaluation for LER is marked by "○". When the difference was more than 3.5 nm, the evaluation is marked by "X". The smaller the difference is, the better the pattern is.

The results are listed in Table 2.

Further, each of the differences is also shown in parentheses in a column of "LER" in the table.

TABLE 2

| Ex. No. | Composition | LER |
|---|---|---|
| Ex. 6 | Comp. 1 | ○ (2.84) |
| Ex. 7 | Comp. 2 | ○ (2.76) |
| Ex. 8 | Comp. 3 | ○ (2.78) |
| Ex. 9 | Comp. 4 | ○ (2.94) |
| Ex. 10 | Comp. 5 | ○ (2.82) |
| Ex. 11 | Comp. 6 | ○ (2.74) |
| Ex. 12 | Comp. 7 | ○ (3.45) |
| Ex. 13 | Comp. 8 | ○ (3.44) |
| Ex. 14 | Comp. 9 | ○ (2.96) |
| EX. 15 | Comp. 10 | ○ (2.97) |
| Ex. 16 | Comp. 11 | ○ (2.70) |
| Ex. 17 | Comp. 12 | ○ (2.68) |
| Comp. Ex. 1 | Compar. Comp. 1 | X (3.98) |

The salt of the present invention is suitable for an acid generator and the photoresist composition comprising the salt of the present invention provides a good photoresist pattern with reduced LER.

What is claimed is:

1. A salt which has a moiety represented by formula (a1):

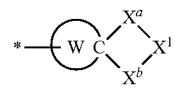

wherein $X^a$ and $X^b$ each independently represent an oxygen atom or a sulfur group;
$X^1$ represents a C1-C12 divalent saturated hydrocarbon group which has a hydroxy group;
the ring W represents a C3-C36 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them; and
* represents a binding site.

2. The salt according to claim 1 comprising a cation and an anion which has the moiety represented by formula (a1).

3. The salt according to claim 2 wherein the cation is an arylsulfonium cation.

4. The salt according to claim 1 wherein the ring W is a C6-C10 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them.

5. The salt according to claim 2 wherein the anion is represented by formula (a2):

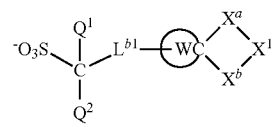

wherein $X^a$ and $X^b$ each independently represent an oxygen atom or a sulfur group;
$X^1$ represents a C1-C12 divalent saturated hydrocarbon group which has a hydroxy group;
the ring W represents a C3-C36 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them, $L^{b1}$ represents a C1-C24 divalent saturated hydrocarbon group where a methylene group can be replaced by an oxygen atom or a carbonyl group and where a hydrogen atom can be replaced by a fluorine atom or a hydroxy group; and
$Q^1$ and $Q^2$ each independently represent a fluorine atom or a C1-C6 perfluoroalkyl group.

6. The salt according to claim 5 wherein the ring W is a C6-C10 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, a C3-C12 alicyclic hydrocarbon group, a C6-C10 aromatic hydrocarbon group or a combination of any two or more of them.

7. The salt according to claim 5 wherein $L^{b1}$ is *—CO—O—$(CH_2)_t$— where t is an integer of 0 to 6 and * represents a binding site to $C(Q^1)(Q^2)$, or *—$CH_2$—O—CO— where * represents a binding site to $C(Q^1)(Q^2)$.

8. The salt according to claim 1 wherein $X^1$ is a C1-C6 alkanediyl group which has a hydroxymethyl group.

9. The salt according to claim 1 wherein $X^1$ is a divalent group represented by formula ($X^1$-1) formula ($X^1$-2), formula ($X^1$-3), formula or ($X^1$-4):

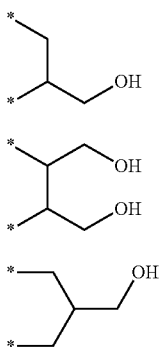

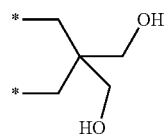

where * represents a binding site to $X^a$ or $x^b$.

10. An acid generator which comprises the salt according to claim 1.

11. A photoresist composition comprising the acid generator according to claim 10 and a resin which has an acid-labile group.

12. The photoresist composition according to claim 11, further comprising a salt which has an acidity weaker than an acid generated from the acid generator.

13. A process for producing a photoresist pattern comprising the following steps (1) to (5):
    (1) a step of applying the photoresist composition according to claim 11 on a substrate,
    (2) a step of forming a composition film by conducting drying,
    (3) a step of exposing the composition film to radiation,
    (4) a step of baking the exposed composition film, and
    (5) a step of developing the baked composition film.

* * * * *